(12) United States Patent
Demartino et al.

(10) Patent No.: US 9,918,974 B2
(45) Date of Patent: Mar. 20, 2018

(54) PYRIDONE DERIVATIVES AS REARRANGED DURING TRANSFECTION (RET) KINASE INHIBITORS

(71) Applicant: GlaxoSmithKline Intellectual Property Development Limited, Brentford, Middlesex (GB)

(72) Inventors: Michael P. Demartino, Collegeville, PA (US); Huiping Amy Guan, Shanghai (CN)

(73) Assignee: GLAXOSMITHKLINE INTELLECTUAL PROPERTY DEVELOPMENT LIMITED, Brentford, Middlesex (GB)

( * ) Notice: Subject to any disclaimer, the term of this patent is extended or adjusted under 35 U.S.C. 154(b) by 0 days.

(21) Appl. No.: 15/509,613

(22) PCT Filed: Sep. 9, 2015

(86) PCT No.: PCT/IB2015/056905
§ 371 (c)(1),
(2) Date: Mar. 8, 2017

(87) PCT Pub. No.: WO2016/038552
PCT Pub. Date: Mar. 17, 2016

(65) Prior Publication Data
US 2017/0340617 A1    Nov. 30, 2017

(30) Foreign Application Priority Data
Sep. 10, 2014    (WO) ............... PCT/CN2014/086197
Aug. 14, 2015    (WO) ............... PCT/CN2015/086995

(51) Int. Cl.
  *A61K 31/4412*   (2006.01)
  *C07D 413/12*    (2006.01)
  *C07D 401/12*    (2006.01)
  *C07D 213/69*    (2006.01)
  *A61K 31/4439*   (2006.01)

(52) U.S. Cl.
  CPC ...... *A61K 31/4439* (2013.01); *A61K 31/4412* (2013.01); *C07D 213/69* (2013.01); *C07D 401/12* (2013.01); *C07D 413/12* (2013.01)

(58) Field of Classification Search
  CPC .................. C07D 213/69; A61K 31/4412
  See application file for complete search history.

(56) References Cited

U.S. PATENT DOCUMENTS

| | | |
|---|---|---|
| 7,034,049 B1 | 4/2006 | Pevarello et al. |
| 8,236,799 B2 | 8/2012 | Hangauer |
| 8,937,071 B2 | 1/2015 | Eidam et al. |
| 9,035,063 B2 | 5/2015 | Eidam et al. |
| 9,382,238 B2 | 7/2016 | Eidam |
| 2007/0244120 A1 | 10/2007 | Dumas et al. |
| 2012/0046290 A1 | 2/2012 | Dumas et al. |
| 2013/0035326 A1 | 2/2013 | Abraham et al. |

FOREIGN PATENT DOCUMENTS

| | | |
|---|---|---|
| WO | 199932106 A1 | 7/1999 |
| WO | 199932111 A1 | 7/1999 |
| WO | 200248114 A1 | 6/2002 |
| WO | 2003059903 A2 | 7/2003 |
| WO | 2003099771 A2 | 12/2003 |
| WO | 2004024694 A1 | 3/2004 |
| WO | 2005018624 A2 | 3/2005 |
| WO | 2008002676 A2 | 1/2008 |
| WO | 2008046802 A1 | 4/2008 |
| WO | WO 2008/046802 * 4/2008 ........... C07D 471/04 |

(Continued)

OTHER PUBLICATIONS

Gradler et al., Fragment-based discovery of focal adhesion kinase inhibitors. Bioorg Med Chem Lett. Oct. 1, 2013;23(19):5401-9.
Mologni, Development of RET kinase inhibitors for targeted cancer therapy. Curr Med Chem. 2011;18(2):162-75.
Shih et al., Pharmacophore modeling and virtual screening to identify potential RET kinase inhibitors. Bioorg Med Chem Lett. Aug. 1, 2011;21(15):4490-7.
Zuercher et al., Current review of small molecule Ret kinase inhibitors. Mini Rev Med Chem. Feb. 2010;10(2):138-46.

*Primary Examiner* — Erich A Leeser
(74) *Attorney, Agent, or Firm* — Duke M. Fitch; Kathryn A. Lutomski; Edward R. Gimmi

(57) ABSTRACT

This invention relates to novel compounds which are inhibitors of the Rearranged during Transfection (RET) kinase, to pharmaceutical compositions containing them, to processes for their preparation, and to their use in therapy, alone or in combination, for the normalization of gastrointestinal sensitivity, motility and/or secretion and/or abdominal disorders or diseases and/or treatment related to diseases related to RET dysfunction or where modulation of RET activity may have therapeutic benefit including but not limited to all classifications of irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, proliferative diseases such as non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, cancer of the esophagus and gastroesophageal junction, biliary cancer, adenocarcinoma, and any malignancy with increased RET kinase activity.

19 Claims, 24 Drawing Sheets

(56) References Cited

FOREIGN PATENT DOCUMENTS

| WO | 2008058341 A1 | 5/2008 |
|----|---------------|--------|
| WO | 2011022473 A1 | 2/2011 |
| WO | 2012082817 A1 | 6/2012 |
| WO | 2014141187 A1 | 9/2014 |
| WO | 2016037578 A1 | 3/2016 |
| WO | 2016038552 A1 | 3/2016 |

* cited by examiner

PYRIDONE DERIVATIVES AS REARRANGED DURING TRANSFECTION (RET) KINASE INHIBITORS

This application is a § 371 of International Application No. PCT/IB2015/056905, filed 9 Sep. 2015, which claims the priority of PCT/CN2015/086995, filed 14 Aug. 2015, and PCT/CN2014/086197, filed 10 Sep. 2014, which are incorporated herein in their entireties.

FIELD OF INVENTION

This invention relates to novel compounds which are inhibitors of the Rearranged during Transfection (RET) kinase, to pharmaceutical compositions containing them, to processes for their preparation, and to their use in therapy, alone or in combination, for the normalization of gastrointestinal sensitivity, motility and/or secretion and/or abdominal disorders or diseases and/or treatment related to diseases related to RET dysfunction or where modulation of RET activity may have therapeutic benefit including but not limited to all classifications of irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, proliferative diseases such as non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, cancer of the esophagus and gastroesophageal junction, biliary cancer and adenocarcinoma, and any malignancy with increased RET kinase activity.

BACKGROUND OF THE INVENTION

Irritable bowel syndrome (IBS) is a common illness affecting 10-20% of individuals in developed countries and is characterized by abnormal bowel habits, bloating and visceral hypersensitivity (Camilleri, M., N. Engl. J. Med., 2012, 367:1626-1635). While the etiology of IBS is unknown it is thought to result from either a disorder between the brain and gastrointestinal tract, a disturbance in the gut microbiome or increased inflammation. The resulting gastrointestinal changes affect normal bowel transit resulting in either diarrhea or constipation. Furthermore in a majority of IBS patients the sensitization of the peripheral nervous system results in visceral hypersensitivity or allodynia (Keszthelyi, D., Eur. J. Pain, 2012, 16:1444-1454).

While IBS does not directly alter life expectancy it has a considerable effect on a patient's quality of life. Moreover there is a significant financial cost for IBS associated healthcare and lost productivity due to worker absenteeism (Nellesen, D., et al., J. Manag. Care Pharm., 2013, 19:755-764). One of the most important symptoms that greatly affect an IBS patient's quality of life is visceral pain (Spiegel, B., et al., Am. J. Gastroenterol., 2008, 103:2536-2543). Molecular strategies that inhibit IBS associated visceral pain would greatly influence the IBS patient's quality of life and reduce associated costs.

Rearranged during transfection (RET) is a neuronal growth factor receptor tyrosine kinase that is activated upon binding one of four neurotrophic factors glial cell line-derived neurotrophic factor (GDNF), neurturin, artemin and persephin in combination with a co-receptor GDNF family receptor alpha-1, 2, 3, and 4 respectively (Plaza-Menacho, I., et al., Trends Genet., 2006, 22:627-636). RET is known to play an important role in the development and survival of afferent nociceptors in the skin and gut. RET kinase knockout mice lack enteric neurons and have other nervous system anomalies suggesting that a functional RET kinase protein product is required during development (Taraviras, S. et al., Development, 1999, 126:2785-2797). Moreover population studies of patients with Hirschsprung's disease characterized by colonic obstruction due to lack of normal colonic enervation have a higher proportion of both familial and sporadic loss of function RET mutations (Butler Tjaden N., et al., Transl. Res., 2013, 162:1-15).

Similarly, aberrant RET kinase activity is associated with multiple endocrine neoplasia (MEN 2A and 2B), familial medullary thyroid carcinoma (FMTC), papillary thyroid carcinoma (PTC) and Hirschsprung's disease (HSCR) (Borello, M., et al., Expert Opin. Ther. Targets, 2013, 17:403-419). MEN 2A is a cancer syndrome resulting from a mutation in the extracellular cysteine-rich domain of RET leading to dimerization via a disulfide bond which causes constitutive activation of the tyrosine kinase activity (Wells Jr, S., et al., J. Clin. Endocrinol. Metab., 2013, 98:3149-3164). Individuals with this mutation may develop medullary thyroid carcinoma (MTC), parathyroid hyperplasia, and pheochromocytoma. MEN 2B is caused by a Met918Thr mutation in RET which changes the tyrosine kinase specificity. MEN 2B is similar to MEN 2A, but lacks the parathyroid hyperplasia and also leads to development of numerous mucosal ganglia of the lips, tongue, and intestinal tract. Chromosomal rearrangements linking the promoter and NH2-terminal domains or unrelated gene(s) to the COOH-terminus of RET kinase resulting in constitutively activated chimeric forms of the receptor (RET/PTC) are thought to be tumor initiating events in PTC (Viglietto, G. et al., Oncogene, 1995, 11:1207-1210). PTC's encompass about 80% of all thyroid carcinomas. These data indicate that inhibition of RET may be an attractive therapeutic strategy for the treatment of pain associated with IBS and other gastrointestinal disorders and for the treatment of cancers with constitutive RET kinase activity.

SUMMARY OF THE INVENTION

This invention relates to N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide, represented by Formula (I):

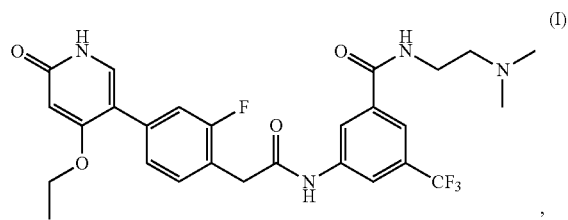 [SMILES: CCOc1cc(=O)[nH]cc1-c1ccc(CC(=O)Nc2cc(C(=O)NCCN(C)C)cc(C(F)(F)F)c2)c(F)c1]

or pharmaceutically acceptable salts thereof, and crystalline forms thereof, and to N-(3-(2-(dimethylamino)

ethoxy)-5-(trifluoromethyl)phenyl)-2-(4-(4-ethoxy-6-oxo-1,6-dihydropyridin-3-yl)-2-fluorophenyl)acetamide, represented by Formula (II):

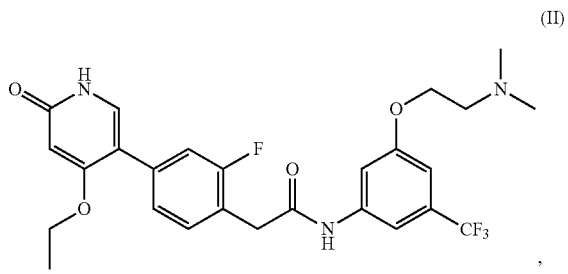 [SMILES: CCOc1cc(=O)[nH]cc1-c1ccc(CC(=O)Nc2cc(OCCN(C)C)cc(C(F)(F)F)c2)c(F)c1]

(II)

, or pharmaceutically acceptable salts thereof.

This invention also relates to a pharmaceutical composition comprising a compound of Formula (I) or (II) and a pharmaceutically acceptable excipient.

This invention also relates to a method of treating irritable bowel syndrome comprising administering to a human in need thereof an effective amount of a compound of Formula (I) or (II) or a pharmaceutically acceptable salt thereof. This invention also relates to a method of treating cancer comprising administering to a human in need thereof an effective amount of a compound of Formula (I) or (II) or a pharmaceutically acceptable salt thereof.

This invention also relates to compounds of Formula (I) or (II) for use in therapy. This invention also relates to the use of a compound of Formula (I) or (II) or a pharmaceutically acceptable salt thereof for the treatment of irritable bowel syndrome. This invention also relates to the use of a compound of Formula (I) or (II) or a pharmaceutically acceptable salt thereof for the treatment of cancer.

This invention also relates to the use of a compound of Formula (I) or (II) or a pharmaceutically acceptable salt thereof in the preparation of a medicament for the treatment of diseases mediated by RET. This invention also relates to the use of a compound of Formula (I) or (II) or a pharmaceutically acceptable salt thereof in the manufacture of a medicament for the treatment of irritable bowel syndrome. This invention also relates to the use of a compound of Formula (I) or (II) or a pharmaceutically acceptable salt thereof in the manufacture of a medicament for the treatment of cancer.

DETAILED DESCRIPTION OF THE INVENTION

Figure 1:
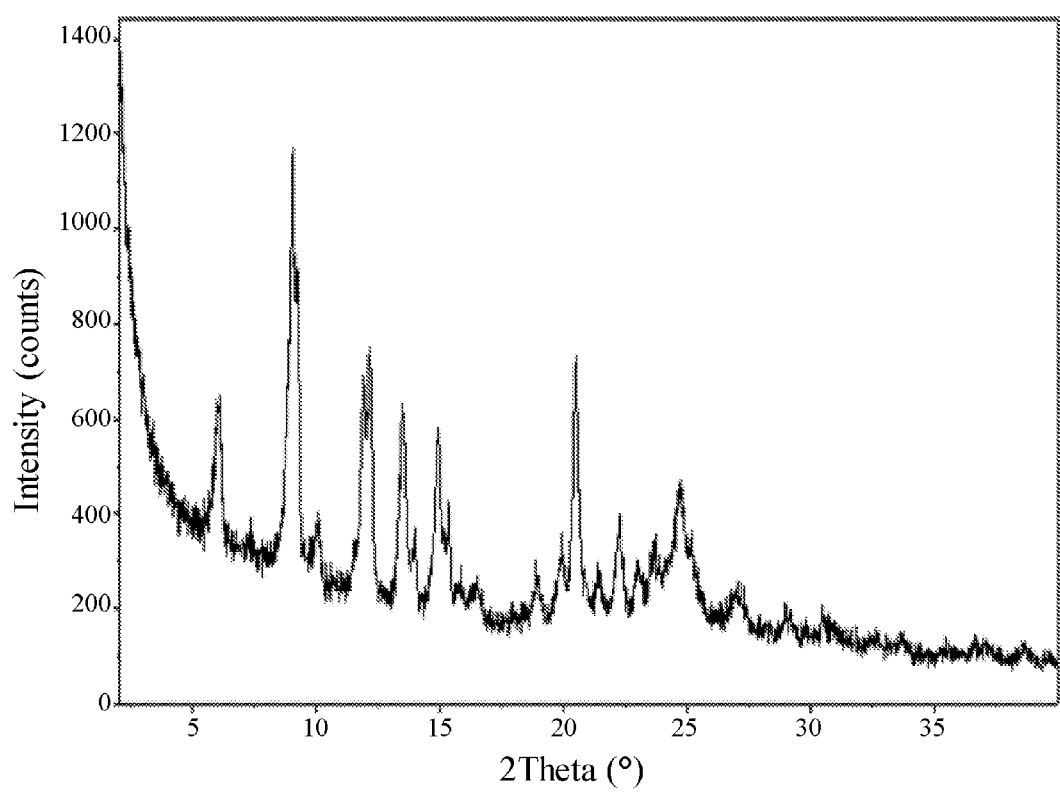
FIG. 1 shows an X-ray powder diffraction pattern of hydrate 1 of the hydrochloric acid salt of the compound of Formula (I).

This invention relates to compounds of the Formula (I) or (II) or pharmaceutically acceptable salts thereof as defined above.

A person of ordinary skills in the art recognizes that compounds of the present invention may have alternative names when different naming software is used.

This invention also relates to compounds of Formula (I) or (II), or pharmaceutically acceptable salts thereof, for use in therapy, in particular, for use in therapy wherein the subject is a human. In particular, for use in the treatment of diseases mediated by RET: irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, proliferative diseases such as non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, caner of the esophagus and gastroesophageal junction, biliary cancer and adenocarcinoma. In particular, this invention relates to compounds of Formula (I) or (II), or pharmaceutically acceptable salts thereof, for use in the treatment of irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, cancer of the esophagus and gastroesophageal junction, biliary cancer and adenocarcinoma.

This invention also relates to compounds of Formula (I) or (II), or pharmaceutically acceptable salts thereof, for use as a medicament. In another embodiment, the invention relates to the use of compounds of the invention in the preparation of a medicament for the treatment of diseases mediated by RET. This invention also relates to compounds of Formula (I) or (II), or pharmaceutically acceptable salts thereof, in the manufacture of a medicament for the treatment of irritable bowel syndrome. This invention also relates to compounds of Formula (I) or (II), or pharmaceutically acceptable salts thereof, in the manufacture of a medicament for the treatment of cancer.

This invention also relates to the use of compounds of Formula (I) or (II) in therapy. The invention further includes the use of compounds of the invention as an active therapeutic substance, in particular in the treatment of diseases mediated by RET. This invention also relates to the use of compounds of Formula (I) or (II) for the treatment of irritable bowel syndrome. This invention also relates to the use of compounds of Formula (I) or (II) for the treatment of cancer.

Because of their potential use in medicine, the salts of the compounds of Formula (I) are preferably pharmaceutically acceptable. Suitable pharmaceutically acceptable salts include those described by Berge, Bighley, and Monkhouse, *J. Pharm. Sci.* (1977) 66, pp 1-19. Salts encompassed within the term "pharmaceutically acceptable salts" refer to nontoxic salts of the compounds of this invention. Salts of the disclosed compounds may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Pharmaceutically acceptable salt may also be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, choline, quinine, quinoline, and basic amino acid such as lysine and arginine.

Other salts, which are not pharmaceutically acceptable, may be useful in the preparation of compounds of this invention and these should be considered to form a further aspect of the invention. These salts, such as trifluoroacetate, while not in themselves pharmaceutically acceptable, may be useful in the preparation of salts useful as intermediates in obtaining the compounds of the invention and their pharmaceutically acceptable salts.

If a compound of the invention is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a compound of the invention is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound.

The compound of Formula (I) or (II) may exist in a crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that the compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The present invention is further directed to certain crystalline forms of various salts of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide, in particular the hydrochloric acid salt, aspartic acid salt, hippuric acid salt, and phosphoric acid salt.

In some embodiments, a crystalline form of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride (hydrate 1 of the hydrochloric acid salt of the compound of Formula (I)) is characterized by an X-ray powder diffraction (XRPD) pattern comprising at least nine diffraction angles, when measured using Cu $K_\alpha$ radiation, selected from a group consisting of about 6.0, 6.1, 9.0, 9.2, 11.8, 11.9, 12.1, 13.3, 13.4, 13.6, 14.0, 14.8, 14.9, 15.3, 20.5, 22.2, 22.3, 24.5, 24.6, 25.0, 25.1, and 25.2 degrees 2θ. In another embodiment, hydrate 1 of the hydrochloric acid salt of the compound of Formula (I) is characterized by an X-ray powder diffraction (XRPD) pattern comprising at least eight diffraction angles or at least seven diffraction angles or at least six diffraction angles or at least five diffraction angles or at least four diffraction angles, when measured using Cu $K_\alpha$ radiation, selected from a group consisting of about 6.0, 6.1, 9.0, 9.2, 11.8, 11.9, 12.1, 13.3, 13.4, 13.6, 14.0, 14.8, 14.9, 15.3, 20.5, 22.2, 22.3, 24.5, 24.6, 25.0, 25.1, and 25.2 degrees 2θ. In another embodiment, hydrate 1 of the hydrochloric acid salt of the compound of Formula (I) is characterized by an X-ray powder diffraction (XRPD) pattern comprising at least three diffraction angles, when measured using Cu $K_\alpha$ radiation, selected from a group consisting of about 6.0, 6.1, 9.0, 9.2, 11.8, 11.9, 12.1, 13.3, 13.4, 13.6, 14.0, 14.8, 14.9, 15.3, 20.5, 22.2, 22.3, 24.5, 24.6, 25.0, 25.1, and 25.2 degrees 2θ.

In still another embodiment, hydrate 1 of the hydrochloric acid salt of the compound of Formula (I) is characterized by an X-ray powder diffraction (XRPD) pattern comprising diffraction angles, when measured using Cu $K_\alpha$ radiation, of about 6.0, 9.0, 11.8, 12.1, 13.4, 14.8, and 20.5 degrees 2θ. In yet another embodiment, hydrate 1 of the hydrochloric acid salt of the compound of Formula (I) is characterized by an X-ray powder diffraction (XRPD) pattern substantially in accordance with FIG. 1.

In other embodiments, hydrate 1 of the hydrochloric acid salt of the compound of Formula (I) is characterized by a Raman spectrum comprising at least nine peaks at positions selected from a group consisting of peaks at about 456, 581, 698, 774, 809, 952, 999, 1030, 1109, 1172, 1248, 1282, 1335, 1362, 1461, 1532, 1626, 1678, 2903, 2952, and 3033 $cm^{-1}$. In another embodiment, hydrate 1 of the hydrochloric acid salt of the compound of Formula (I) is characterized by a Raman spectrum comprising at least eight peaks or at least seven peaks or at least six peaks or at least five peaks or at least four three peaks at positions selected from a group consisting of peaks at about 456, 581, 698, 774, 809, 952, 999, 1030, 1109, 1172, 1248, 1282, 1335, 1362, 1461, 1532, 1626, 1678, 2903, 2952, and 3033 $cm^{-1}$. In another embodiment, hydrate 1 of the hydrochloric acid salt of the compound of Formula (I) is characterized by a Raman spectrum comprising at least three peaks at positions selected from a group consisting of peaks at about 456, 581, 698, 774, 809, 952, 999, 1030, 1109, 1172, 1248, 1282, 1335, 1362, 1461, 1532, 1626, 1678, 2903, 2952, and 3033 $cm^{-1}$.

In still another embodiment, hydrate 1 of the hydrochloric acid salt of the compound of Formula (I) is characterized by a Raman spectrum comprising peaks at about 774, 809, 999, 1282, 1335, 1362, 1532, 1626, 2903, 2952, and 3033 $cm^{-1}$. In yet another embodiment, hydrate 1 of the hydrochloric acid salt of the compound of Formula (I) is characterized by a Raman spectrum substantially in accordance with FIG. 2.

Figure 3:
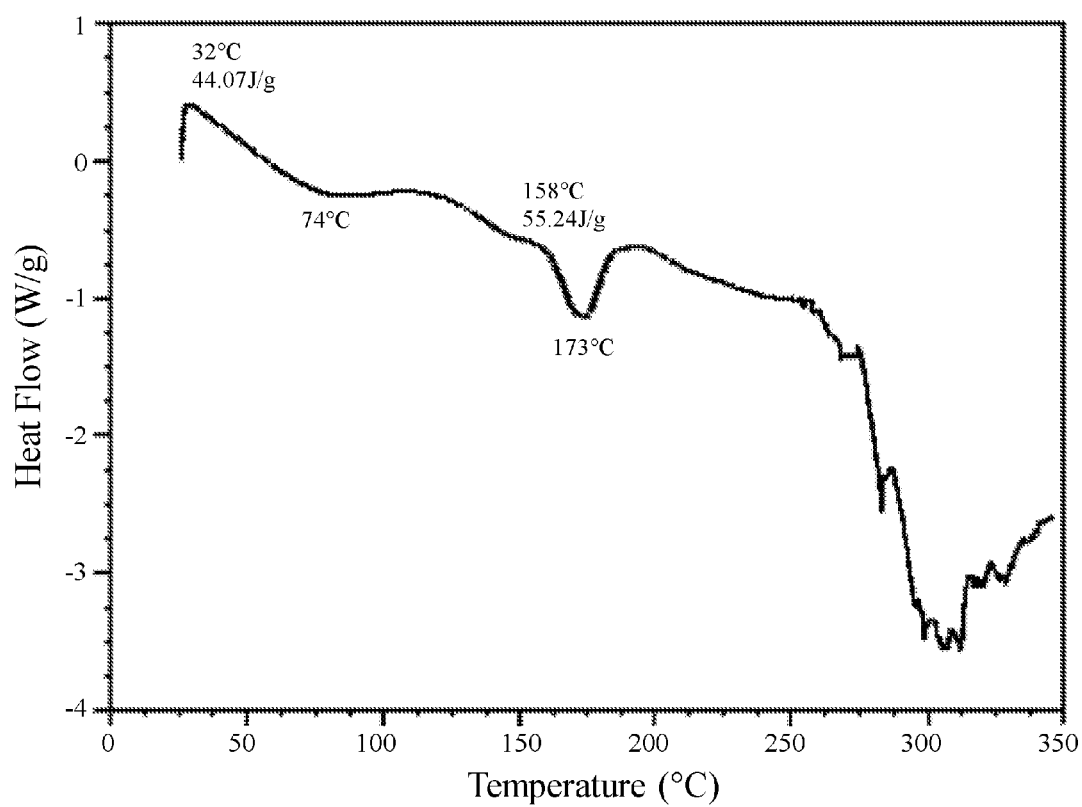
FIG. 3 shows a differential scanning calorimetry trace of hydrate 1 of the hydrochloric acid salt of the compound of Formula (I).
Figure 4:
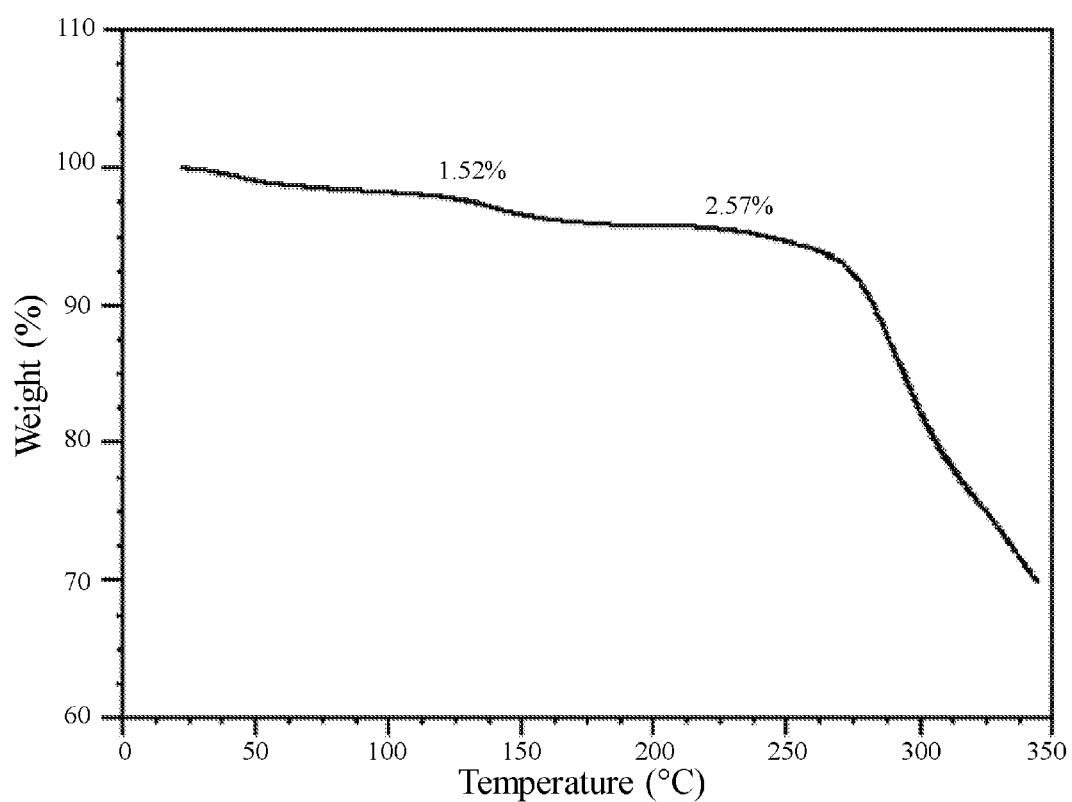
FIG. 4 shows a thermogravimetric analysis trace of hydrate 1 of the hydrochloric acid salt of the compound of Formula (I).

In further embodiments, hydrate 1 of the hydrochloric acid salt of the compound of Formula (I) is characterized by a differential scanning calorimetry trace substantially in accordance with FIG. 3 and/or a thermogravimetric analysis trace substantially in accordance with FIG. 4.

In still further embodiments, as a person having ordinary skill in the art will understand, hydrate 1 of the hydrochloric acid salt of the compound of Formula (I) is characterized by any combination of the analytical data characterizing the aforementioned embodiments. For example, in one embodiment, hydrate 1 of the hydrochloric acid salt of the compound of Formula (I) is characterized by an X-ray powder diffraction (XRPD) pattern substantially in accordance with FIG. 1 and a Raman spectrum substantially in accordance with FIG. 2 and a differential scanning calorimetry trace substantially in accordance with FIG. 3 and a thermogravimetric analysis trace substantially in accordance with FIG. 4. In another embodiment, hydrate 1 of the hydrochloric acid salt of the compound of Formula (I) is characterized by an X-ray powder diffraction (XRPD) pattern substantially in accordance with FIG. 1 and a Raman spectrum substantially in accordance with FIG. 2. In another embodiment, hydrate 1 of the hydrochloric acid salt of the compound of Formula (I) is characterized by an X-ray powder diffraction (XRPD) pattern substantially in accordance with FIG. 1 and a differential scanning calorimetry trace substantially in accordance with FIG. 3. In another embodiment, hydrate 1 of the hydrochloric acid salt of the compound of Formula (I) is characterized by an X-ray powder diffraction (XRPD) pattern substantially in accordance with FIG. 1 and a thermogravimetric analysis trace substantially in accordance with FIG. 4. In another embodiment, hydrate 1 of the hydrochloric acid salt of the compound of Formula (I) is characterized by an X-ray powder diffraction (XRPD) pattern comprising diffraction angles, when measured using Cu $K_\alpha$ radiation, of about 6.0, 9.0, 11.8, 12.1, 13.4, 14.8, and 20.5 degrees 2θ, and a Raman spectrum comprising peaks at about 774, 809, 999, 1282, 1335, 1362, 1532, 1626, 2903, 2952, and 3033 $cm^{-1}$. In another embodiment, hydrate 1 of the hydrochloric acid salt of the compound of Formula (I) is characterized by an X-ray powder diffraction (XRPD) pattern comprising diffraction angles, when measured using Cu $K_\alpha$ radiation, of about 6.0, 9.0, 11.8, 12.1, 13.4, 14.8, and 20.5 degrees 2θ, and a differential scanning calorimetry trace substantially in accordance with FIG. 3. In another embodiment, hydrate 1 of the hydrochloric acid salt of the compound of Formula (I) is characterized by an X-ray powder diffraction (XRPD) pattern comprising diffraction angles, when measured using Cu $K_\alpha$ radiation, of about 6.0, 9.0, 11.8, 12.1, 13.4, 14.8, and 20.5 degrees 2θ, and a thermogravimetric analysis trace substantially in accordance with FIG. 4.

In some embodiments, a crystalline form of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride (hydrate 2 of the hydrochloric acid salt of the compound of Formula (I)) is characterized by an X-ray powder diffraction (XRPD) pattern comprising at least nine diffraction angles, when measured using Cu $K_\alpha$ radiation, selected from a group consisting of about 6.0, 9.0, 12.1, 13.4, 13.5, 14.7, 14.8, 14.9, 15.3, 20.3, 20.4, 22.2, 22.3, 22.4, 24.7, and 24.8 degrees 2θ. In another embodiment, hydrate 2 of the hydrochloric acid salt of the compound of Formula (I) is characterized by an X-ray powder diffraction (XRPD) pattern comprising at least eight diffraction angles or at least seven diffraction angles or at least six diffraction angles or at least five diffraction angles or at least four diffraction angles, when measured using Cu $K_\alpha$ radiation, selected from a group consisting of about 6.0, 9.0, 12.1, 13.4, 13.5, 14.7, 14.8, 14.9, 15.3, 20.3, 20.4, 22.2, 22.3, 22.4, 24.7, and 24.8 degrees 2θ. In another embodiment, hydrate 2 of the hydrochloric acid salt of the compound of Formula (I) is characterized by an X-ray powder diffraction (XRPD) pattern comprising at least three diffraction angles, when measured using Cu $K_\alpha$ radiation, selected from a group consisting of about 6.0, 9.0, 12.1, 13.4, 13.5, 14.7, 14.8, 14.9, 15.3, 20.3, 20.4, 22.2, 22.3, 22.4, 24.7, and 24.8 degrees 2θ.

In still another embodiment, hydrate 2 of the hydrochloric acid salt of the compound of Formula (I) is characterized by an X-ray powder diffraction (XRPD) pattern comprising diffraction angles, when measured using Cu $K_\alpha$ radiation, of about 6.0, 9.0, 12.1, 14.7, 20.3, and 24.7 degrees 2θ. In yet another embodiment, hydrate 2 of the hydrochloric acid salt of the compound of Formula (I) is characterized by an X-ray powder diffraction (XRPD) pattern substantially in accordance with FIG. 5.

In other embodiments, hydrate 2 of the hydrochloric acid salt of the compound of Formula (I) is characterized by a Raman spectrum comprising at least nine peaks at positions selected from a group consisting of peaks at about 455, 588, 699, 734, 775, 807, 885, 949, 1000, 1033, 1112, 1181, 1247, 1269, 1283, 1332, 1366, 1425, 1466, 1530, 1550, 1570, 1627, 1684, 2902, 2946, and 3044 cm$^{-1}$. In another embodiment, hydrate 2 of the hydrochloric acid salt of the compound of Formula (I) is characterized by a Raman spectrum comprising at least eight peaks or at least seven peaks or at least six peaks or at least five peaks or at least four three peaks at positions selected from a group consisting of peaks at about 455, 588, 699, 734, 775, 807, 885, 949, 1000, 1033, 1112, 1181, 1247, 1269, 1283, 1332, 1366, 1425, 1466, 1530, 1550, 1570, 1627, 1684, 2902, 2946, and 3044 cm$^{-1}$. In another embodiment, hydrate 2 of the hydrochloric acid salt of the compound of Formula (I) is characterized by a Raman spectrum comprising at least three peaks at positions selected from a group consisting of peaks at about 455, 588, 699, 734, 775, 807, 885, 949, 1000, 1033, 1112, 1181, 1247, 1269, 1283, 1332, 1366, 1425, 1466, 1530, 1550, 1570, 1627, 1684, 2902, 2946, and 3044 cm$^{-1}$.

In still another embodiment, hydrate 2 of the hydrochloric acid salt of the compound of Formula (I) is characterized by a Raman spectrum comprising peaks at about 775, 1000, 1247, 1269, 1283, 1332, 1366, 1627, 2902, and 2946 cm$^{-1}$. In yet another embodiment, hydrate 2 of the hydrochloric acid salt of the compound of Formula (I) is characterized by a Raman spectrum substantially in accordance with FIG. 6.

Figure 7:
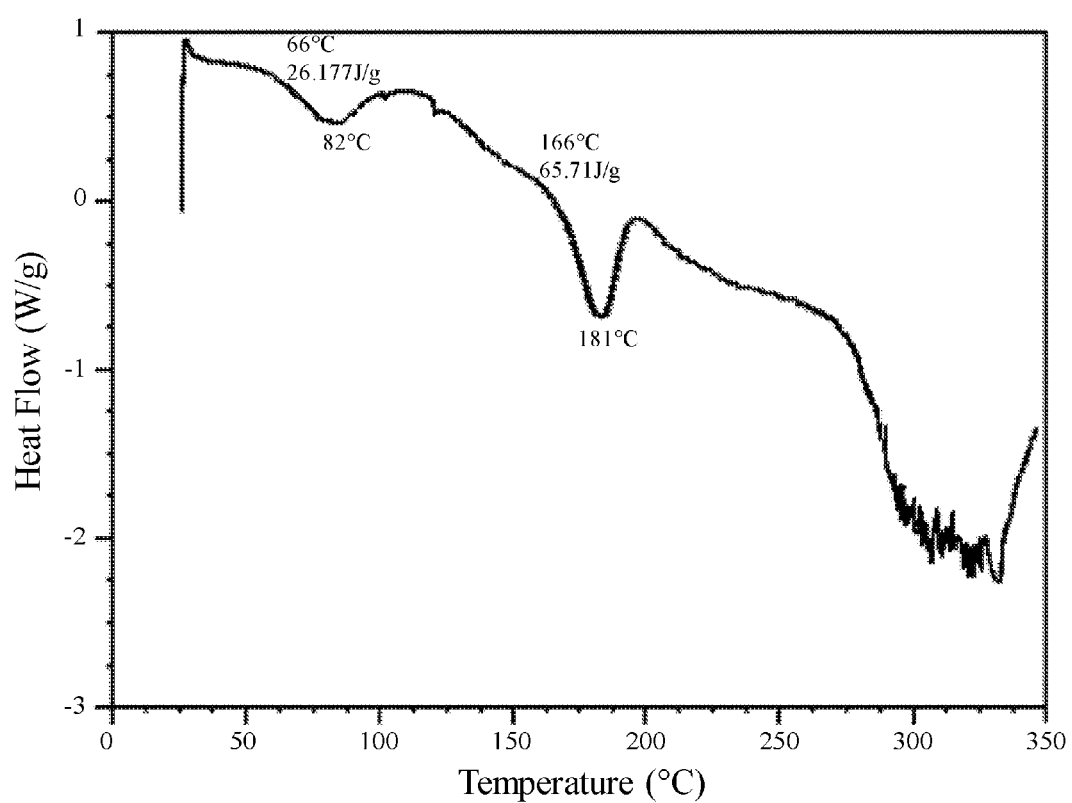
FIG. 7 shows a differential scanning calorimetry trace of hydrate 2 of the hydrochloric acid salt of the compound of Formula (I).
Figure 8:
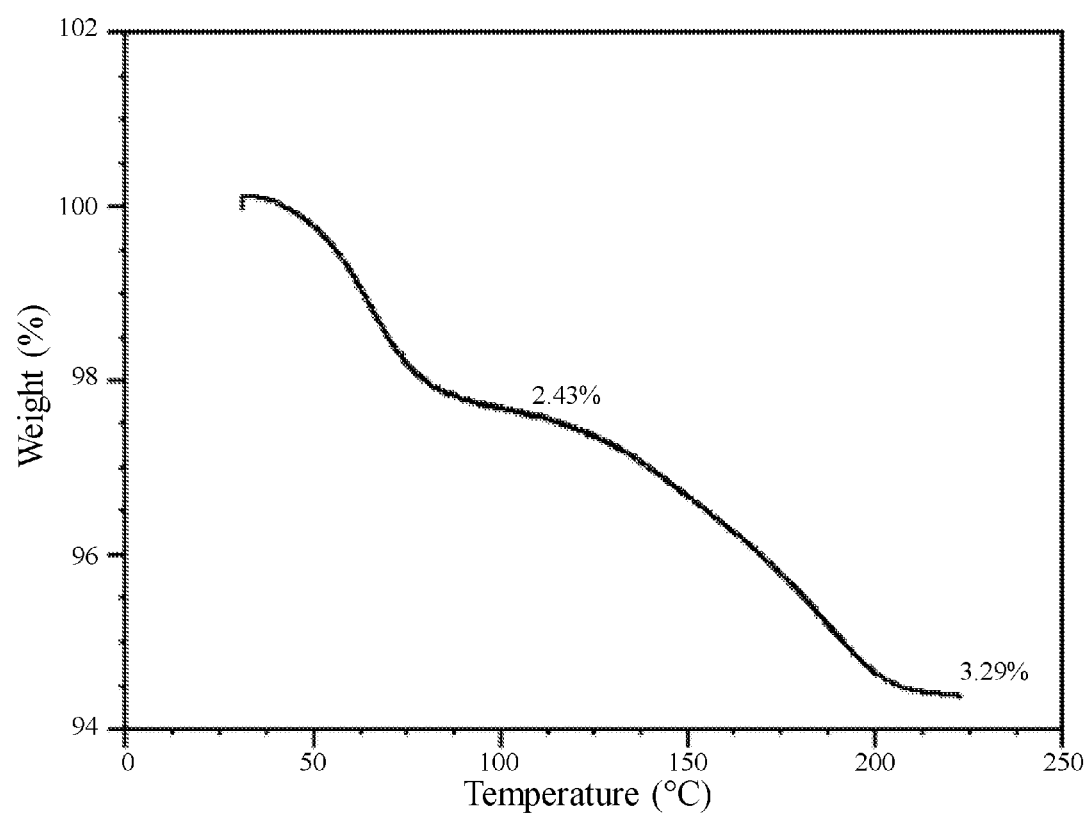
FIG. 8 shows a thermogravimetric analysis trace of hydrate 2 of the hydrochloric acid salt of the compound of Formula (I).

In further embodiments, hydrate 2 of the hydrochloric acid salt of the compound of Formula (I) is characterized by a differential scanning calorimetry trace substantially in accordance with FIG. 7 and/or a thermogravimetric analysis trace substantially in accordance with FIG. 8.

In still further embodiments, as a person having ordinary skill in the art will understand, hydrate 2 of the hydrochloric acid salt of the compound of Formula (I) is characterized by any combination of the analytical data characterizing the aforementioned embodiments. For example, in one embodiment, hydrate 2 of the hydrochloric acid salt of the compound of Formula (I) is characterized by an X-ray powder diffraction (XRPD) pattern substantially in accordance with FIG. 5 and a Raman spectrum substantially in accordance with FIG. 6 and a differential scanning calorimetry trace substantially in accordance with FIG. 7 and a thermogravimetric analysis trace substantially in accordance with FIG. 8. In another embodiment, hydrate 2 of the hydrochloric acid salt of the compound of Formula (I) is characterized by an X-ray powder diffraction (XRPD) pattern substantially in accordance with FIG. 5 and a Raman spectrum substantially in accordance with FIG. 6. In another embodiment, hydrate 2 of the hydrochloric acid salt of the compound of Formula (I) is characterized by an X-ray powder diffraction (XRPD) pattern substantially in accordance with FIG. 5 and a differential scanning calorimetry trace substantially in accordance with FIG. 7. In another embodiment, hydrate 2 of the hydrochloric acid salt of the compound of Formula (I) is characterized by an X-ray powder diffraction (XRPD) pattern substantially in accordance with FIG. 5 and a thermogravimetric analysis trace substantially in accordance with FIG. 8. In another embodiment, hydrate 2 of the hydrochloric acid salt of the compound of Formula (I) is characterized by an X-ray powder diffraction (XRPD) pattern comprising diffraction angles, when measured using Cu $K_\alpha$ radiation, of about 6.0, 9.0, 12.1, 14.7, 20.3, and 24.7 degrees 2θ, and a Raman spectrum comprising peaks at about 775, 1000, 1247, 1269, 1283, 1332, 1366, 1627, 2902, and 2946 cm$^{-1}$. In another embodiment, hydrate 2 of the hydrochloric acid salt of the compound of Formula (I) is characterized by an X-ray powder diffraction (XRPD) pattern comprising diffraction angles, when measured using Cu $K_\alpha$ radiation, of about 6.0, 9.0, 12.1, 14.7, 20.3, and 24.7 degrees 2θ, and a differential scanning calorimetry trace substantially in accordance with FIG. 7. In another embodiment, hydrate 2 of the hydrochloric acid salt of the compound of Formula (I) is characterized by an X-ray powder diffraction (XRPD) pattern comprising diffraction angles, when measured using Cu $K_\alpha$ radiation, of about 6.0, 9.0, 12.1, 14.7, 20.3, and 24.7 degrees 2θ, and a thermogravimetric analysis trace substantially in accordance with FIG. 8.

In some embodiments, a crystalline form of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride (the anhydrous hydrochloric acid salt of the compound of Formula (I)) is characterized by an X-ray powder diffraction (XRPD) pattern comprising at least nine diffraction angles, when measured using Cu $K_\alpha$ radiation, selected from a group consisting of about 8.3, 8.4, 10.7, 11.3, 15.5, 16.0, 20.0, 20.4, 20.8, 22.6, 23.2, 23.3, 23.6, 24.6, 24.9, 25.3, 25.9, 26.9, 27.3, 27.4, 28.1, and 28.2 degrees 2θ. In another embodiment, the anhydrous hydrochloric acid salt of the compound of Formula (I) is characterized by an X-ray powder diffraction (XRPD) pattern comprising at least eight diffraction angles or at least seven diffraction angles or at least six diffraction angles or at least five diffraction angles or at least four diffraction angles, when measured using Cu K$_\alpha$ radiation, selected from a group consisting of about 8.3, 8.4, 10.7, 11.3, 15.5, 16.0, 20.0, 20.4, 20.8, 22.6, 23.2, 23.3, 23.6, 24.6, 24.9, 25.3, 25.9, 26.9, 27.3, 27.4, 28.1, and 28.2 degrees 2θ. In another embodiment, the anhydrous hydrochloric acid salt of the compound of Formula (I) is characterized by an X-ray powder diffraction (XRPD) pattern comprising at least three diffraction angles, when measured using Cu K$_\alpha$ radiation, selected from a group consisting of about 8.3, 8.4, 10.7, 11.3, 15.5, 16.0, 20.0, 20.4, 20.8, 22.6, 23.2, 23.3, 23.6, 24.6, 24.9, 25.3, 25.9, 26.9, 27.3, 27.4, 28.1, and 28.2 degrees 2θ.

In still another embodiment, the anhydrous hydrochloric acid salt of the compound of Formula (I) is characterized by an X-ray powder diffraction (XRPD) pattern comprising diffraction angles, when measured using Cu K$_\alpha$ radiation, of about 16.0, 20.0, 22.6, 23.3, and 26.9 degrees 2θ. In yet another embodiment, the anhydrous hydrochloric acid salt of the compound of Formula (I) is characterized by an X-ray powder diffraction (XRPD) pattern substantially in accordance with FIG. 9.

In other embodiments, the anhydrous hydrochloric acid salt of the compound of Formula (I) is characterized by a Raman spectrum comprising at least nine peaks at positions selected from a group consisting of peaks at about 418, 454, 575, 636, 699, 771, 782, 805, 864, 894, 941, 974, 998, 1058, 1116, 1190, 1246, 1273, 1299, 1329, 1356, 1407, 1433, 1462, 1489, 1511, 1546, 1562, 1614, 1626, 1667, 1695, 2922, 2950, 2986, 3036, 3075, and 3095 cm$^{-1}$. In another embodiment, the anhydrous hydrochloric acid salt of the compound of Formula (I) is characterized by a Raman spectrum comprising at least eight peaks or at least seven peaks or at least six peaks or at least five peaks or at least four three peaks at positions selected from a group consisting of peaks at about 418, 454, 575, 636, 699, 771, 782, 805, 864, 894, 941, 974, 998, 1058, 1116, 1190, 1246, 1273, 1299, 1329, 1356, 1407, 1433, 1462, 1489, 1511, 1546, 1562, 1614, 1626, 1667, 1695, 2922, 2950, 2986, 3036, 3075, and 3095 cm$^{-1}$. In another embodiment, the anhydrous hydrochloric acid salt of the compound of Formula (I) is characterized by a Raman spectrum comprising at least three peaks at positions selected from a group consisting of peaks at about 418, 454, 575, 636, 699, 771, 782, 805, 864, 894, 941, 974, 998, 1058, 1116, 1190, 1246, 1273, 1299, 1329, 1356, 1407, 1433, 1462, 1489, 1511, 1546, 1562, 1614, 1626, 1667, 1695, 2922, 2950, 2986, 3036, 3075, and 3095 cm$^{-1}$.

In still another embodiment, the anhydrous hydrochloric acid salt of the compound of Formula (I) is characterized by a Raman spectrum comprising peaks at about 771, 805, 998, 1058, 1246, 1329, 1614, 1626, 2922, 2950, and 3036 cm$^{-1}$. In yet another embodiment, the anhydrous hydrochloric acid salt of the compound of Formula (I) is characterized by a Raman spectrum substantially in accordance with FIG. 10.

Figure 11:
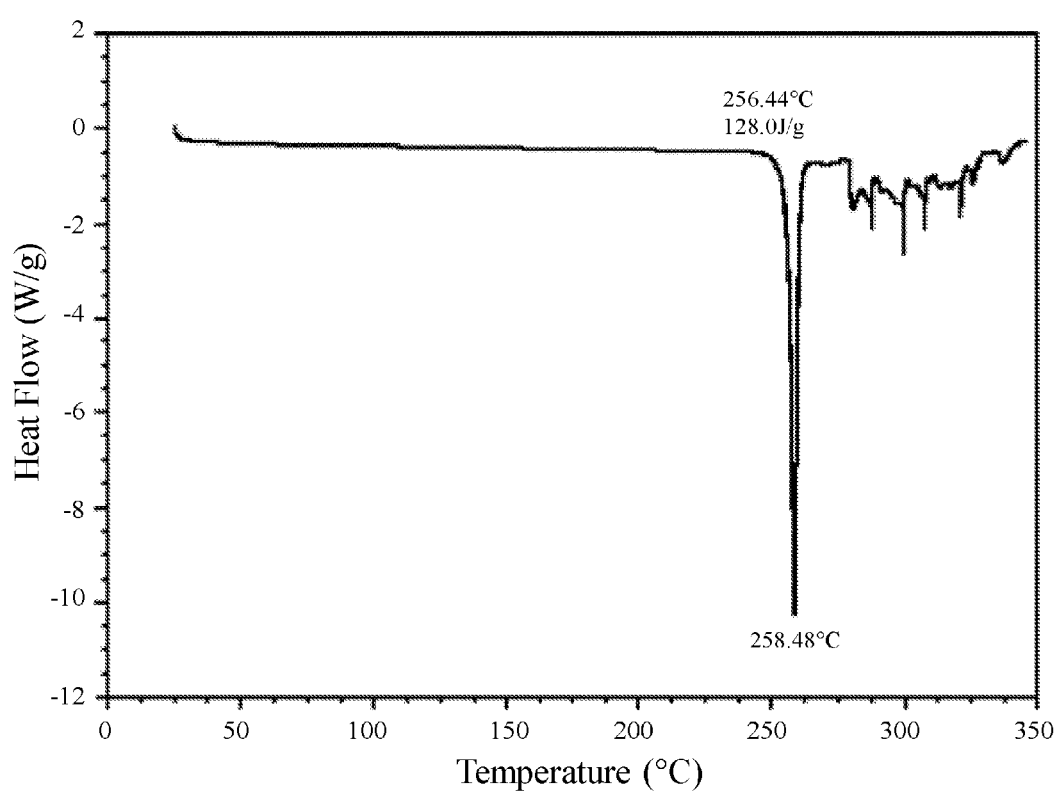
FIG. 11 shows a differential scanning calorimetry trace of the anhydrous hydrochloric acid salt of the compound of Formula (I).
Figure 12:
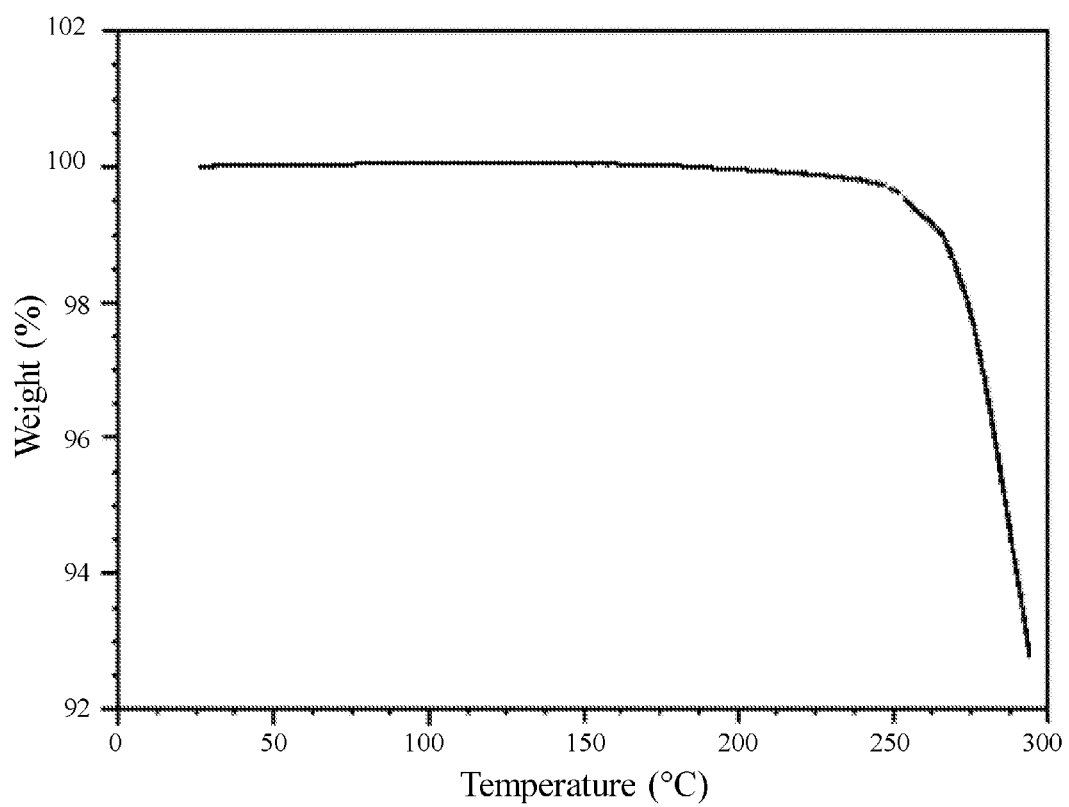
FIG. 12 shows a thermogravimetric analysis trace of the anhydrous hydrochloric acid salt of the compound of Formula (I).

In further embodiments, the anhydrous hydrochloric acid salt of the compound of Formula (I) is characterized by a differential scanning calorimetry trace substantially in accordance with FIG. 11 and/or a thermogravimetric analysis trace substantially in accordance with FIG. 12.

In still further embodiments, as a person having ordinary skill in the art will understand, the anhydrous hydrochloric acid salt of the compound of Formula (I) is characterized by any combination of the analytical data characterizing the aforementioned embodiments. For example, in one embodiment, the anhydrous hydrochloric acid salt of the compound of Formula (I) is characterized by an X-ray powder diffraction (XRPD) pattern substantially in accordance with FIG. 9 and a Raman spectrum substantially in accordance with FIG. 10 and a differential scanning calorimetry trace substantially in accordance with FIG. 11 and a thermogravimetric analysis trace substantially in accordance with FIG. 12. In another embodiment, the anhydrous hydrochloric acid salt of the compound of Formula (I) is characterized by an X-ray powder diffraction (XRPD) pattern substantially in accordance with FIG. 9 and a Raman spectrum substantially in accordance with FIG. 10. In another embodiment, the anhydrous hydrochloric acid salt of the compound of Formula (I) is characterized by an X-ray powder diffraction (XRPD) pattern substantially in accordance with FIG. 9 and a differential scanning calorimetry trace substantially in accordance with FIG. 11. In another embodiment, the anhydrous hydrochloric acid salt of the compound of Formula (I) is characterized by an X-ray powder diffraction (XRPD) pattern substantially in accordance with FIG. 9 and a thermogravimetric analysis trace substantially in accordance with FIG. 12. In another embodiment, the anhydrous hydrochloric acid salt of the compound of Formula (I) is characterized by an X-ray powder diffraction (XRPD) pattern comprising diffraction angles, when measured using Cu K$_\alpha$ radiation, of about 16.0, 20.0, 22.6, 23.3, and 26.9 degrees 2θ, and a Raman spectrum comprising peaks at about 771, 805, 998, 1058, 1246, 1329, 1614, 1626, 2922, 2950, and 3036 cm$^{-1}$. In another embodiment, the anhydrous hydrochloric acid salt of the compound of Formula (I) is characterized by an X-ray powder diffraction (XRPD) pattern comprising diffraction angles, when measured using Cu K$_\alpha$ radiation, of about 16.0, 20.0, 22.6, 23.3, and 26.9 degrees 2θ, and a differential scanning calorimetry trace substantially in accordance with FIG. 11. In another embodiment, the anhydrous hydrochloric acid salt of the compound of Formula (I) is characterized by an X-ray powder diffraction (XRPD) pattern comprising diffraction angles, when measured using Cu K$_\alpha$ radiation, of about 16.0, 20.0, 22.6, 23.3, and 26.9 degrees 2θ, and a thermogravimetric analysis trace substantially in accordance with FIG. 12.

In some embodiments, a crystalline form of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate (the aspartic acid salt of the compound of Formula (I)) is characterized by an X-ray powder diffraction (XRPD) pattern comprising at least nine diffraction angles, when measured using Cu K$_\alpha$ radiation, selected from a group consisting of about 6.7, 7.0, 7.6, 11.8, 13.9, 14.8, 15.6, 15.8, 16.2, 17.7, 18.4, 18.7, 19.1, 19.2, 20.1, 20.6, 21.0, 21.1, 21.2, 21.7, 22.1, 22.8, 23.0, 23.1, 23.3, 23.7, 23.8, 25.0, 25.1, 25.4, 25.5, 25.7, 26.2, 27.4, 28.2, 31.2, 35.9, and 36.0 degrees 2θ. In another embodiment, the aspartic acid salt of the compound of Formula (I) is characterized by an X-ray powder diffraction (XRPD) pattern comprising at least eight diffraction angles or at least seven diffraction angles or at least six diffraction angles or at least five diffraction angles or at least four diffraction angles, when measured using Cu K$_\alpha$ radiation, selected from a group consisting of about 6.7, 7.0, 7.6, 11.8, 13.9, 14.8, 15.6, 15.8, 16.2, 17.7, 18.4, 18.7, 19.1, 19.2, 20.1, 20.6, 21.0, 21.1, 21.2, 21.7, 22.1, 22.8, 23.0, 23.1, 23.3, 23.7, 23.8, 25.0, 25.1, 25.4, 25.5, 25.7, 26.2, 27.4, 28.2, 31.2, 35.9, and 36.0 degrees 2θ. In another embodiment, the aspartic acid salt of the compound of Formula (I) is characterized by an X-ray powder diffraction (XRPD) pattern comprising at least three diffraction angles, when measured using Cu K$_\alpha$ radiation, selected from a group consisting of about 6.7, 7.0, 7.6, 11.8, 13.9, 14.8, 15.6, 15.8, 16.2, 17.7, 18.4, 18.7, 19.1, 19.2, 20.1, 20.6, 21.0, 21.1, 21.2, 21.7, 22.1, 22.8, 23.0, 23.1, 23.3, 23.7, 23.8, 25.0, 25.1, 25.4, 25.5, 25.7, 26.2, 27.4, 28.2, 31.2, 35.9, and 36.0 degrees 2θ.

In still another embodiment, the aspartic acid salt of the compound of Formula (I) is characterized by an X-ray powder diffraction (XRPD) pattern comprising diffraction angles, when measured using Cu K$_\alpha$ radiation, of about 7.0, 7.6, 11.8, 16.2, 20.6, 21.7, and 23.8 degrees 2θ. In yet another embodiment, the aspartic acid salt of the compound of Formula (I) is characterized by an X-ray powder diffraction (XRPD) pattern substantially in accordance with FIG. 13.

In other embodiments, the aspartic acid salt of the compound of Formula (I) is characterized by a Raman spectrum comprising at least nine peaks at positions selected from a group consisting of peaks at about 452, 574, 691, 770, 807, 1000, 1037, 1106, 1162, 1237, 1274, 1332, 1364, 1471, 1487, 1530, 1627, 1705, 2918, and 3073 cm$^{-1}$. In another embodiment, the aspartic acid salt of the compound of Formula (I) is characterized by a Raman spectrum comprising at least eight peaks or at least seven peaks or at least six peaks or at least five peaks or at least four three peaks at positions selected from a group consisting of peaks at about 452, 574, 691, 770, 807, 1000, 1037, 1106, 1162, 1237, 1274, 1332, 1364, 1471, 1487, 1530, 1627, 1705, 2918, and 3073 cm$^{-1}$. In another embodiment, the aspartic acid salt of the compound of Formula (I) is characterized by a Raman spectrum comprising at least three peaks at positions selected from a group consisting of peaks at about 452, 574, 691, 770, 807, 1000, 1037, 1106, 1162, 1237, 1274, 1332, 1364, 1471, 1487, 1530, 1627, 1705, 2918, and 3073 cm$^{-1}$.

In still another embodiment, the aspartic acid salt of the compound of Formula (I) is characterized by a Raman spectrum comprising peaks at about 770, 807, 1000, 1237, 1274, 1332, 1364, 1471, 1627, 2918, and 3073 cm$^{-1}$. In yet another embodiment, the aspartic acid salt of the compound of Formula (I) is characterized by a Raman spectrum substantially in accordance with FIG. 14.

Figure 15:
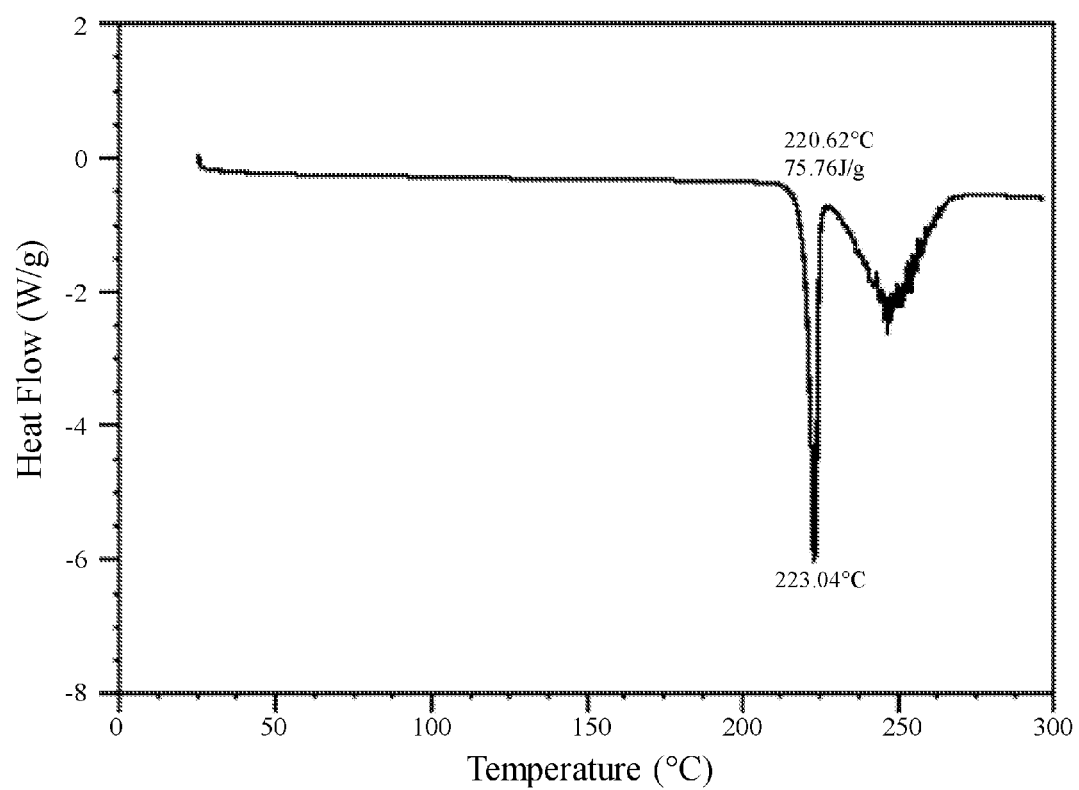
FIG. 15 shows a differential scanning calorimetry trace of the aspartic acid salt of the compound of Formula (I).
Figure 16:
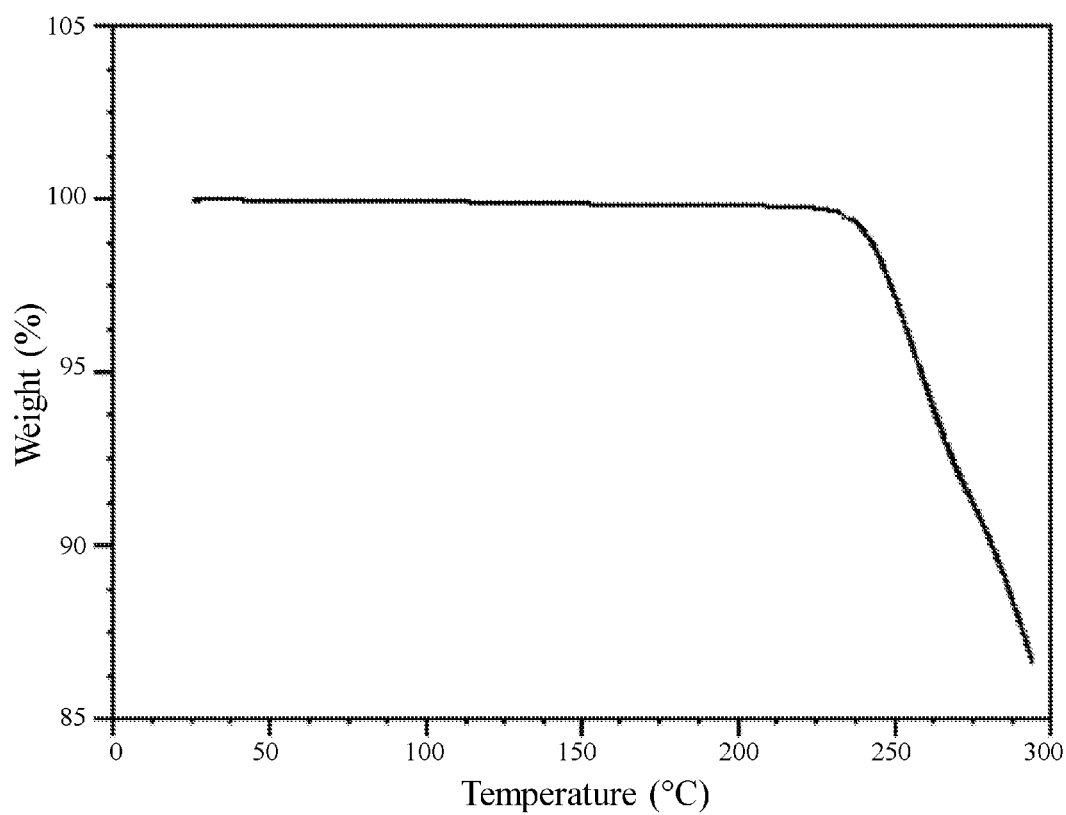
FIG. 16 shows a thermogravimetric analysis trace of the aspartic acid salt of the compound of Formula (I).

In further embodiments, the aspartic acid salt of the compound of Formula (I) is characterized by a differential scanning calorimetry trace substantially in accordance with FIG. 15 and/or a thermogravimetric analysis trace substantially in accordance with FIG. 16.

In still further embodiments, as a person having ordinary skill in the art will understand, the aspartic acid salt of the compound of Formula (I) is characterized by any combination of the analytical data characterizing the aforementioned embodiments. For example, in one embodiment, the aspartic acid salt of the compound of Formula (I) is characterized by an X-ray powder diffraction (XRPD) pattern substantially in accordance with FIG. 13 and a Raman spectrum substantially in accordance with FIG. 14 and a differential scanning calorimetry trace substantially in accordance with FIG. 15 and a thermogravimetric analysis trace substantially in accordance with FIG. 16. In another embodiment, the aspartic acid salt of the compound of Formula (I) is characterized by an X-ray powder diffraction (XRPD) pattern substantially in accordance with FIG. 13 and a Raman spectrum substantially in accordance with FIG. 14. In another embodiment, the aspartic acid salt of the compound of Formula (I) is characterized by an X-ray powder diffraction (XRPD) pattern substantially in accordance with FIG. 13 and a differential scanning calorimetry trace substantially in accordance with FIG. 15. In another embodiment, the aspartic acid salt of the compound of Formula (I) is characterized by an X-ray powder diffraction (XRPD) pattern substantially in accordance with FIG. 13 and a thermogravimetric analysis trace substantially in accordance with FIG. 16. In another embodiment, the aspartic acid salt of the compound of Formula (I) is characterized by an X-ray powder diffraction (XRPD) pattern comprising diffraction angles, when measured using Cu K$_\alpha$ radiation, of about 7.0, 7.6, 11.8, 16.2, 20.6, 21.7, and 23.8 degrees 2θ, and a Raman spectrum comprising peaks at about 770, 807, 1000, 1237, 1274, 1332, 1364, 1471, 1627, 2918, and 3073 cm$^{-1}$. In another embodiment, the aspartic acid salt of the compound of Formula (I) is characterized by an X-ray powder diffraction (XRPD) pattern comprising diffraction angles, when measured using Cu K$_\alpha$ radiation, of about 7.0, 7.6, 11.8, 16.2, 20.6, 21.7, and 23.8 degrees 2θ, and a differential scanning calorimetry trace substantially in accordance with FIG. 15. In another embodiment, the aspartic acid salt of the compound of Formula (I) is characterized by an X-ray powder diffraction (XRPD) pattern comprising diffraction angles, when measured using Cu K$_\alpha$ radiation, of about 7.0, 7.6, 11.8, 16.2, 20.6, 21.7, and 23.8 degrees 2θ, and a thermogravimetric analysis trace substantially in accordance with FIG. 16.

In some embodiments, a crystalline form of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate (the hippuric acid salt of the compound of Formula (I)) is characterized by an X-ray powder diffraction (XRPD) pattern comprising at least nine diffraction angles, when measured using Cu K$_\alpha$ radiation, selected from a group consisting of about 6.1, 9.2, 10.1, 12.0, 12.3, 12.6, 13.8, 14.0, 17.2, 17.3, 18.1, 18.4, 18.9, 19.0, 19.1, 19.6, 20.6, 21.1, 21.2, 21.5, 21.7, 22.4, 22.9, 23.5, 23.6, 24.9, 27.2, 27.4, 27.6, and 28.0 degrees 2θ. In another embodiment, the hippuric acid salt of the compound of Formula (I) is characterized by an X-ray powder diffraction (XRPD) pattern comprising at least eight diffraction angles or at least seven diffraction angles or at least six diffraction angles or at least five diffraction angles or at least four diffraction angles, when measured using Cu K$_\alpha$ radiation, selected from a group consisting of about 6.1, 9.2, 10.1, 12.0, 12.3, 12.6, 13.8, 14.0, 17.2, 17.3, 18.1, 18.4, 18.9, 19.0, 19.1, 19.6, 20.6, 21.1, 21.2, 21.5, 21.7, 22.4, 22.9, 23.5, 23.6, 24.9, 27.2, 27.4, 27.6, and 28.0 degrees 2θ. In another embodiment, the hippuric acid salt of the compound of Formula (I) is characterized by an X-ray powder diffraction (XRPD) pattern comprising at least three diffraction angles, when measured using Cu K$_\alpha$ radiation, selected from a group consisting of about 6.1, 9.2, 10.1, 12.0, 12.3, 12.6, 13.8, 14.0, 17.2, 17.3, 18.1, 18.4, 18.9, 19.0, 19.1, 19.6, 20.6, 21.1, 21.2, 21.5, 21.7, 22.4, 22.9, 23.5, 23.6, 24.9, 27.2, 27.4, 27.6, and 28.0 degrees 2θ.

In still another embodiment, the hippuric acid salt of the compound of Formula (I) is characterized by an X-ray powder diffraction (XRPD) pattern comprising diffraction angles, when measured using Cu K$_\alpha$ radiation, of about 6.1, 9.2, 12.6, 18.4, 20.6, and 22.4 degrees 2θ. In yet another embodiment, the hippuric acid salt of the compound of Formula (I) is characterized by an X-ray powder diffraction (XRPD) pattern substantially in accordance with FIG. 17.

In other embodiments, the hippuric acid salt of the compound of Formula (I) is characterized by a Raman spectrum comprising at least nine peaks at positions selected from a group consisting of peaks at about 557, 618, 694, 771, 809, 917, 997, 1042, 1108, 1236, 1272, 1335, 1366, 1467, 1537, 1575, 1601, 1630, 1695, 2944, and 3071 cm$^{-1}$. In another embodiment, the hippuric acid salt of the compound of Formula (I) is characterized by a Raman spectrum comprising at least eight peaks or at least seven peaks or at least six peaks or at least five peaks or at least four three peaks at positions selected from a group consisting of peaks at about 557, 618, 694, 771, 809, 917, 997, 1042, 1108, 1236, 1272, 1335, 1366, 1467, 1537, 1575, 1601, 1630, 1695, 2944, and 3071 cm$^{-1}$. In another embodiment, the hippuric acid salt of the compound of Formula (I) is characterized by a Raman spectrum comprising at least three peaks at positions selected from a group consisting of peaks at about 557, 618, 694, 771, 809, 917, 997, 1042, 1108, 1236, 1272, 1335, 1366, 1467, 1537, 1575, 1601, 1630, 1695, 2944, and 3071 cm$^{-1}$.

In still another embodiment, the hippuric acid salt of the compound of Formula (I) is characterized by a Raman spectrum comprising peaks at about 809, 997, 1236, 1272, 1335, 1366, 1601, 1630, 2944, and 3071 cm$^{-1}$. In yet another embodiment, the hippuric acid salt of the compound of Formula (I) is characterized by a Raman spectrum substantially in accordance with FIG. 18.

Figure 19:
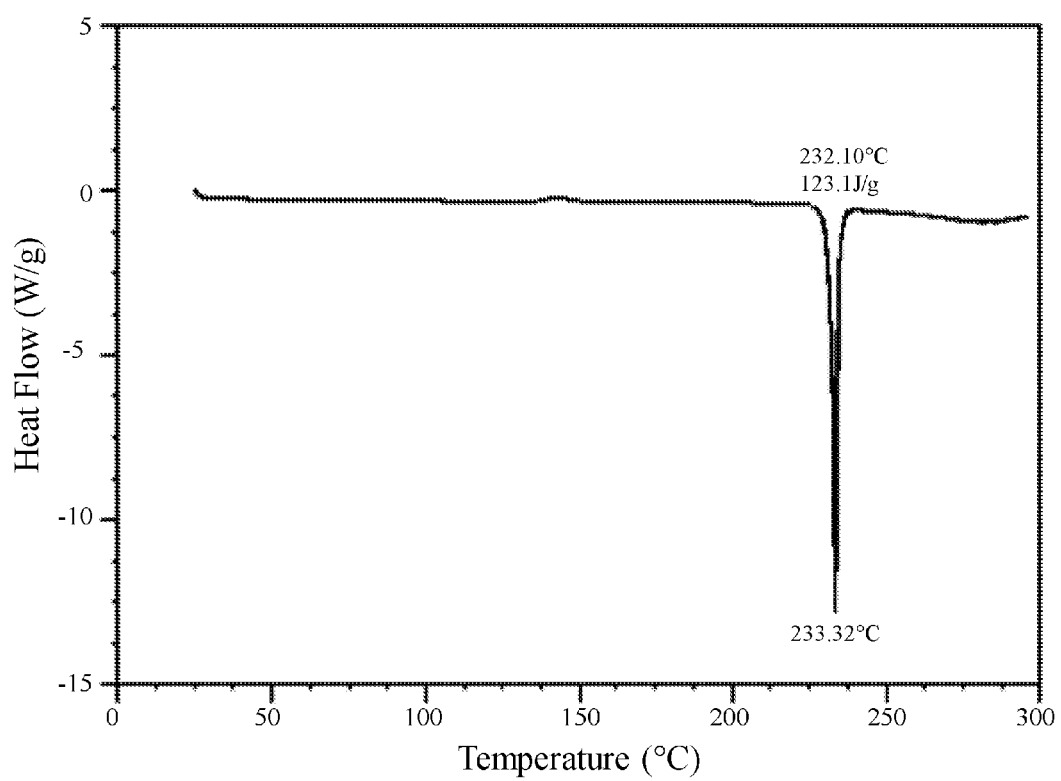
FIG. 19 shows a differential scanning calorimetry trace of the hippuric acid salt of the compound of Formula (I).
Figure 20:
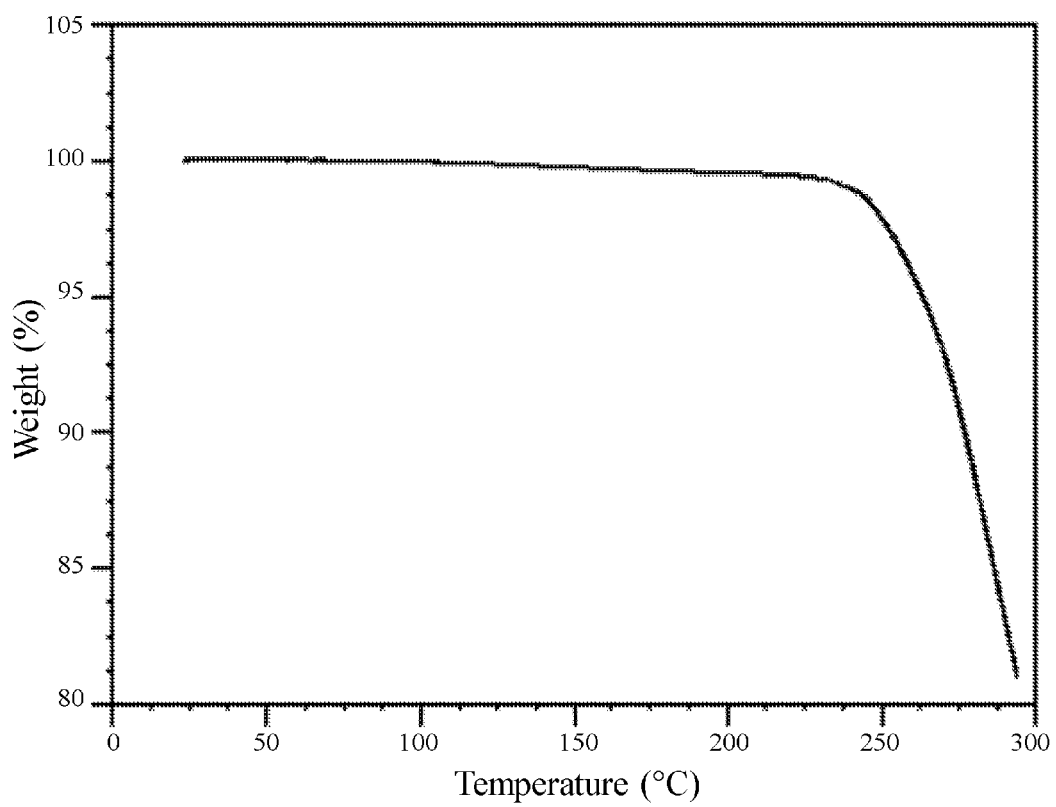
FIG. 20 shows a thermogravimetric analysis trace of the hippuric acid salt of the compound of Formula (I).

In further embodiments, the hippuric acid salt of the compound of Formula (I) is characterized by a differential scanning calorimetry trace substantially in accordance with FIG. 19 and/or a thermogravimetric analysis trace substantially in accordance with FIG. 20.

In still further embodiments, as a person having ordinary skill in the art will understand, the hippuric acid salt of the compound of Formula (I) is characterized by any combination of the analytical data characterizing the aforementioned embodiments. For example, in one embodiment, the hippuric acid salt of the compound of Formula (I) is characterized by an X-ray powder diffraction (XRPD) pattern substantially in accordance with FIG. 17 and a Raman spectrum substantially in accordance with FIG. 18 and a differential scanning calorimetry trace substantially in accordance with FIG. 19 and a thermogravimetric analysis trace substantially in accordance with FIG. 20. In another embodiment, the hippuric acid salt of the compound of Formula (I) is characterized by an X-ray powder diffraction (XRPD) pattern substantially in accordance with FIG. 17 and a Raman spectrum substantially in accordance with FIG. 18. In another embodiment, the hippuric acid salt of the compound of Formula (I) is characterized by an X-ray powder diffraction (XRPD) pattern substantially in accordance with FIG. 17 and a differential scanning calorimetry trace substantially in accordance with FIG. 19. In another embodiment, the hippuric acid salt of the compound of Formula (I) is characterized by an X-ray powder diffraction (XRPD) pattern substantially in accordance with FIG. 17 and a thermogravimetric analysis trace substantially in accordance with FIG. 20. In another embodiment, the hippuric acid salt of the compound of Formula (I) is characterized by an X-ray powder diffraction (XRPD) pattern comprising diffraction angles, when measured using Cu K$_\alpha$ radiation, of about 6.1, 9.2, 12.6, 18.4, 20.6, and 22.4 degrees 2θ, and a Raman spectrum comprising peaks at about 809, 997, 1236, 1272, 1335, 1366, 1601, 1630, 2944, and 3071 cm$^{-1}$. In another embodiment, the hippuric acid salt of the compound of Formula (I) is characterized by an X-ray powder diffraction (XRPD) pattern comprising diffraction angles, when measured using Cu K$_\alpha$ radiation, of about 6.1, 9.2, 12.6, 18.4, 20.6, and 22.4 degrees 2θ, and a differential scanning calorimetry trace substantially in accordance with FIG. 19. In another embodiment, the hippuric acid salt of the compound of Formula (I) is characterized by an X-ray powder diffraction (XRPD) pattern comprising diffraction angles, when measured using Cu K$_\alpha$ radiation, of about 6.1, 9.2, 12.6, 18.4, 20.6, and 22.4 degrees 2θ, and a thermogravimetric analysis trace substantially in accordance with FIG. 20.

In some embodiments, a crystalline form of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate (the phosphoric acid salt of the compound of Formula (I)) is characterized by an X-ray powder diffraction (XRPD) pattern comprising at least nine diffraction angles, when measured using Cu K$_\alpha$ radiation, selected from a group consisting of about 5.5, 5.6, 7.7, 9.9, 11.2, 15.4, 16.0, 16.8, 18.2, 19.9, 20.3, 23.9, 24.2, 24.4, 26.5, 26.7, 27.0, and 28.7 degrees 2θ. In another embodiment, the phosphoric acid salt of the compound of Formula (I) is characterized by an X-ray powder diffraction (XRPD) pattern comprising at least eight diffraction angles or at least seven diffraction angles or at least six diffraction angles or at least five diffraction angles or at least four diffraction angles, when measured using Cu K$_\alpha$ radiation, selected from a group consisting of about 5.5, 5.6, 7.7, 9.9, 11.2, 15.4, 16.0, 16.8, 18.2, 19.9, 20.3, 23.9, 24.2, 24.4, 26.5, 26.7, 27.0, and 28.7 degrees 2θ. In another embodiment, the phosphoric acid salt of the compound of Formula (I) is characterized by an X-ray powder diffraction (XRPD) pattern comprising at least three diffraction angles, when measured using Cu K$_\alpha$ radiation, selected from a group consisting of about 5.5, 5.6, 7.7, 9.9, 11.2, 15.4, 16.0, 16.8, 18.2, 19.9, 20.3, 23.9, 24.2, 24.4, 26.5, 26.7, 27.0, and 28.7 degrees 2θ.

In still another embodiment, the phosphoric acid salt of the compound of Formula (I) is characterized by an X-ray powder diffraction (XRPD) pattern comprising diffraction angles, when measured using Cu K$_\alpha$ radiation, of about 9.9, 16.8, 19.9, 20.3, 24.2, 26.5, and 27.0 degrees 2θ. In yet another embodiment, the phosphoric acid salt of the compound of Formula (I) is characterized by an X-ray powder diffraction (XRPD) pattern substantially in accordance with FIG. 21.

In other embodiments, the phosphoric acid salt of the compound of Formula (I) is characterized by a Raman spectrum comprising at least nine peaks at positions selected from a group consisting of peaks at about 461, 485, 529, 577, 638, 696, 732, 773, 786, 806, 867, 889, 1002, 1036, 1187, 1243, 1276, 1296, 1326, 1358, 1375, 1442, 1466, 1510, 1532, 1580, 1625, 1698, 2936, 2964, and 3069 cm$^{-1}$. In another embodiment, the phosphoric acid salt of the compound of Formula (I) is characterized by a Raman spectrum comprising at least eight peaks or at least seven peaks or at least six peaks or at least five peaks or at least four three peaks at positions selected from a group consisting of peaks at about 461, 485, 529, 577, 638, 696, 732, 773, 786, 806, 867, 889, 1002, 1036, 1187, 1243, 1276, 1296, 1326, 1358, 1375, 1442, 1466, 1510, 1532, 1580, 1625, 1698, 2936, 2964, and 3069 cm$^{-1}$. In another embodiment, the phosphoric acid salt of the compound of Formula (I) is characterized by a Raman spectrum comprising at least three peaks at positions selected from a group consisting of peaks at about 461, 485, 529, 577, 638, 696, 732, 773, 786, 806, 867, 889, 1002, 1036, 1187, 1243, 1276, 1296, 1326, 1358, 1375, 1442, 1466, 1510, 1532, 1580, 1625, 1698, 2936, 2964, and 3069 cm$^{-1}$.

In still another embodiment, the phosphoric acid salt of the compound of Formula (I) is characterized by a Raman spectrum comprising peaks at about 786, 806, 1002, 1036, 1243, 1296, 1326, 1375, 1625, 2936, and 2964 cm$^{-1}$. In yet another embodiment, the phosphoric acid salt of the compound of Formula (I) is characterized by a Raman spectrum substantially in accordance with FIG. 22.

Figure 23:
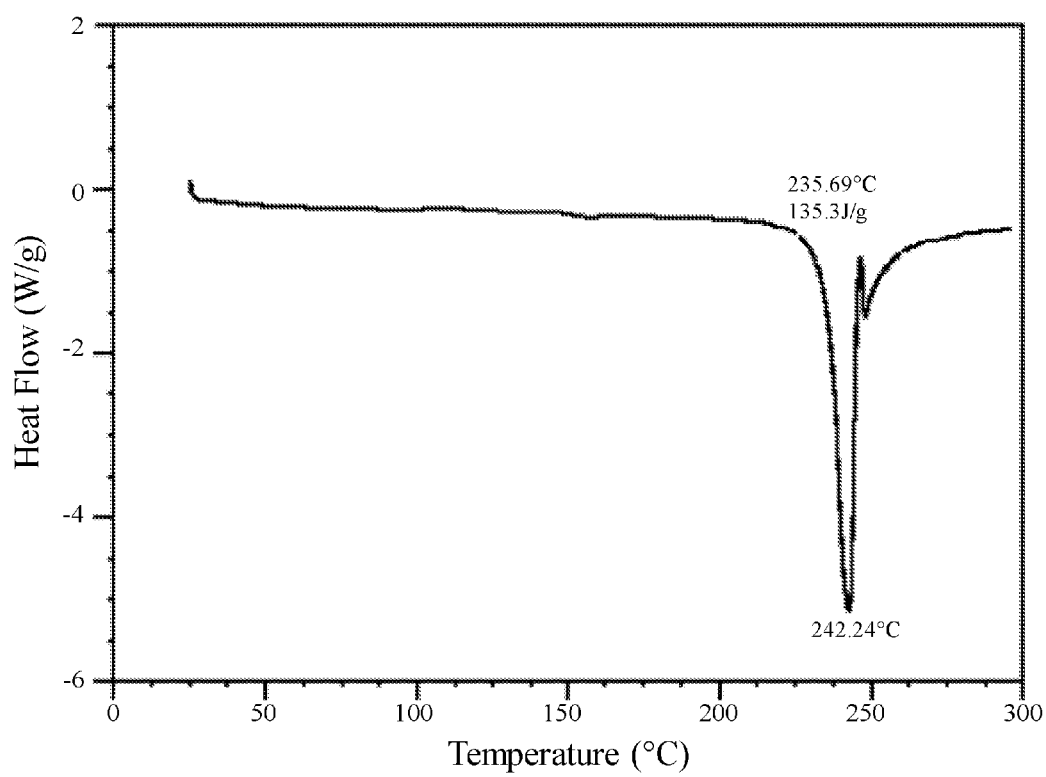
FIG. 23 shows a differential scanning calorimetry trace of the phophoric acid salt of the compound of Formula (I).
Figure 24:
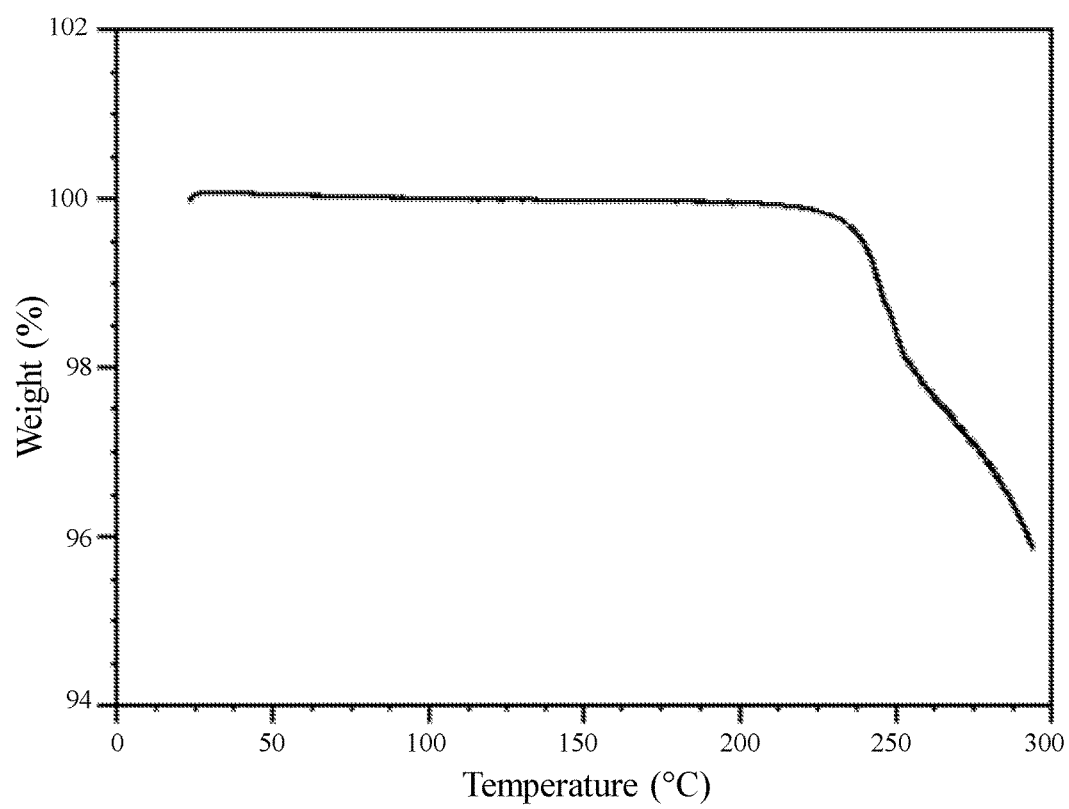
FIG. 24 shows a thermogravimetric analysis trace of the phophoric acid salt of the compound of Formula (I).

In further embodiments, the phosphoric acid salt of the compound of Formula (I) is characterized by a differential scanning calorimetry trace substantially in accordance with FIG. 23 and/or a thermogravimetric analysis trace substantially in accordance with FIG. 24.

In still further embodiments, as a person having ordinary skill in the art will understand, the phosphoric acid salt of the compound of Formula (I) is characterized by any combination of the analytical data characterizing the aforementioned embodiments. For example, in one embodiment, the phosphoric acid salt of the compound of Formula (I) is characterized by an X-ray powder diffraction (XRPD) pattern substantially in accordance with FIG. 21 and a Raman spectrum substantially in accordance with FIG. 22 and a differential scanning calorimetry trace substantially in accordance with FIG. 23 and a thermogravimetric analysis trace substantially in accordance with FIG. 24. In another embodiment, the phosphoric acid salt of the compound of Formula (I) is characterized by an X-ray powder diffraction (XRPD) pattern substantially in accordance with FIG. 21 and a Raman spectrum substantially in accordance with FIG. 22. In another embodiment, the phosphoric acid salt of the compound of Formula (I) is characterized by an X-ray powder diffraction (XRPD) pattern substantially in accordance with FIG. 21 and a differential scanning calorimetry trace substantially in accordance with FIG. 23. In another embodiment, the phosphoric acid salt of the compound of Formula (I) is characterized by an X-ray powder diffraction (XRPD) pattern substantially in accordance with FIG. 21 and a thermogravimetric analysis trace substantially in accordance with FIG. 24. In another embodiment, the phosphoric acid salt of the compound of Formula (I) is characterized by an X-ray powder diffraction (XRPD) pattern comprising diffraction angles, when measured using Cu $K_\alpha$ radiation, of about 9.9, 16.8, 19.9, 20.3, 24.2, 26.5, and 27.0 degrees 2θ, and a Raman spectrum comprising peaks at about 786, 806, 1002, 1036, 1243, 1296, 1326, 1375, 1625, 2936, and 2964 $cm^{-1}$. In another embodiment, the phosphoric acid salt of the compound of Formula (I) is characterized by an X-ray powder diffraction (XRPD) pattern comprising diffraction angles, when measured using Cu $K_\alpha$ radiation, of about 9.9, 16.8, 19.9, 20.3, 24.2, 26.5, and 27.0 degrees 2θ, and a differential scanning calorimetry trace substantially in accordance with FIG. 23. In another embodiment, the phosphoric acid salt of the compound of Formula (I) is characterized by an X-ray powder diffraction (XRPD) pattern comprising diffraction angles, when measured using Cu $K_\alpha$ radiation, of about 9.9, 16.8, 19.9, 20.3, 24.2, 26.5, and 27.0 degrees 2θ, and a thermogravimetric analysis trace substantially in accordance with FIG. 24.

An XRPD pattern will be understood to comprise a diffraction angle (expressed in degrees 2θ) of "about" a value specified herein when the XRPD pattern comprises a diffraction angle within ±0.3 degrees 2θ of the specified value. Further, it is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An X-ray powder diffraction pattern that is "substantially in accordance" with that of FIG. 1, 5, 9, 13, 17, or 21 provided herein is an XRPD pattern that would be considered by one skilled in the art to represent a compound possessing the same crystal form as the compound that provided the XRPD pattern of FIG. 1, 5, 9, 13, 17, or 21. That is, the XRPD pattern may be identical to that of FIG. 1, 5, 9, 13, 17, or 21, or more likely it may be somewhat different. Such an XRPD pattern may not necessarily show each of the lines of any one of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride, with FIG. 1 and, using expertise and knowledge in the art, readily determine whether the XRPD pattern of the sample is substantially in accordance with the XRPD pattern of hydrate 1 of the hydrochloric acid salt of the compound of Formula (I) disclosed herein. If the XRPD pattern is substantially in accordance with FIG. 1, the sample form can be readily and accurately identified as having the same form as hydrate 1 of the hydrochloric acid salt of the compound of Formula (I) disclosed herein. Similarly, if an XRPD pattern of a sample of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is substantially in accordance with FIG. 5, the sample form can be readily and accurately identified as having the same form as hydrate 2 of the hydrochloric acid salt of the compound of Formula (I) disclosed herein. Similarly, if an XRPD pattern of a sample of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is substantially in accordance with FIG. 9, the sample form can be readily and accurately identified as having the same form as the anhydrous hydrochloric acid salt of the compound of Formula (I) disclosed herein. Similarly, if an XRPD pattern of a sample of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate is substantially in accordance with FIG. 13, the sample form can be readily and accurately identified as having the same form as the aspartic acid salt of the compound of Formula (I) disclosed herein. Similarly, if an XRPD pattern of a sample of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate is substantially in accordance with FIG. 17, the sample form can be readily and accurately identified as having the same form as the hippuric acid salt of the compound of Formula (I) disclosed herein. Similarly, if an XRPD pattern of a sample of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate is substantially in accordance with FIG. 21, the sample form can be readily and accurately identified as having the same form as the phosphoric acid salt of the compound of Formula (I) disclosed herein.

A Raman spectrum will be understood to comprise a peak (expressed in $cm^{-1}$) of "about" a value specified herein when the Raman spectrum comprises a peak within ±5.0 $cm^{-1}$ of the specified value. Further, it is also well known and understood to those skilled in the art that the apparatus employed, humidity, temperature, orientation of the powder crystals, and other parameters involved in obtaining a Raman spectrum may cause some variability in the appearance, intensities, and positions of the peaks in the spectrum. A Raman spectrum that is "substantially in accordance" with that of FIG. 2, 6, 10, 14, 18, or 22 provided herein is a Raman spectrum that would be considered by one skilled in the art to represent a compound possessing the same crystal form as the compound that provided the Raman spectrum of FIG. 2, 6, 10, 14, 18, or 22. That is, the Raman spectrum may be identical to that of FIG. 2, 6, 10, 14, 18, or 22, or more likely it may be somewhat different. Such a Raman spectrum may not necessarily show each of the peaks of any one of the spectra presented herein, and/or may show a slight change in appearance, intensity, or a shift in position of said peaks resulting from differences in the conditions involved in obtaining the data. A person skilled in the art is capable of determining if a sample of a crystalline compound has the same form as, or a different form from, a form disclosed herein by comparison of their Raman spectra. For example, one skilled in the art can overlay a Raman spectrum of a sample of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride, with FIG. 2 and, using expertise and knowledge in the art, readily determine whether the Raman spectrum of the sample is substantially in accordance with the Raman spectrum of hydrate 1 of the hydrochloric acid salt of the compound of Formula (I) disclosed herein. If the Raman spectrum is substantially in accordance with FIG. 6, the sample form can be readily and accurately identified as having the same form as hydrate 2 of the hydrochloric acid salt of the compound of Formula (I) disclosed herein. Similarly, if the Raman spectrum is substantially in accordance with FIG. 10, the sample form can be readily and accurately identified as having the same form as the anhydrous hydrochloric acid salt of the compound of Formula (I) disclosed herein. Similarly, if the Raman spectrum is substantially in accordance with FIG. 14, the sample form can be readily and accurately identified as having the same form as the aspartic acid salt of the compound of Formula (I) disclosed herein. Similarly, if the Raman spectrum is substantially in accordance with FIG. 18, the sample form can be readily and accurately identified as having the same form as the hippuric acid salt of the compound of Formula (I) disclosed herein. Similarly, if the Raman spectrum is substantially in accordance with FIG. 22, the sample form can be readily and accurately identified as having the same form as the phosphoric acid salt of the compound of Formula (I) disclosed herein.

It is further understood that a compound or salt of Formula (I) or (II) may exist in tautomeric forms other than that shown in the formula and these are also included within the scope of the present invention. For example, while the compounds of Formula (I) and (II) are depicted as containing a pyridin-2-one moiety, the corresponding 2-hydroxypyridine tautomer is also included within the scope of the present invention.

It will be appreciated by those skilled in the art that certain protected derivatives of compounds of Formula (I) or (II), which may be made prior to or following a final deprotection stage, may not possess pharmacological activity as such, but may, in certain instances, be administered orally or parenterally and thereafter metabolized in the body to form compounds of the invention which are pharmacologically active. Such derivatives may therefore be described as "prodrugs". All protected derivatives and prodrugs of compounds of the invention are included within the scope of the invention.

Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1. It will further be appreciated by those skilled in the art, that certain moieties, known to those skilled in the art as "pro-moieties", for example as described by H. Bundgaard in "Design of Prodrugs" may be placed on appropriate functionalities when such functionalities are present within compounds of the invention. Preferred "pro-moieties" for compounds of the invention include: ester, carbonate ester, hemi-ester, phosphate ester, nitro ester, sulfate ester, sulfoxide, amide, carbamate, azo-, phosphamide, glycoside, ether, acetal, and ketal derivatives of the compounds of Formula (I) or (II).

Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound.

The subject invention also includes isotopically-labelled compounds, which are identical to those recited in Formula (I) or (II), but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$ or $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances.

Isotopically labelled compounds of Formula (I) and following of this invention can generally be prepared by carrying out the procedures disclosed in the Schemes and/or in the Examples below, by substituting a readily available isotopically labelled reagent for a non-isotopically labelled reagent.

Definitions

Terms are used within their accepted meanings. The following definitions are meant to clarify, but not limit, the terms defined.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

Pharmaceutical Compositions

The invention further provides a pharmaceutical composition (also referred to as pharmaceutical formulation) comprising a compound of Formula (I) or (II) or a pharmaceutically acceptable salt thereof, and one or more excipients (also referred to as carriers and/or diluents in the pharmaceutical arts). The excipients are pharmaceutically acceptable in the sense of being compatible with the other ingredients of the formulation and not deleterious to the recipient thereof (i.e., the patient).

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In accordance with another aspect of the invention there is provided a process for the preparation of a pharmaceutical composition comprising mixing (or admixing) a compound of Formula (I) or (II) or a pharmaceutically acceptable salt thereof, with at least one excipient.

Pharmaceutical compositions may be in unit dose form containing a predetermined amount of active ingredient per unit dose. Such a unit may contain a therapeutically effective dose of the compound of Formula (I) or (II) or a pharmaceutically acceptable salt thereof, or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules, powders or granules, solutions or suspensions in aqueous or non-aqueous liquids, edible foams or whips, oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as a syrup, starch paste, acadia mucilage, or solutions of cellulosic or polymeric materials and forcing through a screen. As an alternative to granulating, the powder mixture can be run through a tablet machine, resulting in imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

In certain embodiments, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein at least 10% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present as hydrate 1 of the hydrochloric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein at least 20% by weight, or at least 30% by weight, or at least 40% by weight, or at least 50% by weight, or at least 60% by weight, or at least 70% by weight, or at least 80% by weight, or at least 90% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present as hydrate 1 of the hydrochloric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein at least 95% by weight, or at least 96% by weight, or at least 97% by weight, or at least 98% by weight, or at least 99% by weight, or at least 99.5% by weight, or at least 99.8% by weight, or at least 99.9% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present as hydrate 1 of the hydrochloric acid salt of the compound of Formula (I) described herein.

In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein at least 10% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present as hydrate 2 of the hydrochloric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein at least 20% by weight, or at least 30% by weight, or at least 40% by weight, or at least 50% by weight, or at least 60% by weight, or at least 70% by weight, or at least 80% by weight, or at least 90% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present as hydrate 2 of the hydrochloric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein at least 95% by weight, or at least 96% by weight, or at least 97% by weight, or at least 98% by weight, or at least 99% by weight, or at least 99.5% by weight, or at least 99.8% by weight, or at least 99.9% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present as hydrate 2 of the hydrochloric acid salt of the compound of Formula (I) described herein.

In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein at least 10% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present as the anhydrous hydrochloric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein at least 20% by weight, or at least 30% by weight, or at least 40% by weight, or at least 50% by weight, or at least 60% by weight, or at least 70% by weight, or at least 80% by weight, or at least 90% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present as the anhydrous hydrochloric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein at least 95% by weight, or at least 96% by weight, or at least 97% by weight, or at least 98% by weight, or at least 99% by weight, or at least 99.5% by weight, or at least 99.8% by weight, or at least 99.9% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present as the anhydrous hydrochloric acid salt of the compound of Formula (I) described herein.

In certain embodiments, this invention relates to a pharmaceutical composition comprising N-(2-(dimethylamino) ethyl)-3-(2-(4-(4-ethoxy-6-oxo-1,6-dihydropyridin-3-yl)-2-fluorophenyl)acetamido)-5-(trifluoromethyl)benzamide aspartate. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate wherein at least 10% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate is present as the aspartic acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate wherein at least 20% by weight, or at least 30% by weight, or at least 40% by weight, or at least 50% by weight, or at least 60% by weight, or at least 70% by weight, or at least 80% by weight, or at least 90% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate is present as the aspartic acid salt of the compound of Formula (I) described herein. In another embodiment, this invention relates to a pharmaceutical composition comprising N-(2-(dimethylamino) ethyl)-3-(2-(4-(4-ethoxy-6-oxo-1,6-dihydropyridin-3-yl)-2-fluorophenyl)acetamido)-5-(trifluoromethyl)benzamide aspartate wherein at least 95% by weight, or at least 96% by weight, or at least 97% by weight, or at least 98% by weight, or at least 99% by weight, or at least 99.5% by weight, or at least 99.8% by weight, or at least 99.9% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate is present as the aspartic acid salt of the compound of Formula (I) described herein.

In certain embodiments, this invention relates to a pharmaceutical composition comprising N-(2-(dimethylamino) ethyl)-3-(2-(4-(4-ethoxy-6-oxo-1,6-dihydropyridin-3-yl)-2-fluorophenyl)acetamido)-5-(trifluoromethyl)benzamide hippurate. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate wherein at least 10% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate is present as the hippuric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate wherein at least 20% by weight, or at least 30% by weight, or at least 40% by weight, or at least 50% by weight, or at least 60% by weight, or at least 70% by weight, or at least 80% by weight, or at least 90% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate is present as the hippuric acid salt of the compound of Formula (I) described herein. In another embodiment, this invention relates to a pharmaceutical composition comprising N-(2-(dimethylamino) ethyl)-3-(2-(4-(4-ethoxy-6-oxo-1,6-dihydropyridin-3-yl)-2-fluorophenyl)acetamido)-5-(trifluoromethyl)benzamide hippurate wherein at least 95% by weight, or at least 96% by weight, or at least 97% by weight, or at least 98% by weight, or at least 99% by weight, or at least 99.5% by weight, or at least 99.8% by weight, or at least 99.9% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate is present as the hippuric acid salt of the compound of Formula (I) described herein.

In certain embodiments, this invention relates to a pharmaceutical composition comprising N-(2-(dimethylamino) ethyl)-3-(2-(4-(4-ethoxy-6-oxo-1,6-dihydropyridin-3-yl)-2-fluorophenyl)acetamido)-5-(trifluoromethyl)benzamide phosphate. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate wherein at least 10% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate is present as the phosphoric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate wherein at least 20% by weight, or at least 30% by weight, or at least 40% by weight, or at least 50% by weight, or at least 60% by weight, or at least 70% by weight, or at least 80% by weight, or at least 90% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate is present as the phosphoric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate wherein at least 95% by weight, or at least 96% by weight, or at least 97% by weight, or at least 98% by weight, or at least 99% by weight, or at least 99.5% by weight, or at least 99.8% by weight, or at least 99.9% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate is present as the phosphoric acid salt of the compound of Formula (I) described herein.

In another embodiment, this invention relates to a pharmaceutical composition comprising a pharmaceutically acceptable salt of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide, in particular the hydrochloric acid salt, aspartic acid salt, hippuric acid salt, or phosphoric acid salt, wherein not more than 90% by weight of the salt is amorphous. In another embodiment, this invention relates to a pharmaceutical composition comprising a pharmaceutically acceptable salt of N-(2-(dimethylamino)ethyl)-3-(2-(4-(4-ethoxy-6-oxo-1,6-dihydropyridin-3-yl)-2-fluorophenyl)acetamido)-5-(trifluoromethyl) benzamide, in particular the hydrochloric acid salt, aspartic acid salt, hippuric acid salt, or phosphoric acid salt, wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of the salt is amorphous. In another embodiment, this invention relates to a pharmaceutical composition comprising a pharmaceutically acceptable salt of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide, in particular the hydrochloric acid salt, aspartic acid salt, hippuric acid salt, or phosphoric acid salt, wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of the salt is amorphous.

In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein not more than 90% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present in a form other than hydrate 1 of the hydrochloric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of N-(2-(dimethylamino)ethyl)-3-(2-(4-(4-ethoxy-6-oxo-1, 6-dihydropyridin-3-yl)-2-fluorophenyl)acetamido)-5-(trifluoromethyl)benzamide hydrochloride is present in a form other than hydrate 1 of the hydrochloric acid salt of the compound of Formula (I) described herein. In another embodiment, this invention relates to a pharmaceutical composition comprising N-(2-(dimethylamino)ethyl)-3-(2-(4-(4-ethoxy-6-oxo-1, 6-dihydropyridin-3-yl)-2-fluorophenyl)acetamido)-5-(trifluoromethyl)benzamide hydrochloride wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present in a form other than hydrate 1 of the hydrochloric acid salt of the compound of Formula (I) described herein.

In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein not more than 90% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present in a form other than hydrate 2 of the hydrochloric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of N-(2-(dimethylamino)ethyl)-3-(2-(4-(4-ethoxy-6-oxo-1, 6-dihydropyridin-3-yl)-2-fluorophenyl)acetamido)-5-(trifluoromethyl)benzamide hydrochloride is present in a form other than hydrate 2 of the hydrochloric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present in a form other than hydrate 2 of the hydrochloric acid salt of the compound of Formula (I) described herein.

In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein not more than 90% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present in a form other than the anhydrous hydrochloric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride is present in a form other than the anhydrous hydrochloric acid salt of the compound of Formula (I) described herein. In another embodiment, this invention relates to a pharmaceutical composition comprising N-(2-(dimethylamino)ethyl)-3-(2-(4-(4-ethoxy-6-oxo-1, 6-dihydropyridin-3-yl)-2-fluorophenyl)acetamido)-5-(trifluoromethyl)benzamide hydrochloride wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of N-(2-(dimethylamino)ethyl)-3-(2-(4-(4-ethoxy-6-oxo-1, 6-dihydropyridin-3-yl)-2-fluorophenyl)acetamido)-5-(trifluoromethyl)benzamide hydrochloride is present in a form other than the anhydrous hydrochloric acid salt of the compound of Formula (I) described herein.

In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate wherein not more than 90% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate is present in a form other than the aspartic acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate is present in a form other than the aspartic acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate is present in a form other than the aspartic acid salt of the compound of Formula (I) described herein.

In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate wherein not more than 90% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate is present in a form other than the hippuric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate is present in a form other than the hippuric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate is present in a form other than the hippuric acid salt of the compound of Formula (I) described herein.

In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate wherein not more than 90% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate is present in a form other than the phosphoric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate is present in a form other than the phosphoric acid salt of the compound of Formula (I) described herein. In another embodiment, this invention relates to a pharmaceutical composition comprising N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate is present in a form other than the phosphoric acid salt of the compound of Formula (I) described herein.

As used herein, the term "treatment" refers to alleviating the specified condition, eliminating or reducing one or more symptoms of the condition, slowing or eliminating the progression of the condition, and preventing or delaying the reoccurrence of the condition in a previously afflicted or diagnosed patient or subject.

The present invention provides a method of treatment in a mammal, especially a human, suffering from irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, proliferative diseases such as non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, caner of the esophagus and gastroesophageal junction, biliary cancer and adenocarcinoma or a combination thereof. Such treatment comprises the step of administering a therapeutically effective amount of a compound of Formula (I) or (II) or a pharmaceutically acceptable salt thereof, to said mammal, particularly a human. Treatment can also comprise the step of administering a therapeutically effective amount of a pharmaceutical composition containing a compound of Formula (I) or (II) or a pharmaceutically acceptable salt thereof, to said mammal, particularly a human.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I) or (II), as well as salts thereof, may be administered as the raw chemical. Additionally, the active ingredient may be presented as a pharmaceutical composition. While it is possible that, for use in therapy, a therapeutically effective amount of a compound of Formula (I) or (II) or a pharmaceutically acceptable salt thereof, may be administered as the raw chemical, it is typically presented as the active ingredient of a pharmaceutical composition or formulation.

The precise therapeutically effective amount of a compound or salt thereof of the invention will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a compound of Formula (I) or (II) or a pharmaceutically acceptable salt thereof, will be given for the treatment in the range of about 0.1 to 100 mg/kg body weight of recipient (patient, mammal) per day and more usually in the range of 0.1 to 10 mg/kg body weight per day. Acceptable daily dosages may be from about 0.1 to about 1000 mg/day, and preferably from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the compound of Formula (I) or (II) per se. Similar dosages should be appropriate for treatment of the other conditions referred herein for treatment. In general, determination of appropriate dosing can be readily arrived at by one skilled in medicine or the pharmacy art.

The compounds of the invention may be used alone or in combination with one or more other therapeutic agents. Accordingly the present invention provides a combination comprising a compound of Formula (I) or a pharmaceutically acceptable salt thereof and one or more other therapeutic agents. Such combinations may be presented individually (wherein each active is in separate composition) or the actives are presented in a combined composition.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent. In yet another embodiment, the invention comprises a therapeutic regimen where the RET inhibitors of this disclosure are not in and of themselves active or significantly active, but when combined with another therapy, which may or may not be active as a standalone therapy, the combination provides a useful therapeutic outcome.

By the term "co-administering" and derivatives thereof as used herein refers to either simultaneous administration or any manner of separate sequential administration of a RET inhibiting compound, as described herein, and a further active ingredient or ingredients, particularly those known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of specified cancers in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; DNA methyltransferase inhibitors such as azacitidine and decitabine; signal transduction pathway inhibitors; non-receptor tyrosine kinase angiogenesis inhibitors; immunotherapeutic agents; proapoptotic agents; and cell cycle signaling inhibitors.

Typically, any chemotherapeutic agent that has activity against a susceptible neoplasm being treated may be utilized in combination with the compounds the invention, provided that the particular agent is clinically compatible with therapy employing a compound of the invention. Typical anti-neoplastic agents useful in the present invention include, but are not limited to: alkylating agents, anti-metabolites, anti-tumor antibiotics, antimitotic agents, nucleoside analogues, topoisomerase I and II inhibitors, hormones and hormonal analogues; retinoids, histone deacetylase inhibitors; signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Nucleoside analogues are those compounds which are converted to deoxynucleotide triphosphates and incorporated into replicating DNA in place of cytosine. DNA methyltransferases become covalently bound to the modified bases resulting in an inactive enzyme and reduced DNA methylation. Examples of nucleoside analogues include azacitidine and decitabine which are used for the treatment of myelodysplastic disorder. Histone deacetylase (HDAC) inhibitors include vorinostat, for the treatment of cutaneous T-cell lymphoma. HDACs modify chromatin through the deacetylation of histones. In addition, they have a variety of substrates including numerous transcription factors and signaling molecules. Other HDAC inhibitors are in development.

Signal transduction pathway inhibitors are those inhibitors which block or inhibit a chemical process which evokes an intracellular change. As used herein this change is cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myoinositol signaling, and Ras oncogenes. Signal transduction pathway inhibitors may be employed in combination with the compounds of the invention in the compositions and methods described above.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the compounds of the invention. For example, anti-VEGF antibodies, which do not recognize VEGFR (the receptor tyrosine kinase), but bind to the ligand; small molecule inhibitors of integrin (alpha, beta$_3$) that inhibit angiogenesis; endostatin and angiostatin (non-RTK) may also prove useful in combination with the compounds of the invention. One example of a VEGFR antibody is bevacizumab (AVASTIN®).

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB1 antibody inhibitor of growth factor function is cetuximab (Erbitux™, C225). Bevacizumab (Avastin®) is an example of a monoclonal antibody directed against VEGFR. Examples of small molecule inhibitors of epidermal growth factor receptors include but are not limited to lapatinib (Tykerb®) and erlotinib (TARCEVA®). Imatinib mesylate (GLEEVEC®) is one example of a PDGFR inhibitor. Examples of VEGFR inhibitors include pazopanib (Votrient®), ZD6474, AZD2171, PTK787, sunitinib and sorafenib.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the G$_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325 (1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Int. Med., 111:273,1989) and for the treatment of breast cancer (Holmes et al., J. Nat. Cancer Inst., 83:1797,1991.). It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine N-tert-butyl ester, 13-ester with 5β-20-epoxy-1,2α,4,7β, 10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)-oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl,7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leukopenialeukopenia tends to be more severe than thrombocytopenia.

Teniposide, 4'-demethyl-epipodophyllotoxin 9 [4,6-0-(R)-thenylidene-3-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leukopenialeukopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H)pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leukopenialeukopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leukopenialeukopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leukopenialeukopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leukopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino)carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]

quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

EXPERIMENTALS

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention. Unless otherwise noted, reagents are commercially available or are prepared according to procedures in the literature. The symbols and conventions used in the descriptions of processes, schemes, and examples are consistent with those used in the contemporary scientific literature, for example, the Journal of the American Chemical Society or the Journal of Biological Chemistry.

In the Examples:

Chemical shifts are expressed in parts per million (ppm) units. Coupling constants (J) are in units of hertz (Hz). Splitting patterns describe apparent multiplicities and are designated as s (singlet), d (doublet), t (triplet), q (quartet), dd (double doublet), dt (double triplet), dq (double quartet), m (multiplet), br (broad).

Flash column chromatography was performed on silica gel.

The naming program used was ChemBioDraw® Ultra 12.0.

Abbreviations 18-crown-6 1,4,7,10,13,16-hexaoxacyclooctadecane
CDCl$_3$ chloroform-d
CD$_3$OD methanol-d$_4$
Cs$_2$CO$_3$ cesium carbonate
d day(s)
DCM dichloromethane
DMF N,N-dimethylformamide
EA ethyl acetate
ES-LCMS electrospray liquid chromatography-mass spectrometry
Et$_3$N triethylamine
EtOH ethanol
g gram(s)
h hour(s)
H$_2$ hydrogen gas
HCl hydrochloric acid
H$_2$O water
HPLC high performance liquid chromatography
H$_2$SO$_4$ sulfuric acid
K$_2$CO$_3$ potassium carbonate
KOAc potassium acetate
KOH potassium hydroxide
LCMS liquid chromatography-mass spectrometry
LiOH.H$_2$O lithium hydroxide hydrate
MeCN acetonitrile
MeOH methanol
mg milligram(s)
MgSO$_4$ magnesium sulfate
min minute(s)
mL milliliter(s)
mmol millimole(s)
N$_2$ nitrogen gas
NaCN sodium cyanide
NaHCO$_3$ sodium bicarbonate
NaOH sodium hydroxide
Na$_2$SO$_4$ sodium sulphate
NBS N-bromosuccinimide
NH$_4$OH ammonium hydroxide
NMR nuclear magnetic resonance
Pd/C palladium on carbon
PdCl$_2$(dppf) 1,1'-bis(diphenylphosphino)ferrocene]dichloropalladium(II)
PE petroleum ether
PMB p-methoxybenzyl
rt room temperature
SOCl$_2$ thionyl chloride
TBME tert-butyl methyl ether
TFA trifluoroacetic acid
TLC thin layer chromotrography
T$_3$P® propylphosphonic anhydride Preparation of Intermediates Intermediate 1: 2-(4-(4-Ethoxy-6-((4-methoxybenzyl)oxy)pyridin-3-yl)-2-fluorophenyl)acetic acid

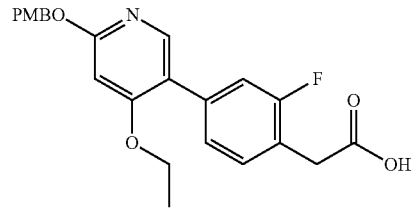

Step 1: 2-Chloro-4-ethoxypyridine

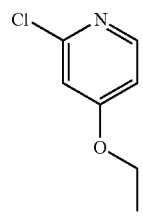

To a mixture of 2-chloro-4-nitropyridine (170 g, 1070 mmol) in THF (2 L) was added sodium ethanolate (109.45 g, 1610 mmol) slowly at 0° C. The mixture was stirred at 25° C. for 12 h. LCMS and TLC analysis (PE/EA=5:1, R$_f$=0.6) showed the reaction was finished. The mixture was filtered, and most of the filtrate solvent was removed by reduced pressure. The mixture was quenched with water and extracted with EA, the organic layer was washed with brine, and then concentrated. Another six batches were prepared following the same procedure to give 2-chloro-4-ethoxypyridine (1100 g, 7.01 mol, 92.4%): $^1$H NMR (400 MHz, CD$_3$OD) δ 8.15 (d, J=6.0 Hz, 1H), 6.99 (d, J=2.0 Hz, 1H), 6.91-6.89 (m, 1H), 4.16-4.14 (m, 2H), 1.41-1.38 (m, 3H); ES-LCMS m/z: 158.1 (M+H).

Step 2: 5-Bromo-2-chloro-4-ethoxypyridine

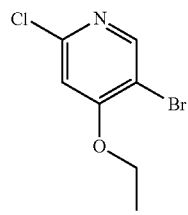

2-Chloro-4-ethoxypyridine (100 g, 634.5 mmol) was added to H$_2$SO$_4$ (500 mL) slowly. NBS (124.2 g, 698.0 mmol) was then added to the above reaction mixture at rt. The mixture was stirred at 80° C. for 3 h. TLC analysis (PE/EA=10:1, R$_f$=0.5) showed the reaction was finished. The reaction mixture was poured into ice-water (2000 mL), extracted with EA, and then concentrated. Another ten batches were prepared following the same procedure. The combined crude product was purified by flash column chromatography to give 5-bromo-2-chloro-4-ethoxypyridine (670 g, 2.84 mol, 40.0%): $^1$H NMR (400 MHz, CD$_3$OD): δ 8.31 (s, 1H), 7.14 (s, 1H), 4.32-4.10 (m, 2H), 1.58-1.35 (m, 3H); ES-LCMS m/z: 236.0, 238.0 (M, M+2H).

Step 3: 5-Bromo-4-ethoxy-2-((4-methoxybenzyl)oxy)pyridine

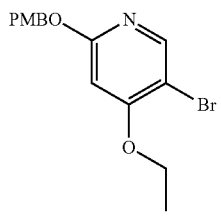

To a mixture of 5-bromo-2-chloro-4-ethoxypyridine (75 g, 317.1 mmol) in toluene (500 mL) was added (4-methoxyphenyl)methanol (52.6 g, 380.6 mmol), KOH (35.6 g, 634.3 mmol) and 18-crown-6 (8.4 g, 31.2 mmol) at rt. The reaction mixture was stirred at 120° C. for 2 h. The mixture was extracted with TBME, washed with brine, and concentrated. Another eight batches were prepared following the same procedure. The combined crude product was purified by flash column chromatography (PE/EA=10:1, R$_f$=0.5) to give 5-bromo-4-ethoxy-2-((4-methoxybenzyl)oxy)pyridine (650 g, 1.99 mol, 70.0%): $^1$H NMR (400 MHz, CD$_3$OD) δ 8.05 (s, 1H), 7.33 (d, J=8.6 Hz, 2H), 6.90-6.84 (m, 2H), 6.38 (s, 1H), 5.20 (s, 2H), 4.16-4.05 (m, 2H), 3.77 (s, 3H), 1.43 (q, J=6.8 Hz, 3H); ES-LCMS m/z: 338.3 (M+2H).

Step 4: 2-(4-Bromo-2-fluorophenyl)acetonitrile

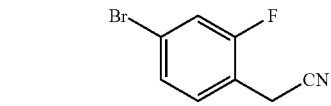

To a solution of 4-bromo-1-(bromomethyl)-2-fluorobenzene (500 g, 1.87 mol) in EtOH (2.2 L) stirred under N$_2$ at 20° C. was added NaCN (93 g, 1.90 mmol) in one charge. The reaction mixture was stirred at 60° C. for 12 h. Then the solution was concentrated and distributed between DCM (2000 mL) and saturated NaHCO$_3$ solution (1800 mL). Another batch was prepared following the same procedure. Then the two batches were combined. The combined organic extract was washed with brine, dried over MgSO$_4$, filtered and concentrated to provide 2-(4-bromo-2-fluorophenyl)acetonitrile (794 g, 99%): $^1$H NMR (400 MHz, CDCl$_3$) δ 7.38-7.27 (m, 3H), 3.72 (s, 2H).

Step 5: 2-(4-Bromo-2-fluorophenyl)acetic acid

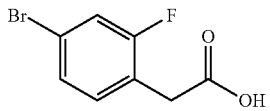 [SMILES: O=C(O)Cc1ccc(Br)cc1F]

To a solution of 2-(4-bromo-2-fluorophenyl)acetonitrile (397 g, 1.82 mol) in MeOH (500 mL) stirred under N$_2$ at 20° C. was added NaOH (2.22 L, 2.5M, 5.56 mol) solution in one charge. The reaction mixture was stirred at 80° C. for 5 h. Then the solution was concentrated and neutralized with conc. HCl to pH=5 with stirring. Then the solution was extracted with EA (1.5 L×2). Another two batches were prepared following the same procedure. Then the three batches were combined. The combined organic extract was washed with brine, dried over Na$_2$SO$_4$, filtered and concentrated in vacuo to give the pure 2-(4-bromo-2-fluorophenyl) acetic acid (1200 g, 92%): TLC (PE/EA=5:1, R$_f$=0.2); $^1$H NMR (400 MHz, CDCl$_3$) δ 7.24 (br. s., 1H), 7.12 (t, J=7.9 Hz, 1H), 3.65 (s, 2H).

Step 6: Methyl 2-(4-bromo-2-fluorophenyl)acetate

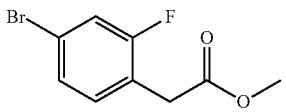

To a solution of 2-(4-bromo-2-fluorophenyl)acetic acid (260 g, 1.13 mol) in MeOH (2 L) was added H$_2$SO$_4$ (30 mL) at rt. The solution was heated to reflux overnight. Then the solvent was concentrated and the residue was distributed between EA and saturated NaHCO$_3$ solution. The organic extract was washed with brine, dried over Na$_2$SO$_4$, filtered and concentrated. Another batch was prepared following the same procedure. Then the two batches were combined to provide methyl 2-(4-bromo-2-fluorophenyl)acetate (520 g, 94%). TLC (PE/EA=10:1, R$_f$=0.7). $^1$H NMR (400 MHz, CDCl$_3$) δ 7.25-7.20 (m, 2H), 7.14 (t, J=8.0 Hz, 1H), 3.70 (s, 3H), 3.62 (s, 2H).

Step 7: Methyl 2-(2-fluoro-4-(4,4,5,5-tetramethyl-1,3,2-dioxaborolan-2-yl)phenyl)acetate

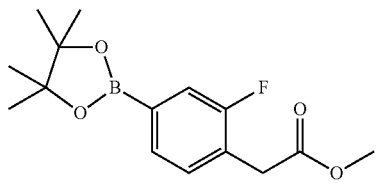

To a solution of methyl 2-(4-bromo-2-fluorophenyl)acetate (260 g, 1.05 mol) and 4,4,4',4',5,5,5',5'-octamethyl-2,2'-bi(1,3,2-dioxaborolane) (320 g, 1.26 mol) in 1,4-dioxane (2 L) was added KOAc (206 g, 2.10 mol) and PdCl$_2$(dppf) (23 g, 0.03 mol) at rt. The solution was heated to reflux for 4 h under N$_2$. Then the solution was filtered and the filtrate was concentrated in vacuo to give the crude product. Another batch was prepared following the same procedure. Then the two batches were combined and purified by flash column chromatography (PE/EA=30:1 to 10:1). All fractions found to contain product by TLC (PE/EA=10:1, R$_f$=0.5) were combined and concentrated to yield methyl 2-(2-fluoro-4-(4,4,5,5-tetramethyl-1,3,2-dioxaborolan-2-yl)phenyl)acetate (560 g, 90%) as a light yellow oil: $^1$H NMR (400 MHz, CDCl$_3$) δ 7.54 (d, J=7.5 Hz, 1H), 7.49 (d, J=10.0 Hz, 1H), 7.31-7.26 (m, 1H), 3.73 (s, 2H), 1.34 (s, 12H), 1.27 (s, 3H); ES-LCMS m/z 295.2 (M+H).

Step 8: Methyl 2-(4-(4-ethoxy-6-((4-methoxybenzyl)oxy)pyridin-3-yl)-2-fluorophenyl)acetate

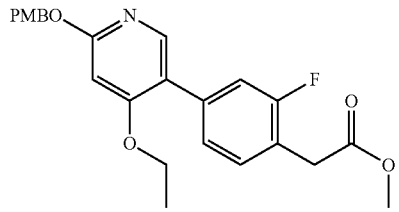

To a solution of 5-bromo-4-ethoxy-2-((4-methoxybenzyl)oxy)pyridine (175 g, 519 mmol) in 1,4-dioxane (1200 mL) and H$_2$O (300 mL) was added methyl 2-(2-fluoro-4-(4,4,5,5-tetramethyl-1,3,2-dioxaborolan-2-yl)phenyl)acetate (167 g, 569 mmol), PdCl$_2$(dppf) (25 g, 5.19 mmol) and Cs$_2$CO$_3$ (337 g, 1038 mmol) under a N$_2$ atmosphere. The mixture was refluxed for 2 h. TLC analysis (PE/EA=5:1, R$_f$=0.3) showed the reaction was finished. The mixture was extracted with EA/H$_2$O (2 L) to give the oil layer, which was dried over Na$_2$SO$_4$, filtered, concentrated. Another two batches were prepared following the same procedure. The combined crude product was purified by flash column chromatography (PE/EA=5:1, R$_f$=0.3) to give 5-bromo-4-ethoxy-2-((4-methoxybenzyl)oxy)pyridine (630 g, 1.48 mol, 90.0%): $^1$H NMR (400 MHz, CD$_3$OD) δ 7.94 (s, 1H), 7.36 (d, J=8.8 Hz, 2H), 7.32-7.22 (m, 3H), 6.90 (d, J=8.8 Hz, 2H), 6.43 (s, 1H), 5.26 (s, 2H), 4.11 (d, J=6.8 Hz, 2H), 3.78 (s, 3H), 3.72 (s, 2H), 3.70 (s, 3H), 1.36 (t, J=7.0 Hz, 3H); ES-LCMS m/z: 426.1 (M+H).

Step 9: 2-(4-(4-Ethoxy-6-((4-methoxybenzyl)oxy)pyridin-3-yl)-2-fluorophenyl)acetic acid

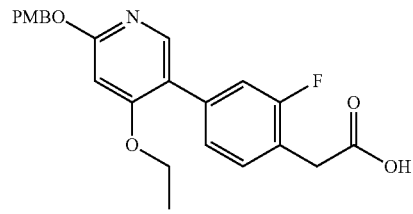

To a solution of methyl 2-(4-(4-ethoxy-6-((4-methoxybenzyl)oxy)pyridin-3-yl)-2-fluorophenyl)acetate (210 g, 519 mmol) in THF (500 mL) was added LiOH.H$_2$O (52 g, 1230 mmol) in H$_2$O (700 mL). The mixture was stirred at 60° C. overnight. TLC analysis (PE/EA=5:1, Rf=0.3) showed the reaction was finished. The mixture was concentrated, and adjusted with HCl (1 N) to pH=7. Another two batches were prepared following the same procedure. Then the combined crude product was filtered, the solid was washed with water and dried to give 2-(4-(4-ethoxy-6-((4-methoxybenzyl)oxy)pyridin-3-yl)-2-fluorophenyl)acetic acid (550 g, 1.34 mol, 93.0%): $^1$H NMR (400 MHz, CD$_3$OD): δ 7.94 (s, 1H), 7.41-7.28 (m, 3H), 7.24 (d, J=9.5 Hz, 2H), 6.91 (d, J=8.6 Hz, 2H), 6.44 (s, 1H), 5.26 (s, 2H), 4.11 (q, J=6.9 Hz, 2H), 3.78 (s, 3H), 3.67 (s, 2H), 1.36 (t, J=7.0 Hz, 3H); ES-LCMS m/z: 412.1 (M+H).

Preparation of Compounds of the Invention

Example 1: N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide

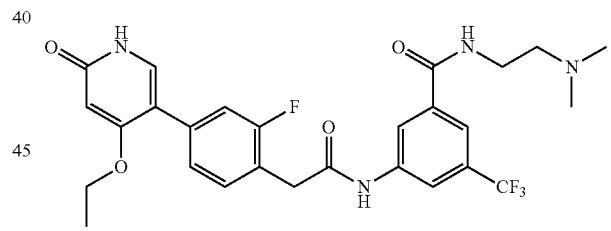

Step 1: 3-Nitro-5-(trifluoromethyl)benzoic acid

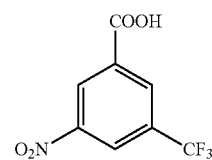 [SMILES: O=C(O)c1cc([N+](=O)[O-])cc(C(F)(F)F)c1]

To a mixture of 3-(trifluoromethyl)benzoic acid (5 g, 26.3 mmol) in H$_2$SO$_4$ (50 mL, 938 mmol) was added nitric acid (3.53 mL, 79 mmol). The mixture was stirred at 0° C. for 15 min and warmed to 90° C. over 1 h. Then the mixture was added to ice water dropwise. The mixture was filtered to give a white solid of 3-nitro-5-(trifluoromethyl)benzoic acid (5.2 g, 21.01 mmol, 80.0%): $^1$H NMR (400 MHz, CD$_3$OD) δ 8.99 (s, 1H), 8.72 (s, 1H), 8.61 (s, 1H).

Step 2: N-(2-(dimethylamino)ethyl)-3-nitro-5-(trifluoromethyl)benzamide

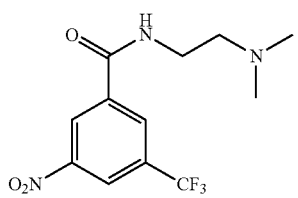

A mixture of 3-nitro-5-(trifluoromethyl)benzoic acid (3.3 g, 14.04 mmol) in SOCl$_2$ (50 mL, 685 mmol) and DMF (0.5 mL, 6.46 mmol) was stirred at 75° C. for 2 h. Then the mixture was concentrated, and the acid chloride was dissolved in DCM (50 mL). The mixture cooled to 0° C. and then was added Et$_3$N (2.348 mL, 16.84 mmol) followed by N$^1$,N$^1$-dimethylethane-1,2-diamine (0.740 mL, 15.44 mmol). The reaction was stirred at 0° C. for 30 min and the mixture was then concentrated. The crude material was purified by flash column chromatography (DCM/MeOH=15:1). All fractions found to contain product by TLC (DCM/MeOH=15:1, R$_f$=0.3) were combined and concentrated to yield a yellow oil of N-(2-(dimethylamino)ethyl)-3-nitro-5-(trifluoromethyl)benzamide (5 g, 8.19 mmol, 58.4%): $^1$H NMR (400 MHz, CD$_3$OD) δ 9.00 (s, 1H), 8.65 (s, 1H), 8.61 (s, 1H), 3.86 (t, J=6.0 Hz, 2H), 3.42 (t, J=6.0 Hz, 2H), 2.99 (s, 6H); ES-LCMS m/z 306.1 (M+H).

Step 3: 3-Amino-N-(2-(dimethylamino)ethyl)-5-(trifluoromethyl)benzamide dihydrochloride

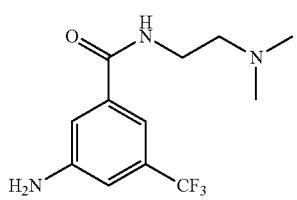 [SMILES: CN(C)CCNC(=O)c1cc([N+](=O)[O-])cc(C(F)(F)F)c1]

To a mixture of N-(2-(dimethylamino)ethyl)-3-nitro-5-(trifluoromethyl)benzamide (5 g, 8.19 mmol) in MeOH (100 mL) was added Pd/C (500 mg, 10%). The mixture was stirred at 10° C. for 16 h under a H$_2$ atmosphere. Then the mixture was filtered and concentrated. The crude material was purified by preparative HPLC (Column: ASB C18 150*25 mm; Mobile phase A: H$_2$O+0.1% HCl; Mobile phase B: MeCN; Flowrate: 25 mL/min; Gradient Profile Description: 5-35 (B %)) to yield an off-white solid of 3-amino-N-(2-(dimethylamino)ethyl)-5-(trifluoromethyl)benzamide dihydrochloride (878.01 mg, 2.52 mmol, 30.8%): $^1$H NMR (400 MHz, CD$_3$OD) δ 8.28 (s, 1H), 8.19 (s, 1H), 7.86 (s, 1H), 3.84 (t, J=6.0 Hz, 2H), 3.47 (t, J=6.0 Hz, 2H), 3.02 (s, 6H); ES-LCMS m/z 276.1 (M+H).

Step 4: N-(2-(dimethylamino)ethyl)-3-(3-(2-(5-ethoxy-6-((4-methoxybenzyl)oxy)pyridine-3-yl)-4-methylpyrimidin-5-yl)ureido)-5-(trifluoromethyl)benzamide

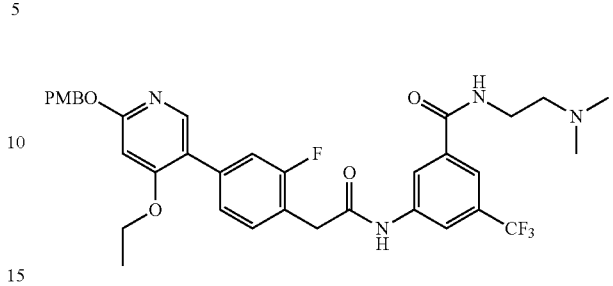

To a mixture of 2-(4-(4-ethoxy-6-((4-methoxybenzyl)oxy)pyridin-3-yl)-2-fluorophenyl)acetic acid (100 mg, 0.243 mmol) in pyridine (3 mL) were added 3-amino-N-(2-(dimethylamino)ethyl)-5-(trifluoromethyl)benzamide (66.9 mg, 0.243 mmol) and T$_3$P® (0.8 mL, 0.243 mmol, 50% in EA). The mixture was stirred at 10° C. for 16 h. The mixture was concentrated. The crude material was purified by preparative TLC (DCM/MeOH=10:1, R$_f$=0.3) to yield a yellow solid of N-(2-(dimethylamino)ethyl)-3-(2-(4-(4-ethoxy-6-((4-methoxybenzyl)oxy)pyridin-3-yl)-2-fluorophenyl)acetamido)-5-(trifluoromethyl)benzamide (80 mg, 0.096 mmol, 39.4%): $^1$H NMR (400 MHz, CD$_3$OD): δ 8.55 (d, J=4.4 Hz, 1H), 8.43 (s, 1H), 8.06 (s, 1H), 7.96 (s, 1H), 7.89 (s, 1H), 7.48-7.45 (m, 1H), 7.36 (d, J=8.8 Hz, 2H), 7.29 (s, 1H), 6.90 (d, J=8.8 Hz, 2H), 6.45 (s, 1H), 5.26 (s, 2H), 4.12 (q, J=7.2 Hz, 2H), 3.84 (s, 2H), 3.78 (s, 3H), 3.76 (t, J=2.4 Hz, 2H), 3.37 (t, J=5.6 Hz, 2H), 2.97 (s, 6H), 1.36 (t, J=7.2 Hz, 3H); ES-LCMS m/z 669.1 (M+H).

Step 5: N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide

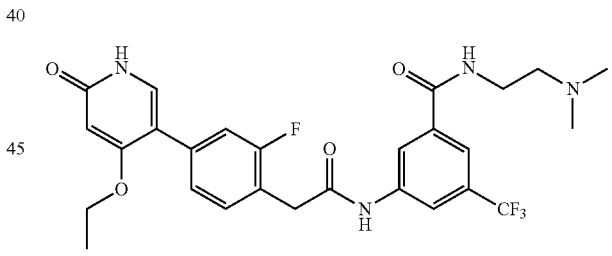

To a mixture of N-(2-(dimethylamino)ethyl)-3-(2-(4-(4-ethoxy-6-((4-methoxybenzyl) oxy)pyridin-3-yl)-2-fluorophenyl)acetamido)-5-(trifluoromethyl)benzamide (80 mg, 0.120 mmol) in DCM (20 mL) was added TFA (2 mL, 26.0 mmol). The mixture was stirred at 25° C. for 2 h. Then the reaction was concentrated and basified with NH$_4$OH. The crude material was purified by preparative HPLC (Instrument: Gilson GX281; Column: Gemini 150*25 mm*5 um; Mobile phase A: H$_2$O (0.05% ammonia solution); Mobile phase B: MeCN; Gradient: 25-55(B %); Flowrate: 25 mL/min; Run time: 10 min) to yield an white solid of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide (27.71 mg, 0.050 mmol, 41.8%): TLC (DCM/MeOH=10:1, Rf=0.2) $^1$H NMR (400 MHz, CD$_3$OD): δ 8.26 (s, 1H), 8.20 (s, 1H), 7.90 (s, 1H), 7.45-7.39 (m, 2H), 7.29-7.23 (m, 2H), 6.02 (s, 1H), 4.14 (q, J=7.2 Hz, 2H), 3.86 (s, 2H), 3.57 (t, J=6.4 Hz, 2H), 2.63 (t, J=6.8 Hz, 2H), 2.36 (s, 6H), 1.40 (t, J=7.2 Hz, 3H); ES-LCMS m/z 549.2 (M+H).

Example 2: N-(3-(2-(dimethylamino)ethoxy)-5-(trifluoromethyl)phenyl)-2-(4-(4-ethoxy-6-oxo-1,6-dihydropyridin-3-yl)-2-fluorophenyl)acetamide

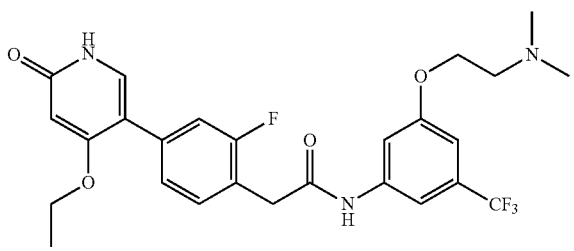 [SMILES: CCOc1cc(=O)[nH]cc1-c1ccc(CC(=O)Nc2cc(OCCN(C)C)cc(C(F)(F)F)c2)c(F)c1]

Step 1: N,N-dimethyl-2-(3-nitro-5-(trifluoromethyl)phenoxy)ethanamine

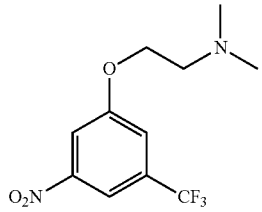 [SMILES: CN(C)CCOc1cc([N+](=O)[O-])cc(C(F)(F)F)c1]

To a suspension of 1-fluoro-3-nitro-5-(trifluoromethyl)benzene (2 g, 9.56 mmol) in DMF (15 mL) were added 2-(dimethylamino)ethanol (2.56 g, 28.7 mmol) and $K_2CO_3$ (2.64 g, 19.13 mmol). The mixture was stirred at 80° C. for 8 h. The mixture was cooled to rt. Then the solution was concentrated and distributed between EA (10 mL) and a saturated $NaHCO_3$ solution (10 mL). The organic extract was washed with brine (10 mL), dried over $MgSO_4$, filtered, and concentrated. The crude material was purified by flash column chromatography (PE/EA=1:1). All fractions found to contain product by TLC (PE/EA=1:1, $R_f$=0.5) were combined and concentrated to yield a light yellow solid of N,N-dimethyl-2-(3-nitro-5-(trifluoromethyl)phenoxy)ethanamine (1.8 g, 5.18 mmol, 54.1%): $^1$H NMR (400 MHz, $CDCl_3$) δ 8.07 (s, 1H), 7.94 (s, 1H), 7.50 (s, 1H), 4.18 (t, J=5.4 Hz, 2H), 2.79 (t, J=5.4 Hz, 2H), 2.36 (s, 6H); ES-LCMS m/z 279.0 (M+H).

Step 2: 3-(2-(Dimethylamino)ethoxy)-5-(trifluoromethyl)aniline

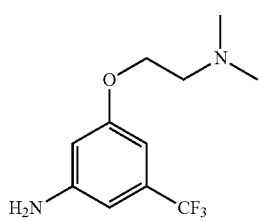

To a suspension of N,N-dimethyl-2-(3-nitro-5-(trifluoromethyl)phenoxy)ethanamine (1.8 g, 6.47 mmol) in MeOH (20 mL) was added Pd/C (0.344 g, 10%). The mixture was hydrogenated under a $H_2$ atmosphere at 15 Psi at 26° C. for 3 h. Then the solution was filtered and concentrated. The crude material was purified by flash column chromatography (PE/EA=1:1). All fractions found to contain product by TLC (PE/EA=1:1, $R_f$=0.4) were combined and concentrated to yield a light yellow solid of 3-(2-(dimethylamino)ethoxy)-5-(trifluoromethyl)aniline (1 g, 3.54 mmol, 54.7%): $^1$H NMR (400 MHz, $CD_3OD$) δ 6.53 (d, J=16.8 Hz, 2H), 6.38 (s, 1H), 4.05 (t, J=5.6 Hz, 2H), 2.75-2.70 (m, 2H), 2.35-2.32 (m, 6H); ES-LCMS m/z 249.1 (M+H).

Step 3: N-(3-(2-(dimethylamino)ethoxy)-5-(trifluoromethyl)phenyl)-2-(4-(4-ethoxy-6-((4-methoxybenzyl)oxy)pyridin-3-yl)-2-fluorophenyl)acetamide

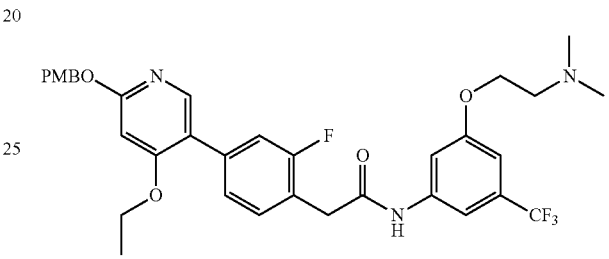

To a solution of 2-(4-(4-ethoxy-6-((4-methoxybenzyl)oxy)pyridin-3-yl)-2-fluorophenyl)acetic acid (400 mg, 0.972 mmol) and 3-(2-(dimethylamino)ethoxy)-5-(trifluoromethyl)aniline (241 mg, 0.972 mmol) in pyridine (8 mL) was added $T_3P$® (4 mL, 0.972 mmol) at 27° C. under a $N_2$ atmosphere. The mixture was stirred at 27° C. for 30 min. LCMS showed the reaction was completed. Then the mixture was put into ice (1 g). The mixture was concentrated to a residue that was purified by preparative TLC (DCM/MeOH=10:1, $R_f$=0.6) to yield a light yellow solid of N-(3-(2-(dimethylamino)ethoxy)-5-(trifluoromethyl)phenyl)-2-(4-(4-ethoxy-6-((4-methoxybenzyl)oxy)pyridin-3-yl)-2-fluorophenyl)acetamide (300 mg, 0.421 mmol, 43.3%): $^1$H NMR (400 MHz, $CD_3OD$) δ 7.96 (s, 1H), 7.75-7.68 (m, 1H), 7.52 (s, 1H), 7.38 (d, J=8.4 Hz, 2H), 7.32-7.24 (m, 3H), 7.05 (s, 1H), 6.92 (d, J=8.6 Hz, 2H), 6.45 (s, 1H), 5.27 (s, 2H), 4.43-4.36 (m, 2H), 4.12 (q, J=6.8 Hz, 2H), 3.83 (s, 2H), 3.82-3.77 (m, 3H), 3.60-3.51 (m, 2H), 2.93 (s, 6H), 1.37 (t, J=6.9 Hz, 3H); ES-LCMS m/z 642.2 (M+H).

Step 4: N-(3-(2-(dimethylamino)ethoxy)-5-(trifluoromethyl)phenyl)-2-(4-(4-ethoxy-6-oxo-1,6-dihydropyridin-3-yl)-2-fluorophenyl)acetamide

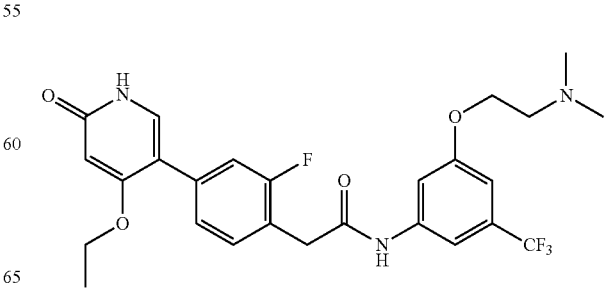

To a suspension of N-(3-(2-(dimethylamino)ethoxy)-5-(trifluoromethyl)phenyl)-2-(4-(4-ethoxy-6-((4-methoxybenzyl)oxy)pyridin-3-yl)-2-fluorophenyl)acetamide (300 mg, 0.468 mmol) in MeOH (10 mL) was added Pd/C (49.8 mg, 10%). The mixture was hydrogenated under a $H_2$ atmosphere at 25° C. for 3 h. Then the reaction was filtered and concentrated to a residue that was purified by preparative HPLC (Instrument: Gilson GX281/Column: Gemini 150*25 mm*5 um/Mobile phase A: $H_2O$ (0.05% ammonia solution)/Mobile phase B: MeCN/Gradient: 40-70(B %)/Flowrate: 25 mL/min/Run time: 10 min) to yield a white solid of N-(3-(2-(dimethylamino)ethoxy)-5-(trifluoromethyl)phenyl)-2-(4-(4-ethoxy-6-oxo-1,6-dihydropyridin-3-yl)-2-fluorophenyl)acetamide (54.34 mg, 0.104 mmol, 22.2%): $^1$H NMR (400 MHz, $CD_3OD$) δ 7.52 (d, J=9.9 Hz, 2H), 7.43-7.31 (m, 2H), 7.27-7.17 (m, 2H), 6.95 (s, 1H), 5.99 (s, 1H), 4.21-4.04 (m, 4H), 3.80 (s, 2H), 2.79 (t, J=5.3 Hz, 2H), 2.35 (s, 6H), 1.38 (t, J=7.1 Hz, 3H); ES-LCMS m/z 522.2 (M+H).

Example 3: N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride, hydrate 1

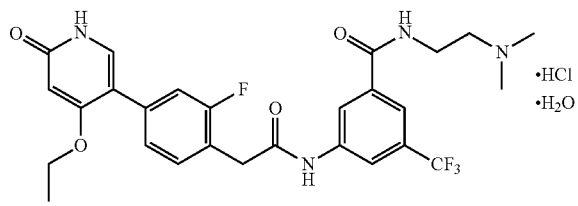

A suspension of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide (350 mg) in 8.4 mL of acetone:water (9:1, v/v) was stirred for 15 min at 23° C. HCl (5M solution in water, 1.0 equivalent) was added and the sample was heated to 40° C. The sample was stirred and temperature-cycled between 40° C. and 5° C. for 24 h and then stirred at 20° C. for 0.5 h. The solids were isolated by vacuum filtration and dried in a vacuum oven at 40° C. for at least 16 hours to give the title compound as a crystalline solid.

Alternative Procedure

A slurry of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride, anhydrate (500 mg) in water (12 mL) was temperature-cycled between 40° C. and 5° C. over 2 d. The sample was harvested by filtration and dried to give the title compound as a crystalline solid.

The X-ray powder diffraction (XRPD) pattern of this material (hydrate 1 of the hydrochloric acid salt of the compound of Formula (I)) is shown in FIG. 1 and a summary of the diffraction angles and d-spacings is given in Table I below. The XRPD analysis was conducted on a PANanalytical X'Pert Pro Diffractometer on Si zero-background wafers. The acquisition conditions included: Cu $K_α$ radiation, generator tension: 45 kV, generator current: 40 mA, step size: 0.02° 2θ.

TABLE I

| Diff. Angle [°2θ] | d-spacing [Å] |
|---|---|
| 5.9586 | 14.8328 |
| 6.0888 | 14.51589 |
| 9.013 | 9.81187 |
| 9.2437 | 9.56744 |
| 11.7804 | 7.51235 |
| 11.8888 | 7.44413 |
| 12.1494 | 7.28502 |
| 13.3294 | 6.64266 |
| 13.4351 | 6.59061 |
| 13.5841 | 6.51868 |
| 13.9743 | 6.33752 |
| 14.84 | 5.96474 |
| 14.9038 | 5.94426 |
| 15.337 | 5.77733 |
| 20.4737 | 4.33798 |
| 22.2237 | 3.99688 |
| 22.2822 | 3.98652 |
| 24.4687 | 3.63501 |
| 24.6344 | 3.61095 |
| 24.9574 | 3.56494 |
| 25.0988 | 3.54517 |
| 25.177 | 3.53434 |

Figure 2:
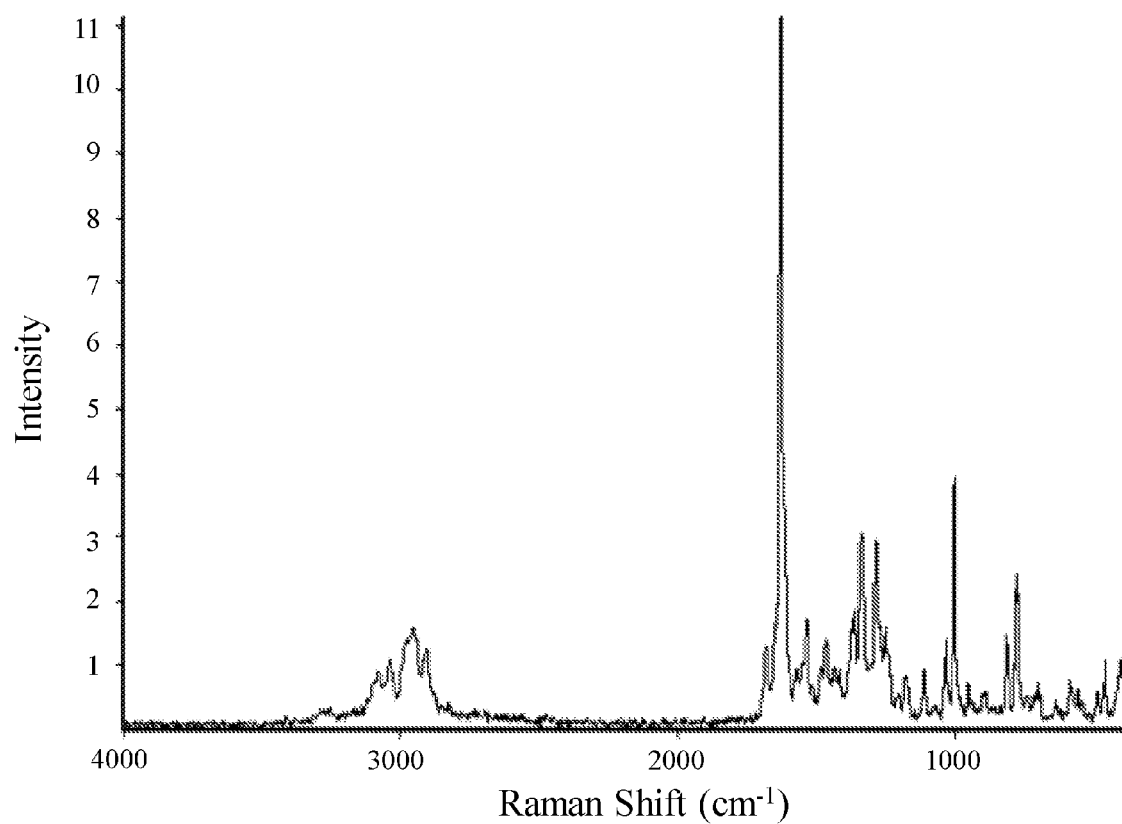
FIG. 2 shows a Raman spectrum of hydrate 1 of the hydrochloric acid salt of the compound of Formula (I).

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of this material is shown in FIG. 2 with major peaks observed at 455.6, 581.0, 697.7, 773.5, 809.3, 951.5, 999.3, 1029.7, 1109.3, 1172.1, 1247.8, 1282.4, 1334.7, 1361.6, 1461.3, 1531.6, 1626.3, 1677.7, 2902.7, 2951.6, and 3032.8 cm$^{-1}$.

The differential scanning calorimetry (DSC) thermogram of the title compound was recorded on a TA Instruments Q100 Differential Scanning Calorimeter equipped with an autosampler and a refrigerated cooling system under 40 mL/min $N_2$ purge and is shown in FIG. 3. The experiments were conducted using a heating rate of 15° C./min in a crimped aluminum pan. The DSC thermogram of hydrate 1 of the hydrochloric acid salt of the compound of Formula (I) exhibited a first endotherm with an onset temperature of about 32° C., a peak temperature about 74° C., and enthalpy of 44.07 J/g, followed by a second endotherm with an onset temperature of about 158° C., a peak temperature about 173° C., and enthalpy of 55.24 J/g. A person skilled in the art would recognize that the onset temperature, peak temperature, and enthalpy of the endotherm may vary depending on the experimental conditions.

The thermogravimetric analysis (TGA) thermogram of the title compound was recorded on a TA Instruments Q500 Thermogravimetric Analyzer and is shown in FIG. 4. The experiments were conducted with 40 mL/min $N_2$ flow and a heating rate of 15° C./min. The TGA thermogram of hydrate 1 of the hydrochloric acid salt of the compound of Formula (I) exhibited two steps of weight loss events observed prior to the final thermal decomposition. The first weight loss event takes place in the temperature range of 30° C. to 100° C. with a weight loss of 1.52%. The second weight loss event takes place in the temperature range of 100° C. to 200° C. with a weight loss of 2.57%.

Example 4: N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride, hydrate 2

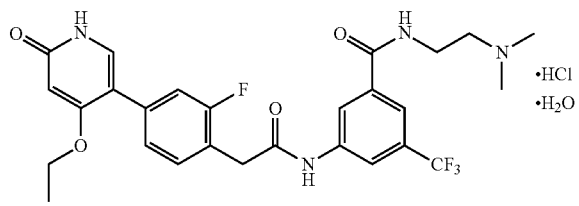

A suspension of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride, hydrate 1 (39.1 mg) in 1 mL of acetone:water (9:1, v/v) was stirred and temperature-cycled between 40° C. and 5° C. for 3 d. The filtrate is then evaporated at room temperature for seven days to give the title compound as a crystalline solid.

Figure 5:
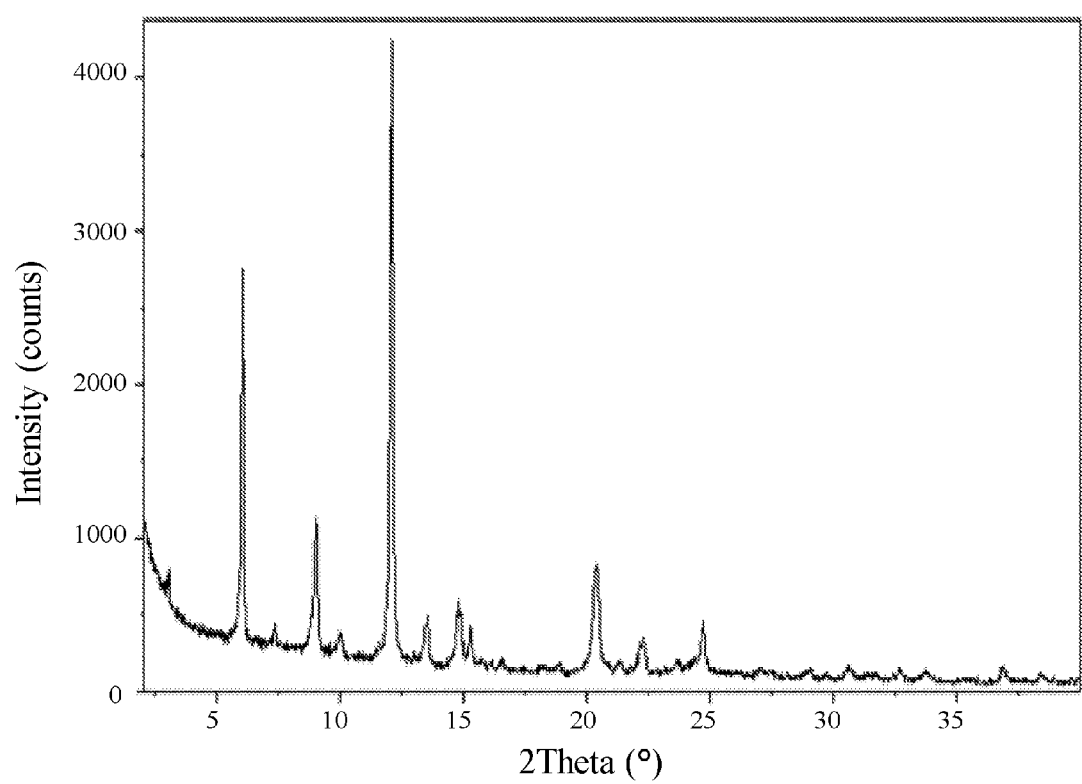
FIG. 5 shows an X-ray powder diffraction pattern of hydrate 2 of the hydrochloric acid salt of the compound of Formula (I).

The X-ray powder diffraction (XRPD) pattern of this material (hydrate 2 of the hydrochloric acid salt of the compound of Formula (I)) is shown in FIG. 5 and a summary of the diffraction angles and d-spacings is given in Table II below. The XRPD analysis was conducted on a PANanalytical X'Pert Pro Diffractometer on Si zero-background wafers. The acquisition conditions included: Cu $K_\alpha$ radiation, generator tension: 45 kV, generator current: 40 mA, step size: 0.02° 2θ.

TABLE II

| Diff. Angle [°2θ] | d-spacing [Å] |
|---|---|
| 6.0237 | 14.67257 |
| 8.9915 | 9.83523 |
| 12.0697 | 7.33295 |
| 13.4151 | 6.60039 |
| 13.518 | 6.55036 |
| 14.7032 | 6.01993 |
| 14.7622 | 6.00096 |
| 14.8596 | 5.96186 |
| 15.2698 | 5.80263 |
| 20.2834 | 4.37464 |
| 20.3721 | 4.35939 |
| 22.1624 | 4.01112 |
| 22.2749 | 3.9878 |
| 22.3759 | 3.97991 |
| 24.7082 | 3.60033 |
| 24.7704 | 3.60035 |

Figure 6:
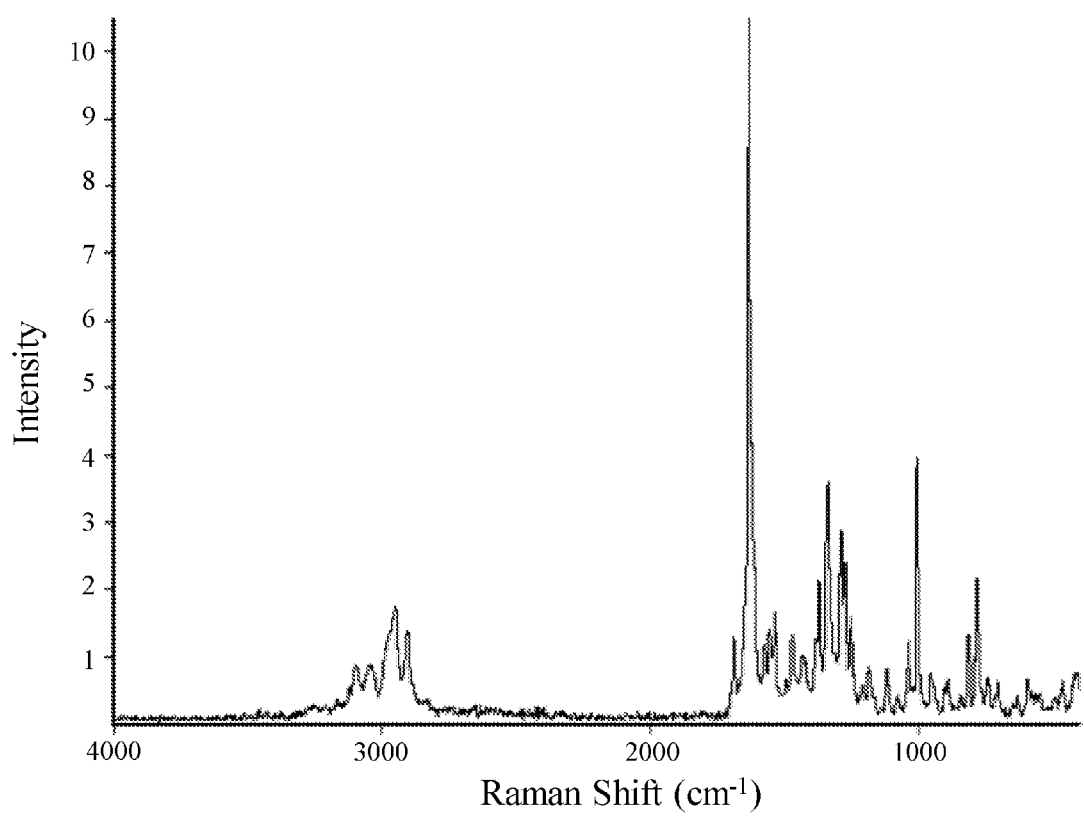
FIG. 6 shows a Raman spectrum of hydrate 2 of the hydrochloric acid salt of the compound of Formula (I).

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of this material is shown in FIG. 6 with major peaks observed at 455.3, 588.2, 699.4, 734.2, 775.3, 806.8, 884.7, 948.6, 1000.0, 1033.3, 1112.3, 1180.6, 1247.3, 1269.2, 1282.5, 1331.8, 1365.7, 1424.7, 1466.3, 1530.0, 1549.9, 1569.7, 1627.3, 1683.8, 2901.8, 2946.4, and 3044.2 cm$^{-1}$.

The differential scanning calorimetry (DSC) thermogram of the title compound was recorded on a TA Instruments Q100 Differential Scanning Calorimeter equipped with an autosampler and a refrigerated cooling system under 40 mL/min N$_2$ purge and is shown in FIG. 7. The experiments were conducted using a heating rate of 15° C./min in a crimped aluminum pan. The DSC thermogram of hydrate 2 of the hydrochloric acid salt of the compound of Formula (I) exhibited a first endotherm with an onset temperature of about 66° C., a peak temperature about 82° C., and enthalpy of 26.177 J/g, followed by a second endotherm with an onset temperature of about 166° C., a peak temperature about 181° C., and enthalpy of 65.71 J/g. A person skilled in the art would recognize that the onset temperature, peak temperature, and enthalpy of the endotherm may vary depending on the experimental conditions.

The thermogravimetric analysis (TGA) thermogram of the title compound was recorded on a TA Instruments Q500 Thermogravimetric Analyzer and is shown in FIG. 8. The experiments were conducted with 40 mL/min N$_2$ flow and a heating rate of 15° C./min. The TGA thermogram of hydrate 2 of the hydrochloric acid salt of the compound of Formula (I) exhibited two steps of weight loss events observed prior to the final thermal decomposition. The first weight loss event takes place in the temperature range of 30° C. to 100° C. with a weight loss of 2.43%. The second weight loss event takes place in the temperature range of 100° C. to 220° C. with a weight loss of 3.29%.

Example 5: N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride, anhydrate

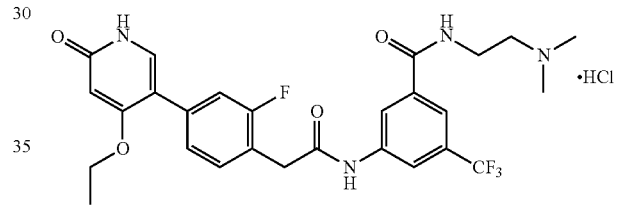

A slurry of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hydrochloride, hydrate 1 (500 mg) in 12.5 mL of EtOH was stirred and temperature-cycled between 40° C. and 5° C. for 1 d. The sample was harvested by filtration and air-dried for a minimum of 1 h to give the title compound as a crystalline solid.

Figure 9:
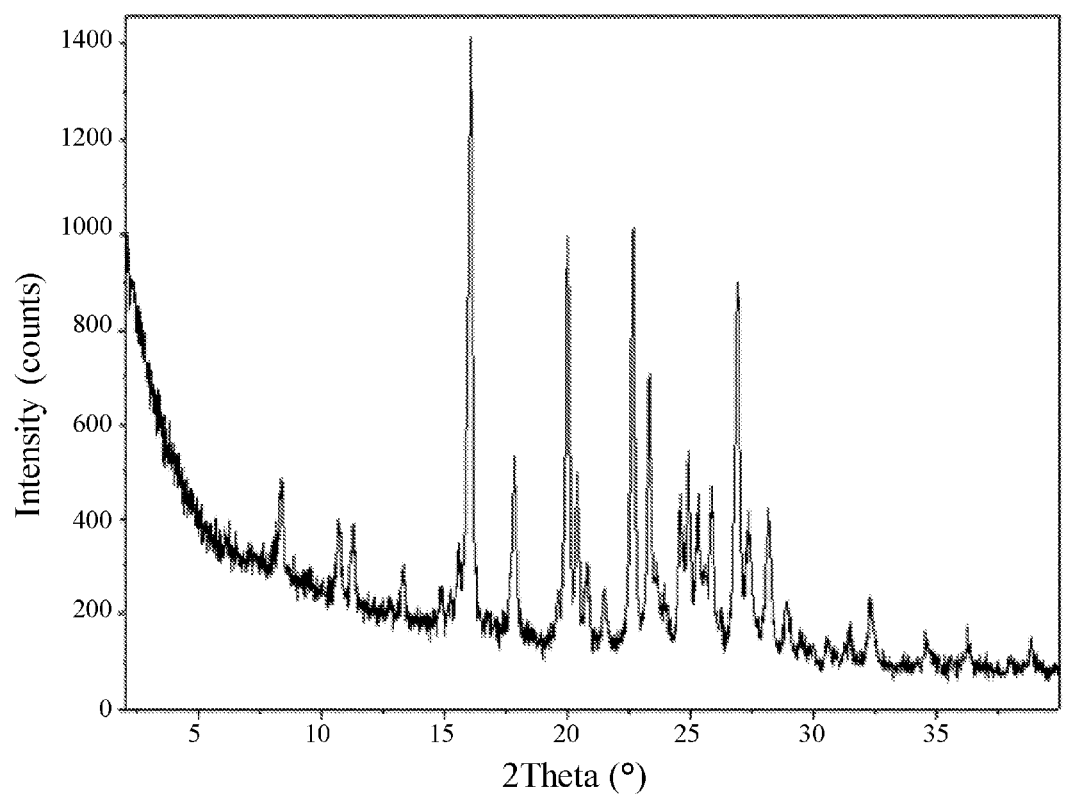
FIG. 9 shows an X-ray powder diffraction pattern of the anhydrous hydrochloric acid salt of the compound of Formula (I).

The X-ray powder diffraction (XRPD) pattern of this material (the anhydrous hydrochloric acid salt of the compound of Formula (I)) is shown in FIG. 9 and a summary of the diffraction angles and d-spacings is given in Table III below. The XRPD analysis was conducted on a PANanalytical X'Pert Pro Diffractometer on Si zero-background wafers. The acquisition conditions included: Cu $K_\alpha$ radiation, generator tension: 45 kV, generator current: 40 mA, step size: 0.02° 2θ.

TABLE III

| Diff. Angle [°2θ] | d-spacing [Å] |
|---|---|
| 8.2804 | 10.67826 |
| 8.3585 | 10.57856 |
| 10.6756 | 8.28718 |
| 11.2515 | 7.86431 |
| 15.529 | 5.70635 |
| 16.0376 | 5.52652 |
| 19.9806 | 4.44392 |
| 20.3778 | 4.35818 |
| 20.7946 | 4.27176 |

TABLE III-continued

| Diff. Angle [°2θ] | d-spacing [Å] |
|---|---|
| 22.6327 | 3.92883 |
| 23.2278 | 3.82633 |
| 23.3175 | 3.81497 |
| 23.6252 | 3.76597 |
| 24.5698 | 3.62028 |
| 24.6174 | 3.62238 |
| 24.902 | 3.57274 |
| 25.2799 | 3.52018 |
| 25.8512 | 3.44367 |
| 26.8957 | 3.31225 |
| 27.2572 | 3.26914 |
| 27.3858 | 3.25408 |
| 28.0514 | 3.17837 |
| 28.1463 | 3.16786 |
| 28.2384 | 3.16559 |

Figure 10:
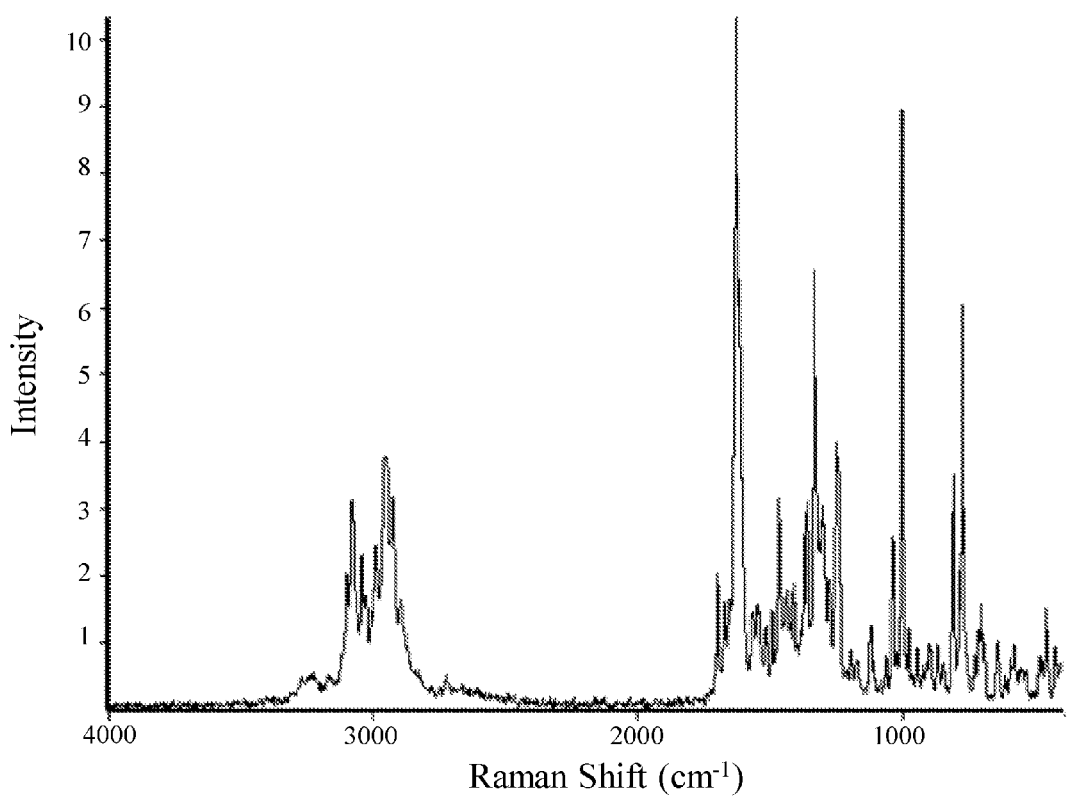
FIG. 10 shows a Raman spectrum of the anhydrate of the anhydrous hydrochloric acid salt of the compound of Formula (I).

The Raman spectrum of the title compound was recorded on a Nicolet NXR 9650 FT-Raman Spectrometer, at 4 cm$^{-1}$ resolution with excitation from a Nd:YVO4 laser ($\lambda$=1064 nm). The Raman spectrum of this material is shown in FIG. 10 with major peaks observed at 418.4, 453.5, 575.3, 635.8, 699.3, 771.0, 782.0, 805.0, 863.9, 893.8, 940.5, 974.2, 997.9, 1058.1, 1115.8, 1190.2, 1245.9, 1272.8, 1299.2, 1328.5, 1355.7, 1406.8, 1433.1, 1462.1, 1489.0, 1511.0, 1546.3, 1562.1, 1614.1, 1625.9, 1666.7, 1695.0, 2921.9, 2950.2, 2986.2, 3036.1, 3075.0, and 3095.0 cm$^{-1}$.

The differential scanning calorimetry (DSC) thermogram of the title compound was recorded on a TA Instruments Q100 Differential Scanning Calorimeter equipped with an autosampler and a refrigerated cooling system under 40 mL/min N$_2$ purge and is shown in FIG. 11. The experiments were conducted using a heating rate of 15° C./min in a crimped aluminum pan. The DSC thermogram of the anhydrous hydrochloric acid salt of the compound of Formula (I) exhibited a sharp endotherm with an onset temperature of 256.44° C., a peak temperature about 258.48° C., and enthalpy of 128.0 J/g. A person skilled in the art would recognize that the onset temperature, peak temperature, and enthalpy of the endotherm may vary depending on the experimental conditions.

The thermogravimetric analysis (TGA) thermogram of the title compound was recorded on a TA Instruments Q500 Thermogravimetric Analyzer and is shown in FIG. 12. The experiments were conducted with 40 mL/min N$_2$ flow and a heating rate of 15° C./min. The TGA thermogram of the anhydrous hydrochloric acid salt of the compound of Formula (I) exhibited negligible weight loss in the temperature range of 25° C. to 150° C. and a thermal decomposition onset temperature of 267.33° C.

Example 6: N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide aspartate

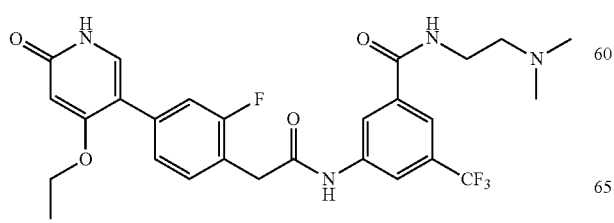 [SMILES: CCOc1cc(=O)[nH]cc1-c1ccc(CC(=O)Nc2cc(C(=O)NCCN(C)C)cc(C(F)(F)F)c2)c(F)c1 ; Cl]

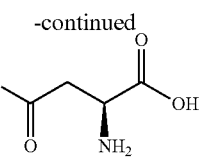

A suspension of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide (353.1 mg) in 8.4 mL of acetone was stirred for 15 min at 23° C. L-aspartic acid (99% purity, 85.1 mg, powder, 1.0 equivalent) was added and the sample was heated to 40° C. and then seeded with N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide. The sample was stirred and temperature-cycled between 40° C. and 5° C. for 6 h and then stirred at 20° C. for 0.5 h. The solids were isolated by vacuum filtration and dried in a vacuum oven at 40° C. for at least 16 hours to give the title compound as a crystalline solid. $^1$H NMR analysis (500 MHz, DMSO-d$_6$) indicated 1:1 acid:free base stoichiometry.

Seed Preparation

A suspension of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide (25 mg) in 0.6 mL of acetone was stirred for 30 min at 23° C. L-aspartic acid (6.1 mg) was added and the sample was heated to 40° C. The sample was stirred and temperature-cycled between 40° C. and 5° C. for 48 h, then stirred at 20° C. for 24 h, and then at 4° C. for 24 h. The solids were isolated by vacuum filtration and dried to give the title compound as a crystalline solid.

Figure 13:
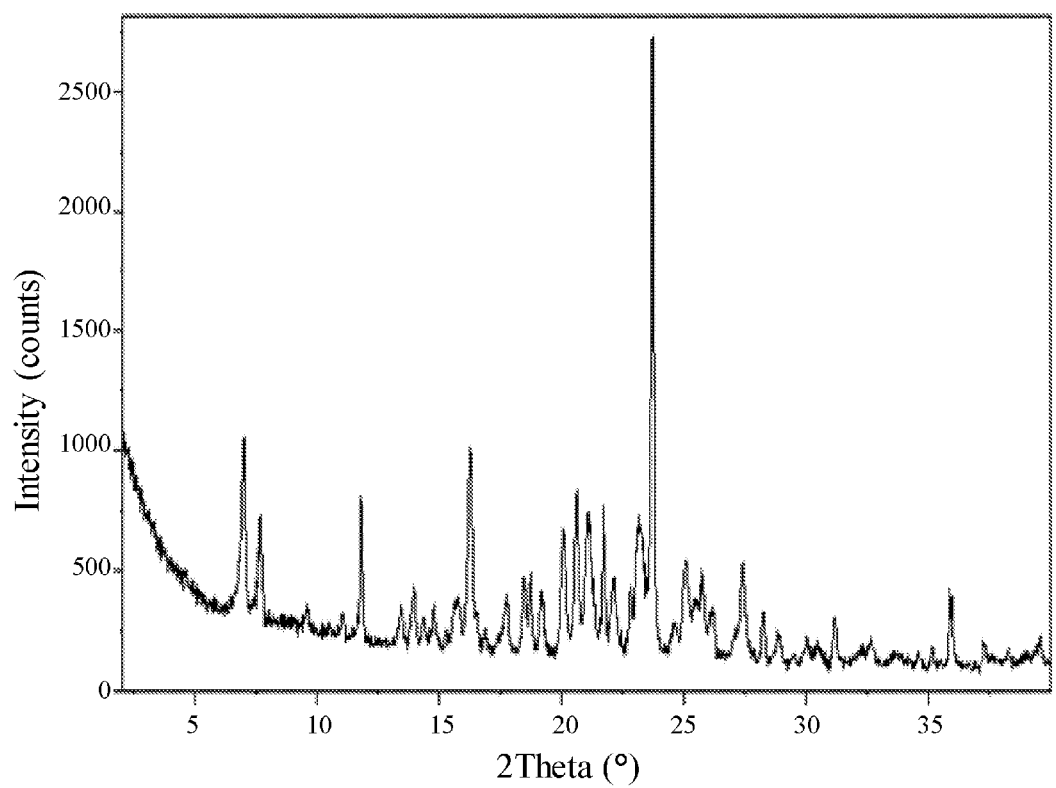
FIG. 13 shows an X-ray powder diffraction pattern of the aspartic acid salt of the compound of Formula (I).

The X-ray powder diffraction (XRPD) pattern of this material (the aspartic acid salt of the compound of Formula (I)) is shown in FIG. 13 and a summary of the diffraction angles and d-spacings is given in Table IV below. The XRPD analysis was conducted on a PANanalytical X'Pert Pro Diffractometer on Si zero-background wafers. The acquisition conditions included: Cu K$_\alpha$ radiation, generator tension: 45 kV, generator current: 40 mA, step size: 0.02° 2θ.

TABLE IV

| Diff. Angle [°2θ] | d-spacing [Å] |
|---|---|
| 6.7436 | 13.10777 |
| 6.9602 | 12.70047 |
| 7.6442 | 11.5654 |
| 11.7912 | 7.50553 |
| 13.9213 | 6.36149 |
| 14.7678 | 5.99377 |
| 15.5507 | 5.69372 |
| 15.6273 | 5.66596 |
| 15.7559 | 5.62001 |
| 16.241 | 5.45324 |
| 17.7233 | 5.00036 |
| 18.4499 | 4.80504 |
| 18.7127 | 4.73814 |
| 19.0754 | 4.64886 |
| 19.1568 | 4.62929 |
| 19.2284 | 4.62368 |
| 20.0643 | 4.42191 |
| 20.6095 | 4.30614 |
| 20.9589 | 4.23513 |
| 21.0645 | 4.21415 |
| 21.1555 | 4.20665 |
| 21.704 | 4.09141 |
| 22.0986 | 4.01922 |
| 22.8012 | 3.89694 |
| 23.0234 | 3.85984 |

TABLE IV-continued

| Diff. Angle [°2θ] | d-spacing [Å] |
|---|---|
| 23.1372 | 3.84111 |
| 23.2967 | 3.81516 |
| 23.694 | 3.75209 |
| 23.7674 | 3.74996 |
| 24.9715 | 3.56296 |
| 25.0549 | 3.55129 |
| 25.4173 | 3.50146 |
| 25.5014 | 3.49011 |
| 25.6884 | 3.46513 |
| 25.7417 | 3.45806 |
| 26.1759 | 3.40168 |
| 27.399 | 3.25254 |
| 28.2166 | 3.16013 |
| 31.1595 | 2.86805 |
| 35.8675 | 2.50164 |
| 35.9564 | 2.50187 |

Figure 14:
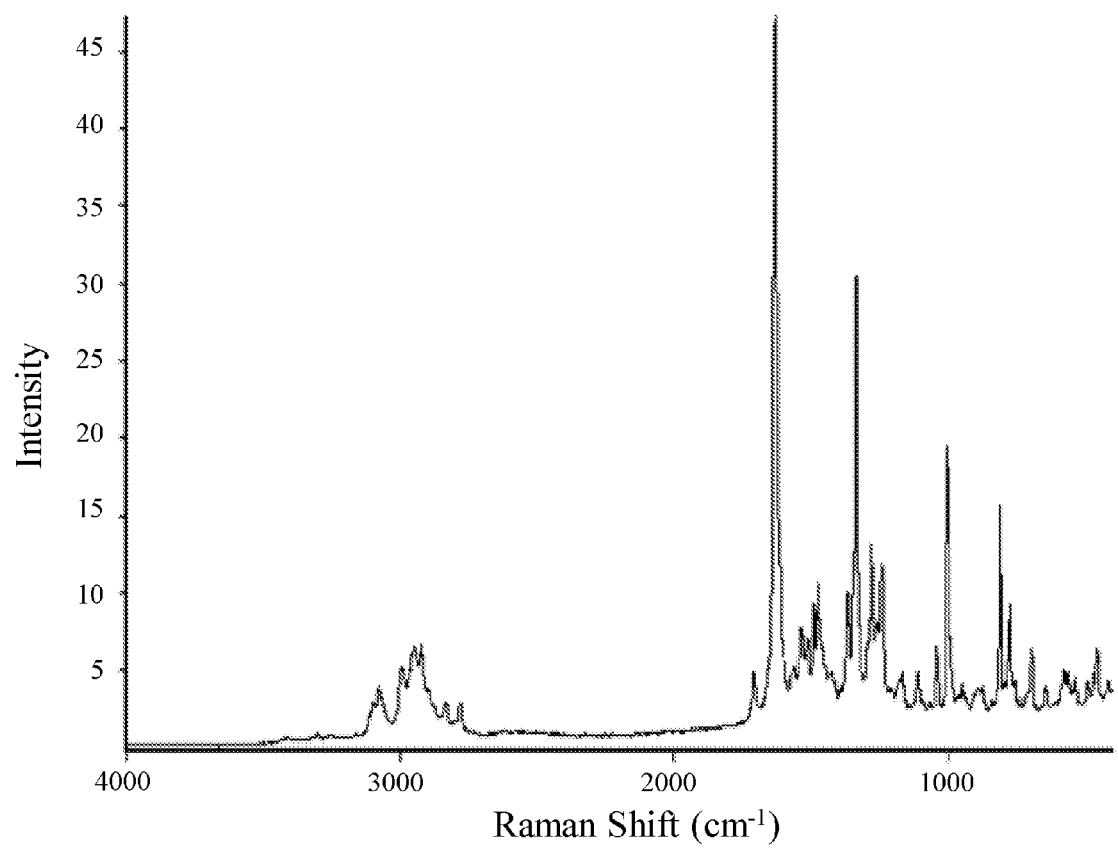
FIG. 14 shows a Raman spectrum of the aspartic acid salt of the compound of Formula (I).

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of this material is shown in FIG. 14 with major peaks observed at 452.2, 573.8, 690.5, 770.0, 806.8, 999.6, 1036.5, 1106.3, 1162.4, 1236.9, 1274.1, 1332.1, 1363.6, 1470.7, 1487.4, 1529.5, 1627.1, 1704.6, 2917.9, and 3072.7 cm$^{-1}$.

The differential scanning calorimetry (DSC) thermogram of the title compound was recorded on a TA Instruments Q100 Differential Scanning Calorimeter equipped with an autosampler and a refrigerated cooling system under 40 mL/min N$_2$ purge and is shown in FIG. 15. The experiments were conducted using a heating rate of 15° C./min in a crimped aluminum pan. The DSC thermogram of the aspartic acid salt of the compound of Formula (I) exhibited a sharp endotherm with an onset temperature of 220.62° C., a peak temperature about 223.04° C., and enthalpy of 75.76 J/g. A person skilled in the art would recognize that the onset temperature, peak temperature, and enthalpy of the endotherm may vary depending on the experimental conditions.

The thermogravimetric analysis (TGA) thermogram of the title compound was recorded on a TA Instruments Q500 Thermogravimetric Analyzer and is shown in FIG. 16. The experiments were conducted with 40 mL/min N$_2$ flow and a heating rate of 15° C./min. The TGA thermogram of the aspartic acid salt of the compound of Formula (I) exhibited negligible weight loss in the temperature range of 25° C. to 150° C. and a thermal decomposition onset temperature of 240.39° C.

Example 7: N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate

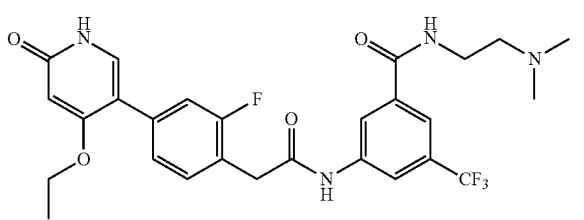

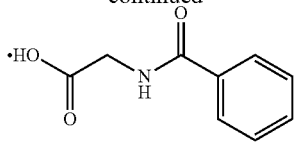

A suspension of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide (350 mg) in 8.4 mL of acetone was stirred for 15 min at 23° C. Hippuric acid (98% purity, 117.3 mg, powder, 1.0 equivalent) was added and the sample was heated to 40° C. and then seeded with N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide hippurate. The sample was stirred and temperature-cycled between 40° C. and 5° C. for 6 h and then stirred at 20° C. for 0.5 h. The solids were isolated by vacuum filtration and dried in a vacuum oven at 40° C. for at least 16 hours to give the title compound as a crystalline solid. $^1$H NMR analysis (500 MHz, DMSO-d$_6$) indicated 1:1 acid:free base stoichiometry.

Seed Preparation

A suspension of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide (25 mg) in 0.6 mL of acetone was stirred for 30 min at 23° C. Hippuric acid (8.4 mg) was added and the sample was heated to 40° C. The sample was stirred and temperature-cycled between 40° C. and 5° C. for 48 h, then stirred at 20° C. for 24 h, and then at 4° C. for 24 h. The solids were isolated by vacuum filtration and dried to give the title compound as a crystalline solid.

Figure 17:
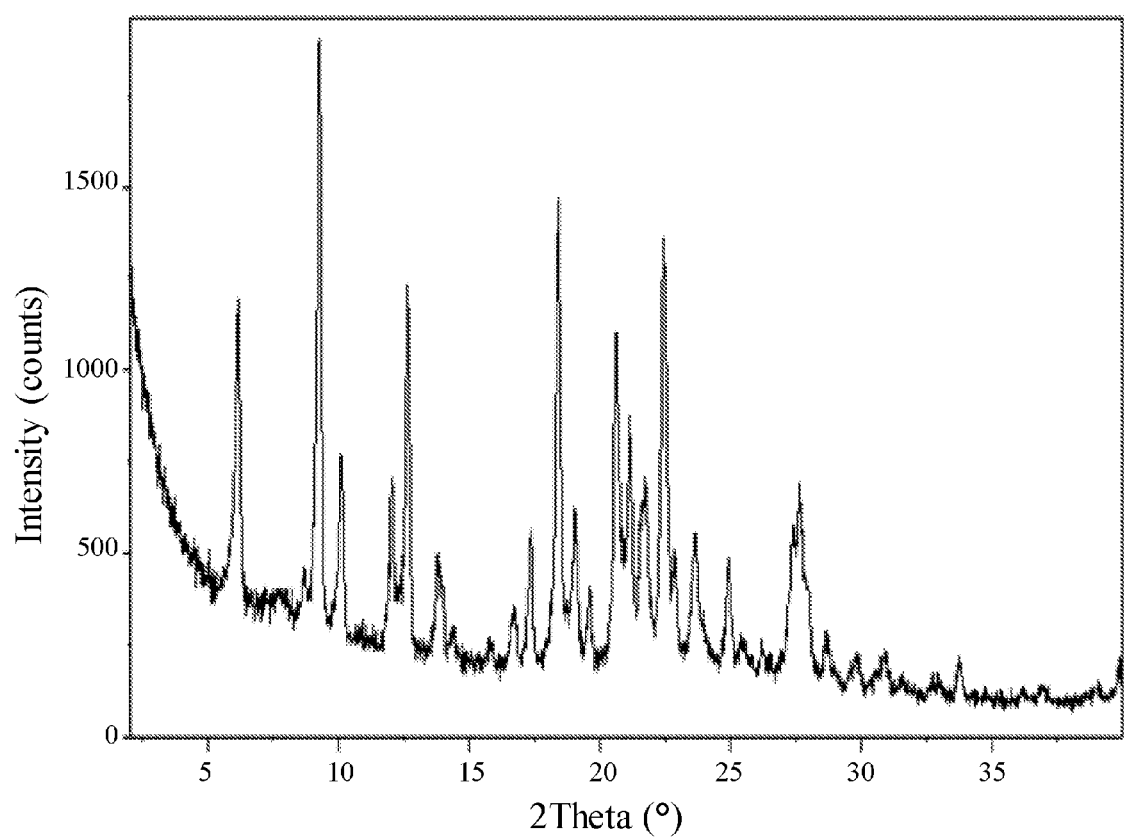
FIG. 17 shows an X-ray powder diffraction pattern of the hippuric acid salt of the compound of Formula (I).

The X-ray powder diffraction (XRPD) pattern of this material (the hippuric acid salt of the compound of Formula (I)) is shown in FIG. 17 and a summary of the diffraction angles and d-spacings is given in Table V below. The XRPD analysis was conducted on a PANanalytical X'Pert Pro Diffractometer on Si zero-background wafers. The acquisition conditions included: Cu K$_\alpha$ radiation, generator tension: 45 kV, generator current: 40 mA, step size: 0.02° 2θ.

TABLE V

| Diff. Angle [°2θ] | d-spacing [Å] |
|---|---|
| 6.1274 | 14.42462 |
| 9.2336 | 9.57788 |
| 10.068 | 8.78592 |
| 12.0304 | 7.35682 |
| 12.336 | 7.17522 |
| 12.625 | 7.01165 |
| 13.7792 | 6.42678 |
| 14.0043 | 6.32399 |
| 17.2054 | 5.15396 |
| 17.337 | 5.11513 |
| 18.0894 | 4.90404 |
| 18.3887 | 4.82487 |
| 18.9044 | 4.6944 |
| 19.022 | 4.66563 |
| 19.1238 | 4.64104 |
| 19.5997 | 4.52941 |
| 20.619 | 4.30774 |
| 21.1226 | 4.20269 |
| 21.2004 | 4.19785 |
| 21.5393 | 4.12231 |
| 21.7178 | 4.08883 |
| 22.4194 | 3.96243 |
| 22.8549 | 3.88791 |
| 23.4931 | 3.78371 |

TABLE V-continued

| Diff. Angle [°2θ] | d-spacing [Å] |
|---|---|
| 23.6345 | 3.7614 |
| 24.9064 | 3.57212 |
| 27.2014 | 3.27573 |
| 27.3599 | 3.2571 |
| 27.4394 | 3.25592 |
| 27.6333 | 3.2255 |
| 27.96 | 3.18854 |

Figure 18:
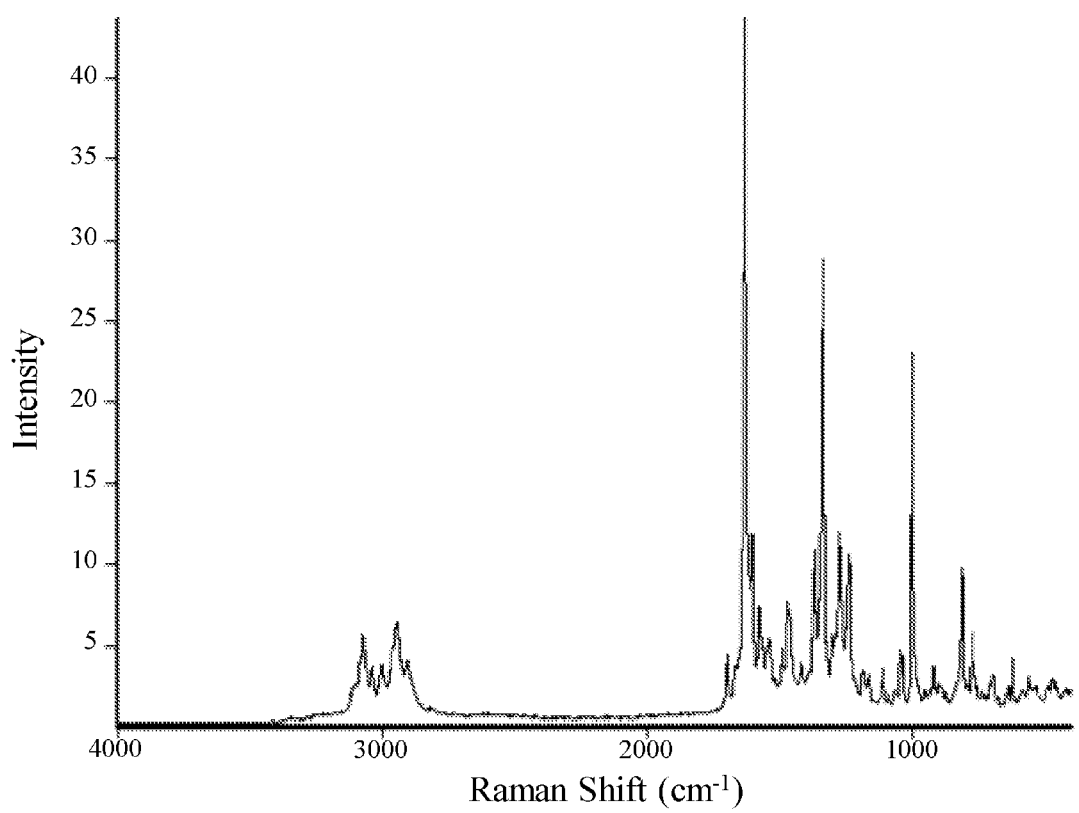
FIG. 18 shows a Raman spectrum of the hippuric acid salt of the compound of Formula (I).

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of this material is shown in FIG. 18 with major peaks observed at 556.6, 618.1, 694.0, 771.4, 809.0, 916.5, 997.2, 1041.9, 1108.4, 1235.8, 1272.2, 1335.1, 1366.2, 1466.6, 1537.0, 1575.4, 1601.4, 1630.2, 1695.0, 2943.8, and 3071.4 cm$^{1}$.

The differential scanning calorimetry (DSC) thermogram of the title compound was recorded on a TA Instruments Q100 Differential Scanning Calorimeter equipped with an autosampler and a refrigerated cooling system under 40 mL/min N$_2$ purge and is shown in FIG. 19. The experiments were conducted using a heating rate of 15° C./min in a crimped aluminum pan. The DSC thermogram of the hippuric acid salt of the compound of Formula (I) exhibited a sharp endotherm with an onset temperature of 232.10° C., a peak temperature about 233.32° C., and enthalpy of 123.1 J/g. A person skilled in the art would recognize that the onset temperature, peak temperature, and enthalpy of the endotherm may vary depending on the experimental conditions.

The thermogravimetric analysis (TGA) thermogram of the title compound was recorded on a TA Instruments Q500 Thermogravimetric Analyzer and is shown in FIG. 20. The experiments were conducted with 40 mL/min N$_2$ flow and a heating rate of 15° C./min. The TGA thermogram of the hippuric acid salt of the compound of Formula (I) exhibited negligible weight loss in the temperature range of 25° C. to 150° C. and a thermal decomposition onset temperature of 245.70° C.

Example 8: N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide phosphate

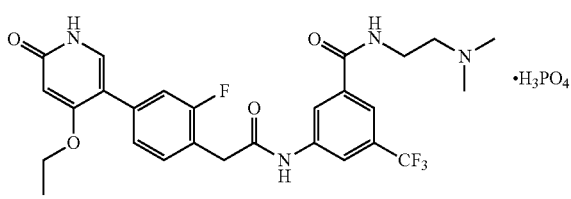

A suspension of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide (352 mg) in 8.4 mL of acetone was stirred for 15 min at 23° C. Phosphoric acid (3.0 M solution in water, 1.0 equivalent) was added and the sample was heated to 40° C. and then seeded with N-(2-(dimethylamino)ethyl)-3-(2-(4-(4-ethoxy-6-oxo-1, 6-dihydropyridin-3-yl)-2-fluorophenyl)acetamido)-5-(trifluoromethyl)benzamide phosphate. The sample was stirred and temperature-cycled between 40° C. and 5° C. for 6 h and then stirred at 20° C. for 0.5 h. The solids were isolated by vacuum filtration and dried in a vacuum oven at 40° C. for at least 16 hours to give the title compound as a crystalline solid. Inductively coupled plasma atomic emission spectroscopy indicated 1:1 acid:free base stoichiometry.

Seed Preparation

A suspension of N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide (25 mg) in 0.6 mL of acetone was stirred for 30 min at 23° C. Phosphoric acid (3.0 M solution in water, 1.0 equivalent) was added and the sample was heated to 40° C. The sample was stirred and temperature-cycled between 40° C. and 5° C. for 48 h, then stirred at 20° C. for 24 h, and then at 4° C. for 24 h. The solids were isolated by vacuum filtration and dried to give the title compound as a crystalline solid.

Figure 21:
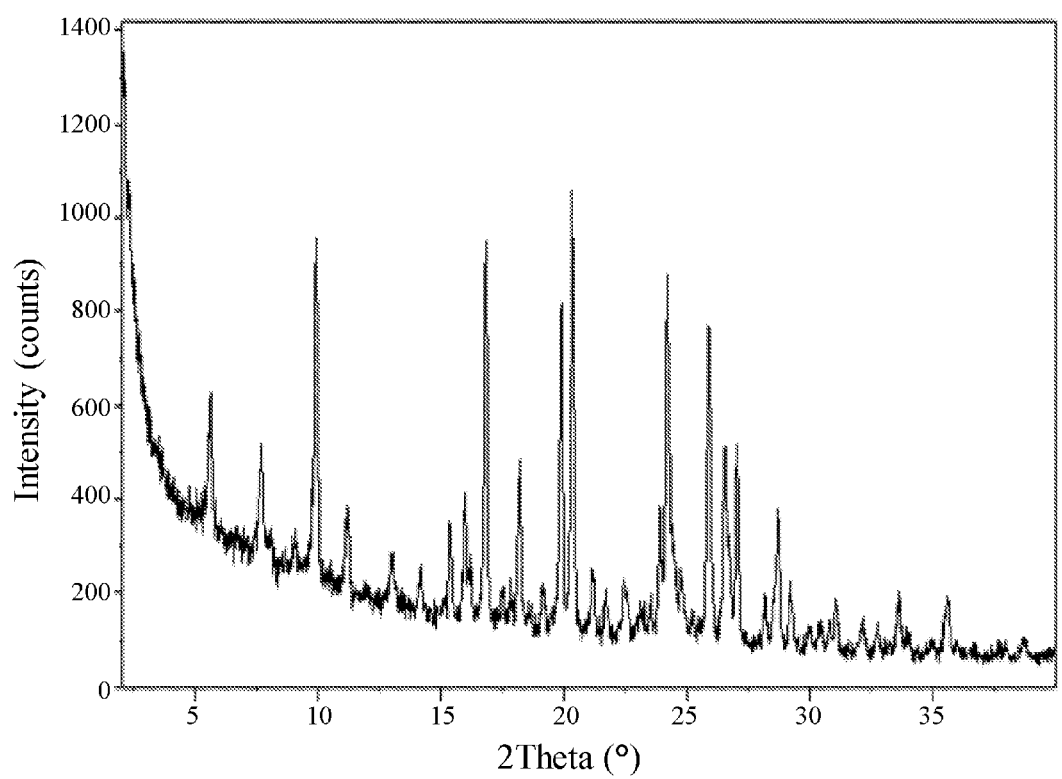
FIG. 21 shows an X-ray powder diffraction pattern of the phophoric acid salt of the compound of Formula (I).

The X-ray powder diffraction (XRPD) pattern of this material (the phosphoric acid salt of the compound of Formula (I)) is shown in FIG. 21 and a summary of the diffraction angles and d-spacings is given in Table VI below. The XRPD analysis was conducted on a PANanalytical X'Pert Pro Diffractometer on Si zero-background wafers. The acquisition conditions included: Cu K$_\alpha$ radiation, generator tension: 45 kV, generator current: 40 mA, step size: 0.02° 2θ.

TABLE VI

| Diff. Angle [°2θ] | d-spacing [Å] |
|---|---|
| 5.51 | 16.03945 |
| 5.605 | 15.76764 |
| 7.6688 | 11.52832 |
| 9.9043 | 8.93072 |
| 11.1846 | 7.91119 |
| 15.352 | 5.77173 |
| 15.9554 | 5.5548 |
| 16.8019 | 5.27679 |
| 18.1765 | 4.88073 |
| 19.8809 | 4.46227 |
| 20.3291 | 4.3649 |
| 23.8956 | 3.72088 |
| 24.1905 | 3.67619 |
| 24.4455 | 3.63841 |
| 26.5298 | 3.3571 |
| 26.7277 | 3.3327 |
| 27.0256 | 3.29663 |
| 28.6856 | 3.10952 |

Figure 22:
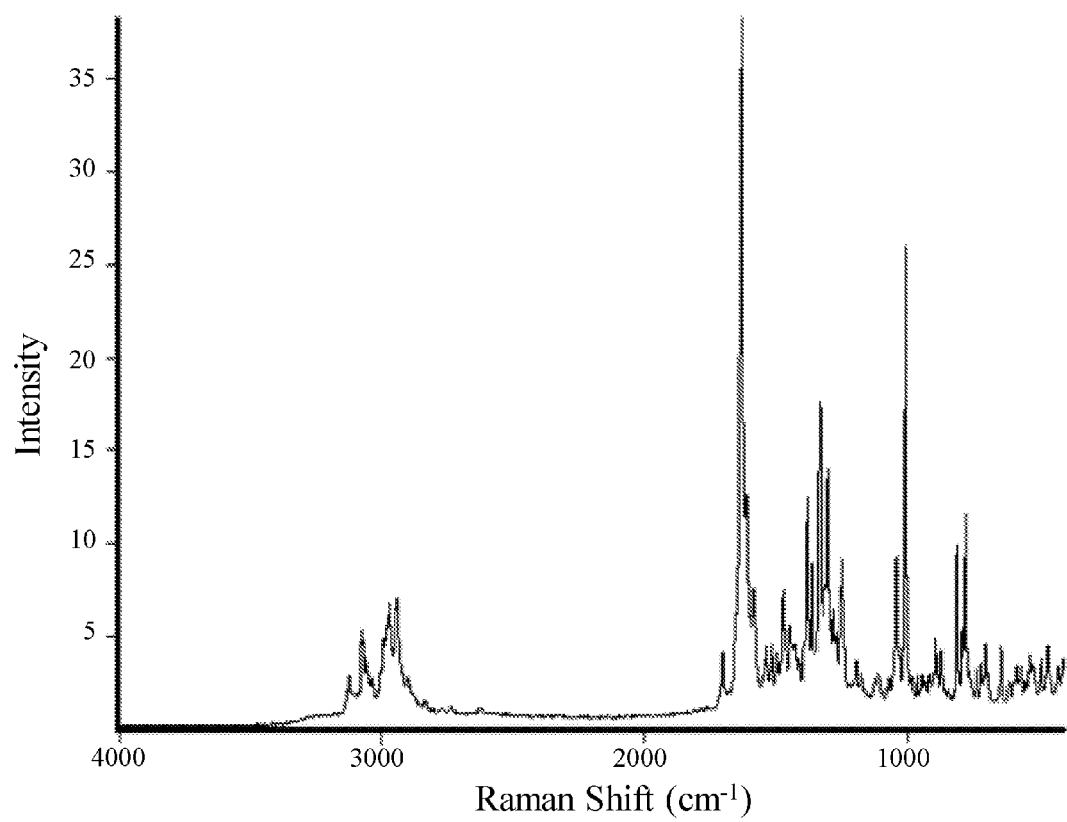
FIG. 22 shows a Raman spectrum of the phophoric acid salt of the compound of Formula (I).

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of this material is shown in FIG. 22 with major peaks observed at 460.6, 484.5, 529.3, 577.0, 637.8, 696.3, 731.9, 773.1, 786.2, 805.7, 866.9, 888.7, 1002.3, 1035.6, 1187.1, 1242.7, 1275.9, 1296.0, 1326.2, 1357.6, 1375.1, 1441.7, 1466.0, 1510.1, 1531.6, 1580.3, 1624.5, 1698.2, 2936.4, 2964.1, and 3068.6 cm$^{-1}$.

The differential scanning calorimetry (DSC) thermogram of the title compound was recorded on a TA Instruments Q100 Differential Scanning Calorimeter equipped with an autosampler and a refrigerated cooling system under 40 mL/min N$_2$ purge and is shown in FIG. 23. The experiments were conducted using a heating rate of 15° C./min in a crimped aluminum pan. The DSC thermogram of the phosphoric acid salt of the compound of Formula (I) exhibited a sharp endotherm with an onset temperature of 235.69° C., a peak temperature about 242.24° C., and enthalpy of 135.3 J/g. A person skilled in the art would recognize that the onset temperature, peak temperature, and enthalpy of the endotherm may vary depending on the experimental conditions.

The thermogravimetric analysis (TGA) thermogram of the title compound was recorded on a TA Instruments Q500 Thermogravimetric Analyzer and is shown in FIG. 24. The experiments were conducted with 40 mL/min $N_2$ flow and a heating rate of 15° C./min. The TGA thermogram of the phosphoric acid salt of the compound of Formula (I) exhibited negligible weight loss in the temperature range of 25° C. to 150° C. and a thermal decomposition onset temperature of 237.30° C.

Biological Assays

The compounds of the present invention were tested for RET kinase inhibitory activity in a RET kinase enzyme assay, a cell-based mechanistic assay and a cell-based proliferation assay.

RET Kinase Enzymatic Assay

Human RET kinase cytoplasmic domain (amino acids 658-1114 of accession number NP_000314.1) was expressed as an N-terminal GST-fusion protein using a baculovirus expression system. GST-RET was purified using glutathione sepharose chromatography. The RET kinase enzymatic assay was performed in a total volume of 10 uL with increasing concentrations of RET kinase inhibitor as a singlet in a 384 well format as follows: RET inhibitor compound plates are prepared by adding 100 nL of RET inhibitor at different concentrations to a 384-well plate. 5 μL/well of a 2× enzyme mix (50 mM HEPES (4-(2-hydroxyethyl)-1-piperazineethanesulfonic acid); 1 mM CHAPS (3-[(3-cholamidopropyl)dimethylammonio]-1-propanesulfonate); 0.1 mg/mL BSA (bovine serum albumin); 1 mM DTT (dithiothreitol); 0.2 nM RET kinase) was added to the 384-well plate and incubated for 30 minutes at 23° C. 5 μL/well of a 2× substrate mix (50 mM HEPES; 1 mM CHAPS; 0.1 mg/mL BSA; 20 μM adenosine triphosphate; 20 mM $MgCl_2$ and 1 μM biotinylated peptide substrate) was added and incubated for 1 hour at 23° C. 10 μL/well of 2× stop/detection mix (50 mM HEPES; 0.1% BSA; 800 mM Potassium Fluoride; 50 mM EDTA (Ethylenediaminetetraacetic acid); 200× dilution of Europium Cryptate labeled anti-phosphotyrosine antibody; 62.5 nM Streptavidin-XL665) incubated for 1 hour at 23° C. and read on a Homogenous Time-Resolved Fluorescence reader. $IC_{50}$s were fitted using GraphPad Prism to a sigmoidal dose response.

RET Kinase Cell-Based Mechanistic Assay

The potency of the compounds of the invention were tested for its ability to inhibit constitutive RET kinase phosphorylation in cell-based assay. TT cells (ATCC CRL-1803), a medullary thyroid cancer cell line with constitutively activated RET kinase, were maintained in 150 $cm^2$ dishes in F12 Kaighn's medium, 10% fetal bovine serum, 1× Glutamax, 1× non-essential amino acids, 1× Pen/Strep antibiotics at 37° C. in 5% carbon dioxide. 1.0E5 TT cells/well were plated in a 96-well cell culture plate and allowed to adhere overnight. TT cells were treated with different concentrations of RET inhibitor compounds for 2 h at 37° C. in 5% carbon dioxide, washed with ice cold PBS (phosphate buffered saline) and lysed by adding 200 μL of 25 mM Tris HCl pH 7.5; 2 mM EDTA; 150 mM NaCl; 1% sodium deoxycholate; 1% Triton X-100; 50 mM sodium beta glycerophosphate; 1 mM sodium orthovanadate; 1× phosphatase inhibitor cocktail #2 (Sigma #P5726); 1× phosphatase inhibitor cocktail #3 (Sigma #P0044) and 1× complete mini EDTA free protease inhibitor cocktail (Roche #4693159001), incubation at −80° C. for 10 minutes and thawed on ice. 100 μL of TT cell lysate was added to a 96-well plate overnight at 4° C. that had been coated overnight at 4° C. with 1:1,000 dilution of a rabbit anti-RET antibody (Cell Signaling #7032) blocked with 1×PBS; 0.05% Tween-20; 1% bovine serum albumin. Plates were washed 4× with 200 μL of 1×PBS; 0.05% Tween-20 and then 100 μL of a 1:1,000 dilution of an anti-phosphotyrosine detection antibody (Cell Signaling #7034) was added and incubated for 1 hour at 37° C. Plates were washed 4× with 200 μL of 1×PBS; 0.05% Tween-20 and then 100 μL of a 1:1,000 dilution of an anti-mouse immunoglobulin horse radish peroxidase conjugate antibody (Cell Signaling #7034) was added and incubated for 30 minutes at 37° C. Plates were washed 4× with 200 μL of 1×PBS; 0.05% Tween-20, 100 μL of TMB (3,3',5,5"-tetramethylbenzidine) substrate (Cell Signaling #7004) was added, incubated for 10 minutes at 37° C., 100 μL of Stop solution (Cell Signaling #7002) was added and absorbance read on a spectrophotometer at 450 nm. $IC_{50}$s were fitted using GraphPad Prism to a sigmoidal dose response.

RET Kinase Cell-Based Proliferation Assay

The potency of the compounds of the invention were tested for its ability to inhibit cell proliferation and cell viability. TT cells (ATCC CRL-1803), a medullary thyroid cancer cell line with constitutively activated RET kinase, were maintained in 150 $cm^2$ dishes in F12 Kaighn's medium, 10% fetal bovine serum, 1× Glutamax, 1× non-essential amino acids, 1× Pen/Strep antibiotics at 37° C. in 5% carbon dioxide. 6.0E3 TT cells/well in 50 μL of media were added to a 96-well cell culture plate and allowed to adhere overnight. 50 μL of serially diluted RET inhibitor compounds were added to 96-well plate containing cultured TT cells and incubated at 37° C. in 5% carbon dioxide for eight days. 50 μL of CellTiter-Glo (Promega #G-7573) was added, contents mixed for 1 minute on shaker followed by 10 minutes in the dark at 23° C. and the luminescence read by EnVision (PerkinElmer). $IC_{50}$s were fitted using GraphPad Prism to a sigmoidal dose response.

Biological Data

Exemplified compounds of the present invention were tested in the RET assays described above and were found to be inhibitors of RET with $IC_{50}$<10 μM. Data for specific examples tested are listed below in Table 1 as follows: +=10 μM>$IC_{50}$>100 nM; ++=100 nM≥$IC_{50}$>10 nM; +++=$IC_{50}$≤10 nM.

TABLE 1

| Example # | Human RET kinase enzymatic $IC_{50}$ | Human RET kinase cell-based mechanistic $IC_{50}$ | Human RET kinase cell-based proliferation $IC_{50}$ |
| --- | --- | --- | --- |
| 1 | +++ | ++ | ++ |
| 2 | +++ | ++ | ++ |

In Vivo Colonic Hypersensitivity Model

The efficacy of RET kinase inhibitor compounds can be evaluated in an in vivo model of colonic hypersensitivity (Hoffman, J. M., et al., Gastroenterology, 2012, 142:844-854).

The invention claimed is:

1. A compound which is N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide, represented by Formula (I):

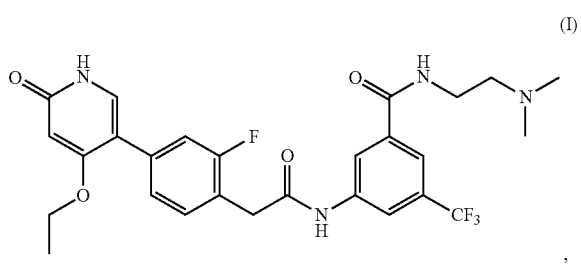 [SMILES: CCOc1cc(=O)[nH]cc1-c1ccc(CC(=O)Nc2cc(C(=O)NCCN(C)C)cc(C(F)(F)F)c2)c(F)c1]

or a pharmaceutically acceptable salt thereof.

2. A compound which is N-(2-(dimethylamino)ethyl)-3-(2-(4-(4-ethoxy-6-oxo-1,6-dihydropyridin-3-yl)-2-fluorophenyl)acetamido)-5-(trifluoromethyl)benzamide, represented by Formula (I):

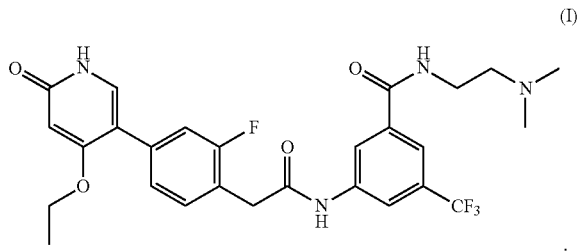 [SMILES: CCOc1cc(=O)[nH]cc1-c1ccc(CC(=O)Nc2cc(C(=O)NCCN(C)C)cc(C(F)(F)F)c2)c(F)c1]

3. The pharmaceutically acceptable salt of the compound according to claim 1 which is selected from the group consisting of the hydrochloric acid salt, aspartic acid salt, hippuric acid salt, and phosphoric acid salt.

4. The pharmaceutically acceptable salt of the compound according to claim 1 which is the hydrochloric acid salt.

5. The pharmaceutically acceptable salt according to claim 4 which is in crystalline form.

6. The pharmaceutically acceptable salt according to claim 5, wherein the crystalline form is characterized by an X-ray powder diffraction (XRPD) pattern comprising at least three diffraction angles, when measured using Cu $K_\alpha$ radiation, selected from a group consisting of about 8.3, 8.4, 10.7, 11.3, 15.5, 16.0, 20.0, 20.4, 20.8, 22.6, 23.2, 23.3, 23.6, 24.6, 24.9, 25.3, 25.9, 26.9, 27.3, 27.4, 28.1, and 28.2 degrees 2θ.

7. The pharmaceutically acceptable salt according to claim 5, wherein the crystalline form is characterized by an X-ray powder diffraction (XRPD) pattern comprising diffraction angles, when measured using Cu $K_\alpha$ radiation, of about 16.0, 20.0, 22.6, 23.3, and 26.9 degrees 2θ.

8. A pharmaceutical composition comprising the compound or pharmaceutically acceptable salt according to claim 1 and a pharmaceutically acceptable excipient.

9. A pharmaceutical composition comprising the pharmaceutically acceptable salt according to claim 4 and a pharmaceutically acceptable excipient.

10. A pharmaceutical composition comprising the pharmaceutically acceptable salt according to claim 7 and a pharmaceutically acceptable excipient.

11. A method of treating a disease mediated by Rearranged during Transfection kinase, selected from the group consisting of irritable bowel syndrome, pain associated with irritable bowel syndrome, functional constipation, functional diarrhea, chronic idiopathic constipation, functional abdominal pain syndrome, functional anorectal pain, and inflammatory bowel disease, comprising administering to a human in need thereof an effective amount of the compound or pharmaceutically acceptable salt according to claim 1.

12. A method of treating a disease mediated by Rearranged during Transfection kinase, selected from the group consisting of irritable bowel syndrome, pain associated with irritable bowel syndrome, functional constipation, functional diarrhea, chronic idiopathic constipation, functional abdominal pain syndrome, functional anorectal pain, and inflammatory bowel disease, comprising administering to a human in need thereof an effective amount of the pharmaceutically acceptable salt according to claim 4.

13. A method of treating a disease mediated by Rearranged during Transfection kinase, selected from the group consisting of irritable bowel syndrome, pain associated with irritable bowel syndrome, functional constipation, functional diarrhea, chronic idiopathic constipation, functional abdominal pain syndrome, functional anorectal pain, and inflammatory bowel disease, comprising administering to a human in need thereof an effective amount of the pharmaceutically acceptable salt according to claim 7.

14. The method according to claim 11 wherein the disease is irritable bowel syndrome.

15. The method according to claim 12 wherein the disease is irritable bowel syndrome.

16. The method according to claim 13 wherein the disease is irritable bowel syndrome.

17. The method according to claim 11 wherein the disease is pain associated with irritable bowel syndrome.

18. The method according to claim 12 wherein the disease is pain associated with irritable bowel syndrome.

19. The method according to claim 13 wherein the disease is pain associated with irritable bowel syndrome.

* * * * *